(12) United States Patent
Kawamura et al.

(10) Patent No.: US 8,025,815 B2
(45) Date of Patent: *Sep. 27, 2011

(54) NAPHTHALENE DERIVATIVE, MATERIAL FOR ORGANIC ELECTROLUMINESCENCE DEVICE, AND ORGANIC ELECTROLUMINESCENCE DEVICE USING THE SAME

(75) Inventors: Masahiro Kawamura, Sodegaura (JP); Kazuki Nishimura, Sodegaura (JP); Yoriyuki Takashima, Sodegaura (JP); Mitsunori Ito, Sodegaura (JP); Toshihiro Iwakuma, Sodegaura (JP); Toshinari Ogiwara, Sodegaura (JP); Chishio Hosokawa, Sodegaura (JP); Kenichi Fukuoka, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 703 days.

This patent is subject to a terminal disclaimer.

(21) Appl. No.: 12/102,457

(22) Filed: Apr. 14, 2008

(65) Prior Publication Data

US 2009/0008605 A1  Jan. 8, 2009

(30) Foreign Application Priority Data

Jul. 7, 2007  (JP) ................... 2007-179120
Jul. 7, 2007  (JP) ................... 2007-179121

(51) Int. Cl.
*C09K 11/00* (2006.01)
*C07C 15/00* (2006.01)
*C07C 15/20* (2006.01)

(52) U.S. Cl. .................... 252/301.16; 585/26
(58) Field of Classification Search ............ 252/301.16; 585/26
See application file for complete search history.

(56) References Cited

U.S. PATENT DOCUMENTS

2002/0182441 A1  12/2002 Lamansky et al.

FOREIGN PATENT DOCUMENTS

JP  2001-332384  11/2001

(Continued)

OTHER PUBLICATIONS

Dieter E. Kaufmann, et al. "Suzuki Coupling of Chiral 1,1' -Binaphthyl Systems—New Synthetic Routes to Functionalize the 2- and 2,2' -Positions" Eur. J. Org. Chem., No. 4, (pp. 701-709), 1998.

(Continued)

*Primary Examiner* — Duc Truong
(74) *Attorney, Agent, or Firm* — Oblon, Spivak, McClelland, Maier & Neustadt, L.L.P.

(57) ABSTRACT

A naphthalene derivative represented by the following formula (1) is provided. In the formula, $Ar^1$ to $Ar^4$ each represent an aromatic hydrocarbon cyclic group having 6 to 18 carbon atoms forming a ring. The aromatic hydrocarbon cyclic group has none of anthracene skeleton, pyrene skeleton, aceanthrylene skeleton and naphthacene skeleton. n, m and l each represent an integer in a range of 1 to 5. p represents an integer in a range of 0 to 5. When n, m, l and p each are 2 or more, a plurality of $Ar^1$ to $Ar^4$ may be mutually the same or different.

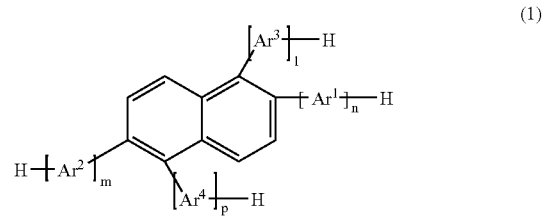

(1)

15 Claims, 1 Drawing Sheet

FOREIGN PATENT DOCUMENTS

| | | |
|---|---|---|
| JP | 2003-142267 | 5/2003 |
| JP | 2004-18510 | 1/2004 |
| JP | 2005-8588 | 1/2005 |
| JP | 2005-19219 | 1/2005 |
| JP | 2006-151966 | 6/2006 |
| JP | 2007-84485 | 4/2007 |
| WO | WO 02/052905 A1 | 7/2002 |
| WO | WO 2005/112519 A1 | 11/2005 |
| WO | WO 2006/103916 A1 | 10/2006 |
| WO | WO 2007/046658 A1 | 4/2007 |

OTHER PUBLICATIONS

Masahiko Iyoda, et al. "A Cyclic Oligophenylene Containing Two 1,8-Naphthalene Units Bridged by Two Face-to-Face Biphenyl Linkages Exhibiting Unusual Strain and π-π Interaction" Organic Letters, vol. 2, No. 14, (pp. 2081-2083), 2000.

Kuiling Ding, et al. "Self-Supported Heterogeneous Titanium Catalysts for Enantioselective Carbonyl-Ene and Sulfoxidation Reactions" Chem. Eur. J., vol. 11, No. 14, (pp. 4078-4088), 2005.

Michael J. Therien, et al. "Distance Dependence of Electron Transfer in Rigid, Cofacially Compressed, π -Stacked Porphyrin-Bridge-Quinone Systems" J. AM. Chem. Society, vol. 124, No. 28, (pp. 8275-8279), 2002.

Francois Diederich, et al. "Dendritic, 1,1'-Binaphthalene-Derived Cleft-Type Receptors (Dendroclefts) for the Molecular Recognition of Pyranosides" Helvetica Chimica Acta, vol. 83 No. 7. (pp. 1346-1376), 2000.

U.S. Appl. No. 12/102,484, filed Apr. 14, 2008, Kawamura et al.
U.S. Appl. No. 12/102,562, filed Apr. 14, 2008, Kawamura et al.
U.S. Appl. No. 12/102,401, filed Apr. 14, 2008, Kawamura et al.

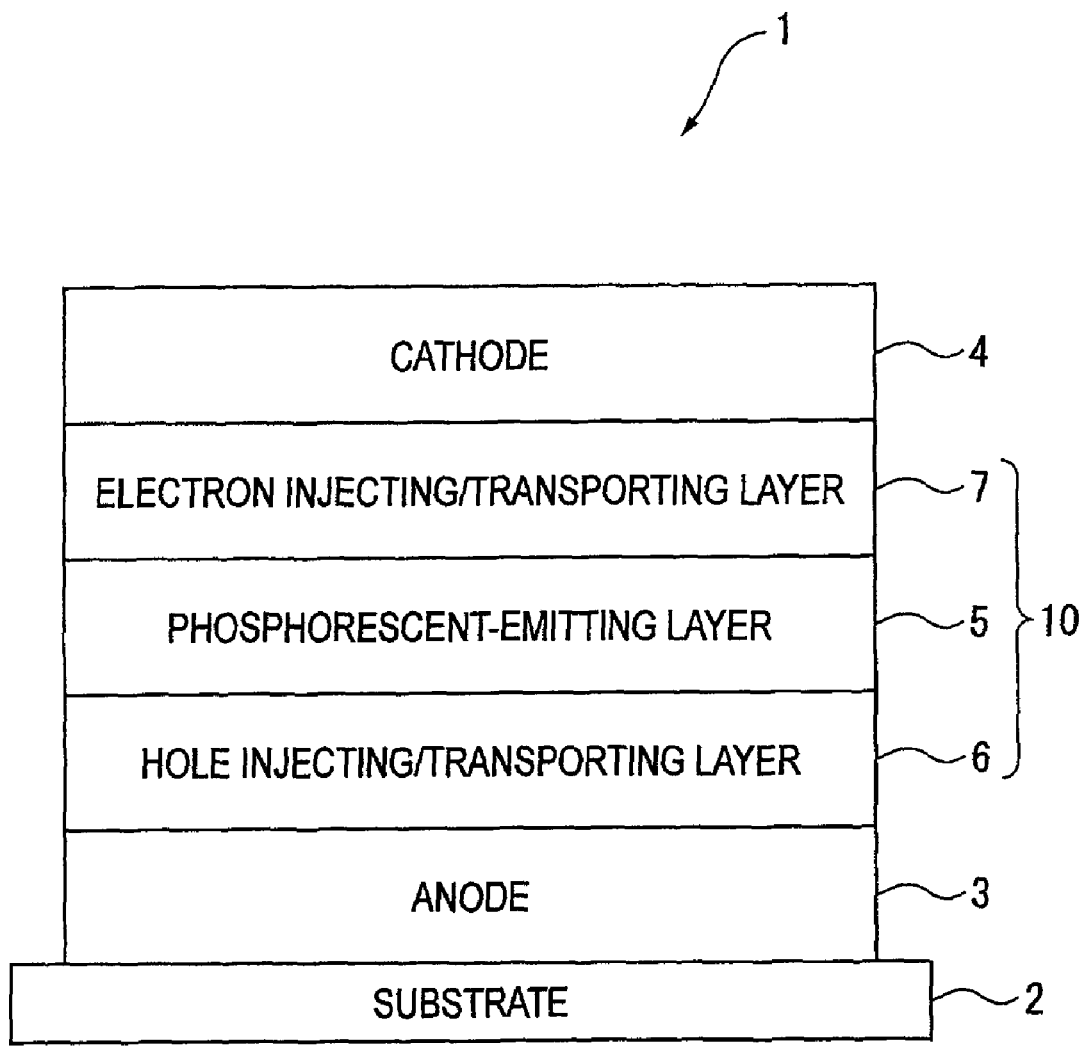

NAPHTHALENE DERIVATIVE, MATERIAL FOR ORGANIC ELECTROLUMINESCENCE DEVICE, AND ORGANIC ELECTROLUMINESCENCE DEVICE USING THE SAME

BACKGROUND OF THE INVENTION

1. Field of the Invention

The present invention relates to a naphthalene derivative, a material for an organic electroluminescence device and an organic electroluminescence device using the same.

2. Description of Related Art

An organic electroluminescence device (hereinafter called as organic EL device), which includes an organic emitting layer between an anode and a cathode, has been known to emit light using exciton energy generated by a recombination of holes and electrons that have been injected into the organic emitting layer.

Such an organic EL device, which has the advantages as a self-emitting device, is expected to serve as an emitting device excellent in luminous efficiency, image quality, power consumption and thin design.

In applying an emitting material to an organic EL device, a doping method, according to which a dopant material is doped to a host material, has been known as a usable method.

In order to effectively generate exciton from injected energy and effectively convert exciton energy into light emission, an organic EL device is arranged such that the exciton energy generated in a host is transferred to a dopant, and that the dopant emits light.

Examples of such a host and dopant are such condensed aromatic compounds each having a naphthalene skeleton as disclosed in Document 1 (JP-A-2007-84485), Document 2 (JP-A-2006-151966), Document 3 (JP-A-2005-19219), Document 4 (JP-A-2005-8588), Document 5 (JP-A-2004-18510), Document 6 (WO2007/46658) and Document 7 (JP-A-2003-142267).

However, although there has been a demand for an organic EL device that is free from pixel defects and excellent in luminous efficiency, heat resistance and lifetime, no material for an organic EL device or no host material has been found usable for providing such an excellent organic EL device.

On the other hand, in order to enhance internal quantum efficiency and achieve higher luminous efficiency, a phosphorescence material that emits light using triplet exciton has been developed. Recently, there has been a report on an organic device using phosphorescence emission.

Since the internal quantum efficiency can be enhanced up to 75% or more (up to approximately 100% in theory) by using such a phosphorescence material, an organic EL device having high efficiency and consuming less power can be obtained.

However, although exhibiting much higher luminous efficiency, such a conventional phosphorescent organic EL device has such a short lifetime as to be practically inapplicable.

SUMMARY OF THE INVENTION

In view of the above problems, an object of the present invention is to provide an organic EL device that is free from pixel defects and excellent in luminous efficiency, heat resistance and lifetime, and to provide a naphthalene derivative and a material for an organic EL device capable of realizing such an organic EL device.

After conducting concentrated studies in order to achieve such an object, the inventors have found that an organic EL device that is free from pixel defects and excellent in efficiency, heat resistance and lifetime can be provided by using a naphthalene derivative represented by the following formula (1) as the material for the organic EL device, and reached the present invention.

A naphthalene derivative according to an aspect of the present invention is represented by the following formula (1).

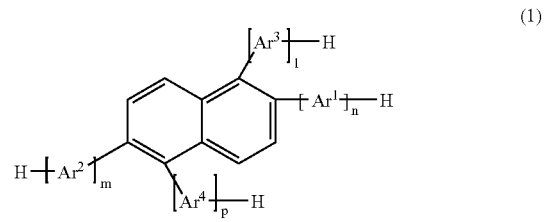

(1)

In the formula (1), $Ar^1$ to $Ar^4$ each represent an aromatic hydrocarbon cyclic group having 6 to 18 carbon atoms forming a ring. The aromatic hydrocarbon cyclic group has none of anthracene skeleton, pyrene skeleton, aceanthrylene skeleton and naphthacene skeleton.

n, m and l each represent an integer in a range of 1 to 5. p represents an integer in a range of 0 to 5.

When n, m, l and p each are 2 or more, a plurality of $Ar^1$ to $Ar^4$ may be mutually the same or different.

When the naphthalene derivative has a structure in which two naphthalene skeletons are consecutively bonded together, the structure of the naphthalene derivative is represented by any one of formulae (1-A), (1-B), (1-C) and (1-D) as follows.

(1-A)

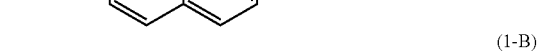

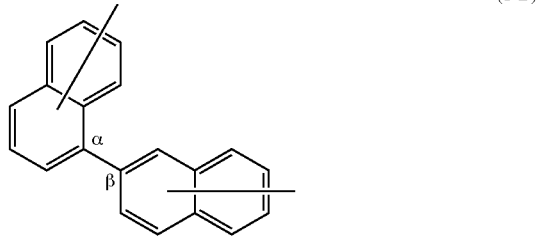

(1-B)

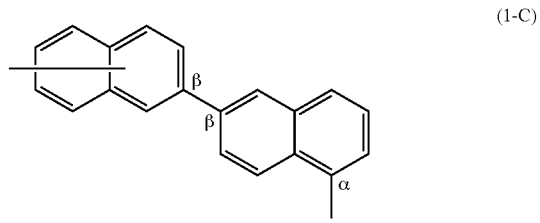

(1-C)

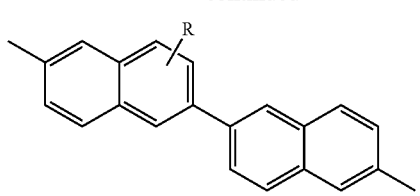

(1-D)

The naphthalene skeletons represented by the formulae (1-A), (1-B) and (1-C) each may have a substituent(s) in any suitable position(s) or may be unsubstituted.

R in the formula (1-D) represents a substituent. R may represent a single substituent or plural substituents. The substituent(s) may be in any position(s) of the two naphthalene skeletons. When R represents the plural substituents, the plural substituents may be mutually the same or different.

When the naphthalene derivative has a structure in which three naphthalene skeletons are consecutively bonded together, a naphthalene skeleton of the three naphthalene skeletons that is positioned at the center of the structure is tetravalent or more while at least either one of the other naphthalene skeletons of the three naphthalene skeletons that are positioned at ends of the structure is trivalent or more.

When the naphthalene derivative has a structure in which four naphthalene skeletons are consecutively bonded together, at least one of the naphthalene skeletons is tetravalent or more.

When the naphthalene derivative contains a plurality of unsubstituted 9-phenanthrenes, the number of the unsubstituted 9-phenanthrenes is 3 or more.

In the naphthalene derivative, when $Ar^1$ to $Ar^4$ each represent a phenanthrene skeleton, the phenanthrene skeleton is monovalent.

A material for an organic EL device according another aspect of the present invention contains the naphthalene derivative represented by the formula (1).

An organic EL device according to still further aspect of the present invention includes: a cathode; an anode; an organic thin-film layer provided between the anode and the cathode, the organic thin-film layer including at least one layer, the at least one layer including an emitting layer, in which the at least one layer of the organic thin-film layer contains the naphthalene derivative represented by the formula (1).

EFFECT(S) OF THE INVENTION

According to the aspect(s) of the present invention, an organic EL device that is free from pixel defects and excellent in luminous efficiency, heat resistance and lifetime can be provided. In addition, a naphthalene derivative and a material for an organic EL device capable of realizing such an organic EL device can be provided.

BRIEF DESCRIPTION OF THE DRAWINGS

FIG. 1 schematically shows an exemplary arrangement of an organic EL device according to an exemplary embodiment of the present invention.

DETAILED DESCRIPTION OF PREFERRED EMBODIMENT(S)

Embodiment(s) of the present invention will be described below.

[Naphthalene Derivative]

A naphthalene derivative according to an aspect of the present invention is represented by the following formula (1).

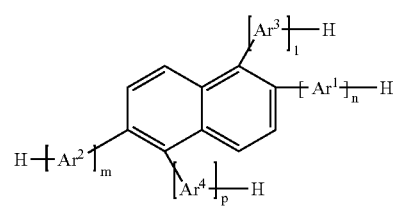

(1)

In the formula (1), $Ar^1$ to $Ar^4$ each represent an aromatic hydrocarbon cyclic group having 6 to 18 carbon atoms forming a ring. The aromatic hydrocarbon cyclic group has none of anthracene skeleton, pyrene skeleton, aceanthrylene skeleton and naphthacene skeleton.

n, m and l each represent an integer in a range of 1 to 5. p represents an integer in a range of 0 to 5.

Structures of ($—[Ar^1]_n—H$) when n takes an integer value of 1 to 5 are represented by the following formulae (1-n-1) to (1-n-5) respectively:

the structure when n is 1 is represented by $—Ar^{1a}—H$      (1-n-1);

the structure when n is 2 is represented by $—Ar^{1a}—Ar^{1b}—H$      (1-n-2);

the structure when n is 3 is represented by $—Ar^{1a}—Ar^{1b}—Ar^{1c}—H$      (1-n-3);

the structure when n is 4 is represented by $—Ar^{1a}—Ar^{1b}—Ar^{1c}—Ar^{1d}—H$      (1-n-4);

and the structure when n is 5 is represented by $—Ar^{1a}—Ar^{1b}—Ar^{1c}—Ar^{1d}—Ar^{1e}—H$      (1-n-5).

Structures of ($—[Ar^2]_m—H$) when m takes an integer value of 1 to 5 are represented by the following formulae (1-m-1) to (1-m-5) respectively:

the structure when m is 1 is represented by $—Ar^{2a}—H$      (1-m-1);

the structure when m is 2 is represented by $—Ar^{2a}—Ar^{2b}—H$      (1-m-2);

the structure when m is 3 is represented by $—Ar^{2a}—Ar^{2b}—Ar^{2c}—H$      (1-m-3);

the structure when m is 4 is represented by $—Ar^{2a}—Ar^{2b}—Ar^{2c}—Ar^{2d}—H$      (1-m-4);

and the structure when m is 5 is represented by $—Ar^{2a}—Ar^{2b}Ar^{2c}—Ar^{2d}—Ar^{2e}—H$      (1-m-5).

Structures of ($—[Ar^3]_l—H$) when l takes an integer value of 1 to 5 are represented by the following formulae (1-l-1) to (1-l-5) respectively:

the structure when l is 1 is represented by $—Ar^{3a}—H$      (1-l-1);

the structure when l is 2 is represented by $—Ar^{3a}—Ar^{3b}—H$      (1-l-2);

the structure when l is 3 is represented by $—Ar^{3a}—Ar^{3b}—Ar^{3c}—H$      (1-l-3);

the structure when l is 4 is represented by —Ar$^{3a}$—Ar$^{3b}$—Ar$^{3c}$—Ar$^{3d}$—H (1-l-4);

and the structure when l is 5 is represented by —Ar$^{3a}$—Ar$^{3b}$—Ar$^{3c}$—Ar$^{3d}$—Ar$^{3e}$—H (1-l-5).

Structures of (—[Ar$^4$]$_p$—H) when p takes an integer value of 1 to 5 are represented by the following formulae (1-p-1) to (1-p-5) respectively:

the structure when p is 1 is represented by —Ar$^{4a}$—H (1-p-1);

the structure when p is 2 is represented by —Ar$^{4a}$—Ar$^{4b}$—H (1-p-2);

the structure when p is 3 is represented by —Ar$^{4a}$—Ar$^{4b}$—Ar$^{4c}$—H (1-p-3);

the structure when p is 4 is represented by —Ar$^{4a}$—Ar$^{4b}$—Ar$^{4c}$—Ar$^{4d}$—H (1-p-4);

and the structure when p is 5 is represented by —Ar$^{4a}$—Ar$^{4b}$—Ar$^{4c}$—Ar$^{4d}$—Ar$^{4e}$—H (1-p-5).

In the formulae (1-n-1) to (1-n-5), Ar$^{1a}$, Ar$^{1b}$, Ar$^{1c}$, Ar$^{1d}$ and Ar$^{1e}$ may be mutually the same or different. In the formulae (1-m-1) to (1-m-5), Ar$^{2a}$, Ar$^{2b}$, Ar$^{2c}$, Ar$^{2d}$ and Ar$^{2e}$ may be mutually the same or different. In the formulae (1-l-1) to (1-l-5), Ar$^{3a}$, Ar$^{3b}$, Ar$^{3c}$, Ar$^{3d}$ and Ar$^{3e}$ may be mutually the same or different. In the formulae (1-p-1) to (1-p-5), Ar$^{4a}$, Ar$^{4b}$, Ar$^{4c}$, Ar$^{4d}$ and Ar$^{4e}$ may be mutually the same or different.

When the naphthalene derivative has a structure in which two naphthalene skeletons are consecutively bonded together, the structure of the naphthalene derivative is represented by any one of formulae (1-A), (1-B), (1-C) and (1-D) as follows;

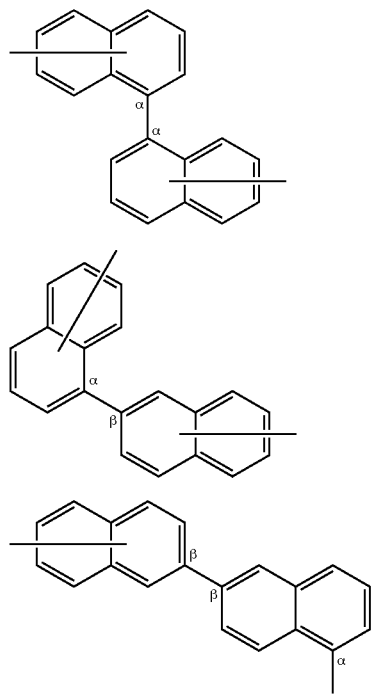

(1-A)

(1-B)

(1-C)

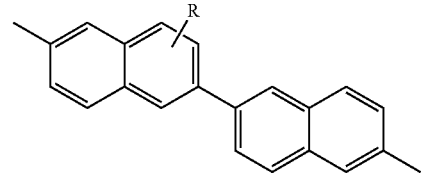

(1-D)

The naphthalene skeletons represented by the formulae (1-A), (1-B) and (1-C) each may have a substituent(s) in any suitable position(s) or may be unsubstituted.

R in the formula (1-D) represents a substituent. R may represent a single substituent or plural substituents. The substituent(s) may be in any position(s) of the two naphthalene skeletons; when R represents the plural substituents, the plural substituents may be mutually the same or different.

When the naphthalene derivative has a structure in which three naphthalene skeletons are consecutively bonded together, a naphthalene skeleton of the three naphthalene skeletons that is positioned at the center of the structure is tetravalent or more while at least either one of the other naphthalene skeletons of the three naphthalene skeletons that are positioned at ends of the structure is trivalent or more.

When the naphthalene derivative has a structure in which four naphthalene skeletons are consecutively bonded together, at least one of the naphthalene skeletons is tetravalent or more.

When the naphthalene derivative contains a plurality of unsubstituted 9-phenanthrenes, the number of the unsubstituted 9-phenanthrenes is 3 or more.

In the naphthalene derivative, when Ar$^1$ to Ar$^4$ each represent a phenanthrene skeleton, the phenanthrene skeleton is monovalent.

In the present invention, "carbon atoms forming a ring" means carbon atoms for forming a saturated ring, an unsaturated ring or an aromatic ring. On the other hand, "atoms forming a ring" means carbon atoms and heteroatoms for forming a heterocycle (including a saturated ring, an unsaturated ring and an aromatic ring).

An organic compound having an anthracene skeleton, a pyrene skeleton, an aceanthrylene skeleton or an naphthacene skeleton is not preferable because such an organic compound generates less triplet exciton energy and because a phosphorescent organic EL device in which such an organic compound is used can hardly emit light efficiently. Thus, it is not preferable that Ar$^1$ and Ar$^2$ each have any one of the structures listed above.

In addition, since less triplet exciton energy is generated when Ar$^1$ and Ar$^2$ each contain more than 18 carbon atoms, a phosphorescent organic EL device in which such a naphthalene derivative is used can hardly emit light efficiently.

When m and n each are more than 4, a molecular weight of the naphthalene derivative becomes so large that the naphthalene derivative can hardly be vapor-deposited. Thus, m and n each are preferably in a range of 1 to 4.

Compounds in each of which two or more naphthalene skeletons are consecutively bonded together in β positions and compounds each having a highly-symmetrical structure exhibit such high crystallinity that the compounds can hardly maintain high amorphousness when being formed into thin film(s).

As a solution, for instance, by:
(1) introducing torsional portion(s) into the molecule with the naphthalene skeletons being bonded together in α positions;
(2) introducing substituent(s) having steric hindrance; and/or (3) asymmetrically shaping the molecule, crystallization of the compounds can be prevented, such that thin film(s) of high amorphousness can be formed.

According to the present invention, when the naphthalene derivative is structured such that two naphthalene skeletons are consecutively bonded together, the naphthalene skeletons are bonded together in a positions as represented by the formula (1-A), (1-B) or (1-C), so that the torsional portion prevents the crystallization of the naphthalene derivative.

According further to the present invention, when two naphthalene skeletons are bonded together in β positions, substituent(s) R are contained as represented by the formula (1-D), such that steric hindrance of the substituent(s) R can prevent the crystallization of the naphthalene derivative.

Likewise, when the naphthalene derivative has a structure in which three naphthalene skeletons are consecutively bonded together, a naphthalene skeleton positioned at the center of the structure is tetravalent or more while at least either one of the other naphthalene skeletons positioned at ends of the structure is trivalent or more, such that the substituent(s) can prevent the crystallization of the naphthalene derivative.

When the naphthalene derivative has a structure in which four naphthalene skeletons are consecutively bonded together, at least one of the naphthalene skeletons is tetravalent or more, such that steric hindrance of the substituent(s) can prevent the crystallization of the naphthalene derivative.

As described above, according to the present invention, the crystallization of the compound within the layer of the organic EL device can be prevented by a combination of asymmetrically forming the molecule and introducing torsional position(s) in the molecule. The prevention of the crystallization of the compound within the layer is indispensable for solving a problem(s).

When the naphthalene derivative contains a plurality of unsubstituted 9-phenanthrenes as substituents, the number of the unsubstituted 9-phenanthrenes is 3 or more. Thus, by introducing a plurality of partial structures each having a relatively large molecular weight, heat resistance can be enhanced.

Only a material that satisfies all of the above-described conditions can be favorably applied as a material for forming an organic EL device that is free from pixel defects and excellent in luminous efficiency, heat resistance and lifetime.

In the formula (1), $Ar^1$ to $Ar^4$ each preferably represent a benzene skeleton, a naphthalene skeleton, a fluorene skeleton, a phenanthrene skeleton, a fluoranthene skeleton, a triphenylene skeleton or a chrysene skeleton. Among the above, a benzene skeleton, a naphthalene skeleton, a fluorene skeleton and a phenanthrene skeleton are preferable.

When n, m, l and p each are 2 or more, a plurality of $Ar^1$ to $Ar^4$ may be mutually the same or different. In the above case, a preferable example of the plurality of $Ar^1$ to $Ar^4$ is a combination of a benzene skeleton and a naphthalene skeleton.

When the above substituents are applied to $Ar^1$ to $Ar^4$, triplet energy can be sufficiently conserved in the organic EL device where the substituents and a phosphorescent material are used together.

It should be noted that a "fluorescent host" and a "phosphorescent host" herein respectively mean a host combined with a fluorescent dopant and a host combined with a phosphorescent dopant, and that a distinction between the fluorescent host and phosphorescent host is not unambiguously derived only from a molecular structure of the host in a limited manner.

In other words, the fluorescent host herein means a material for forming fluorescent-emitting layer containing a fluorescent dopant, and does not mean a host that is only usable as a host of a fluorescent material.

Likewise, the phosphorescent host herein means a material for forming phosphorescent-emitting layer containing a phosphorescent dopant, and does not mean a host that is only usable as a host of a phosphorescent material.

When $Ar^1$ to $Ar^4$ in the formula (1) each has a substituent, preferable examples of the substituent are an aryl group having 6 to 30 carbon atoms, an alkyl group having 1 to 30 carbon atoms, a cycloalkyl group having 3 to 30 carbon atoms, an alkoxy group having 1 to 20 carbon atoms, a cyano group, a silyl group having 3 to 30 carbon atoms and a halogen atom.

Examples of the aryl group having 6 to 30 carbon atoms are a phenyl group, 1-naphthyl group, 2-naphthyl group, 1-phenanthryl group, 2-phenanthryl group, 3-phenanthryl group, 4-phenanthryl group, 9-phenanthryl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, and 4"-t-butyl-p-terphenyl-4-yl group.

Preferable examples of the alkyl group having 1 to 30 carbon atoms are a methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group and 1,2,3-trinitropropyl group.

Examples of the cycloalkyl group having 3 to 30 carbon atoms are cyclopentyl group, cyclohexyl group, cyclooctyl group, and 3,5-tetramethylcyclohexyl group, among which cyclohexyl group, cyclooctyl group and 3,5-tetramethylcyclohexyl group are preferable.

The alkoxy group having 1 to 20 carbon atoms is a group represented by —OY. Examples of Y are a methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3- trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group and 1,2,3-trinitropropyl group.

The alkylsilyl group having 3 to 30 carbon atoms is preferably an arylsilyl group or an aralkylsilyl group, examples of which are trimethylsilyl group, triethylsilyl group, tributylsilyl group, trioctylsilyl group, triisobutylsilyl group, dimethylethylsilyl group, dimethylisopropylsilyl group, dimethylpropylsilyl group, dimethylbutylsilyl group, dimethyltertiarybutylsilyl group, diethylisopropylsilyl group, phenyldimethylsilyl group, diphenylmethylsilyl group, diphenyltertiarybutyl group and triphenylsilyl group.

Examples of the halogen atom are fluorine, chlorine, bromine, iodine and the like.

R in the formula (1-D) preferably represents, for instance, an alkyl group having 1 to 30 carbon atoms, a cycloalkyl group having 6 to 30 carbon atoms, an alkoxy group having 1 to 20 carbon atoms, a cyano group, a silyl group having 3 to 30 carbon atoms or a halogen atom. Examples of the alkyl group, the alkoxy group, the cyano group, the silyl group and the halogen atom may be the same as the above examples of the substituent for $Ar^1$ to $Ar^4$.

In the formula (1), n, m, and l each preferably represent an integer in a range of 1 to 3 while p preferably represents an integer in a range of 0 to 3.

When n, m, l and p are more than 3 in the formula (1), a molecular weight of the naphthalene derivative becomes so large that manufacturability of the organic EL device when the organic EL device is manufactured using an vapor deposition unit may be deteriorated. More preferably, n, m, l and p each represent 1 or 2.

When the naphthalene derivative has a structure in which two naphthalene skeletons are consecutively bonded together, the structure of the naphthalene derivative is represented by any one of the following formulae (1-A), (1-B), (1-C) and (1-D), among which the structure is preferably represented by the formula (1-B) or the formula (1-C).

Examples of the naphthalene derivative according to the present invention are as follows.

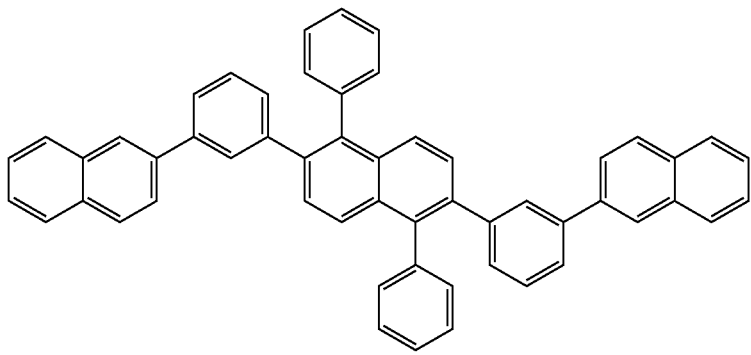

1-1

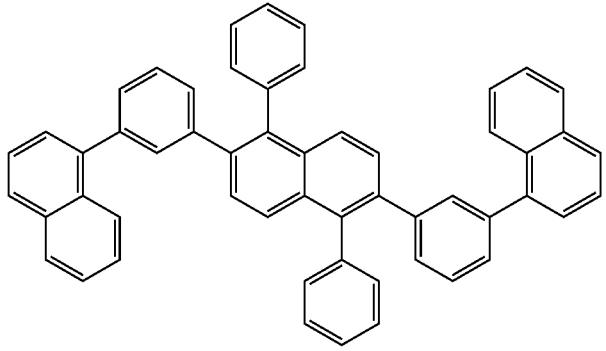

1-2

1-3
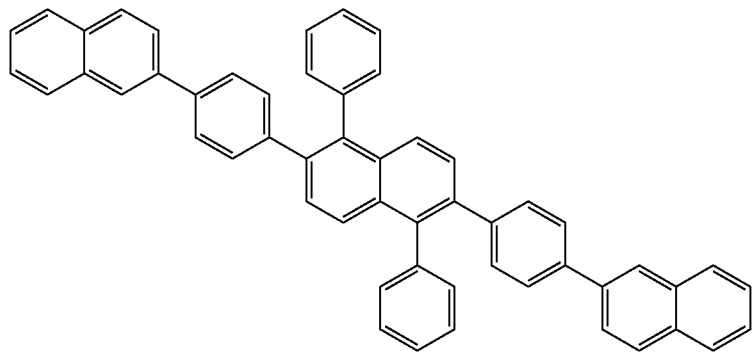
1-4
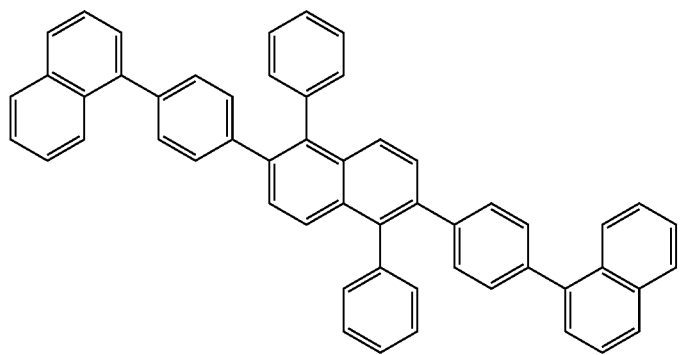
1-5
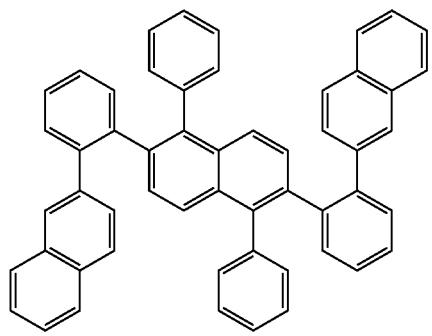
1-6
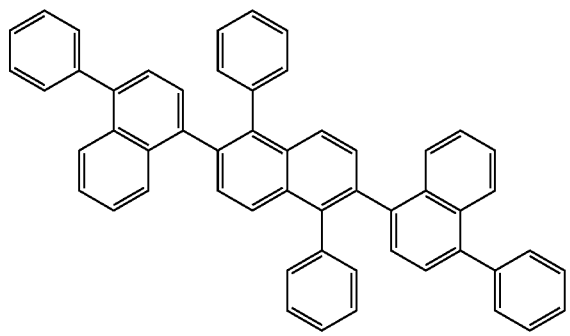
1-7
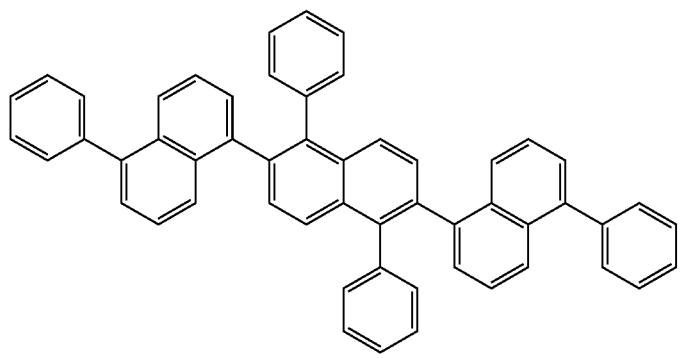

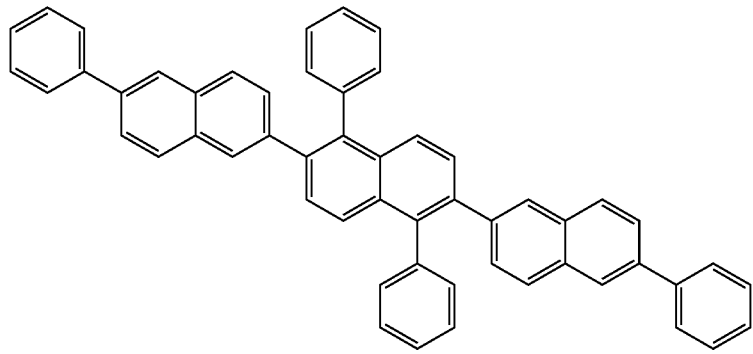
1-8
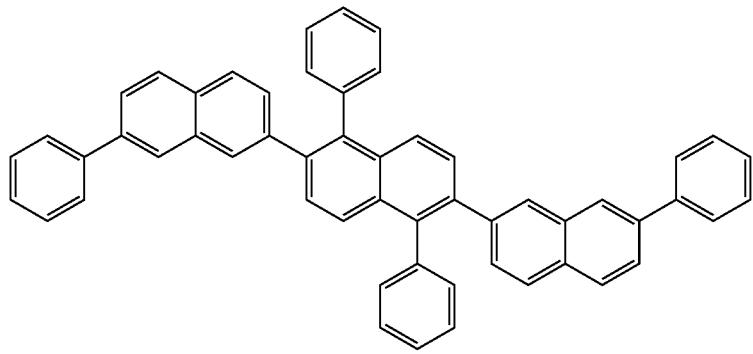
1-9
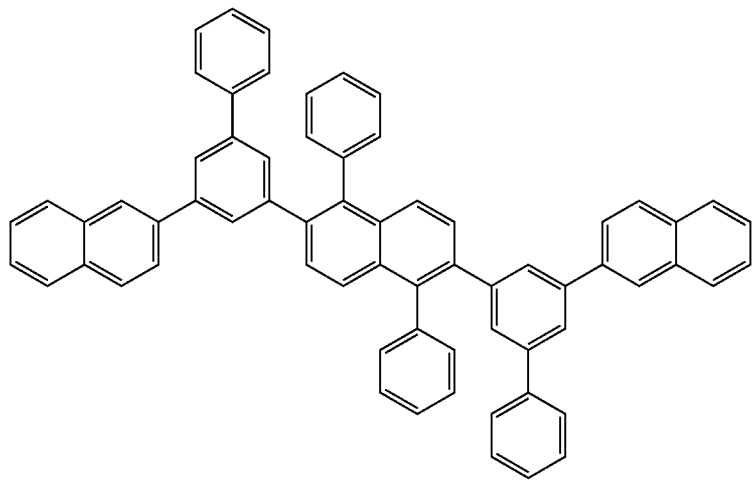
1-10
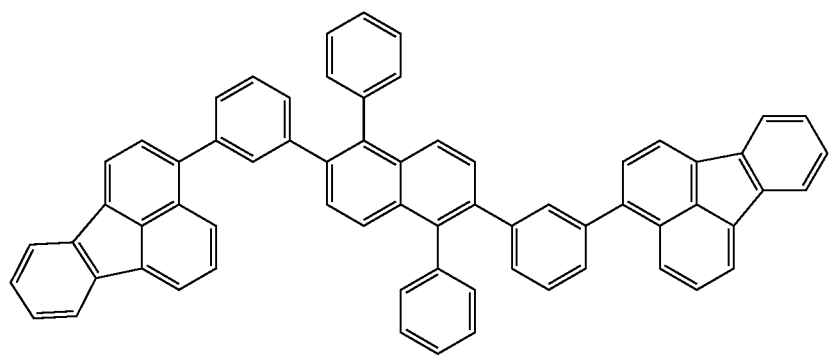
1-11

1-12
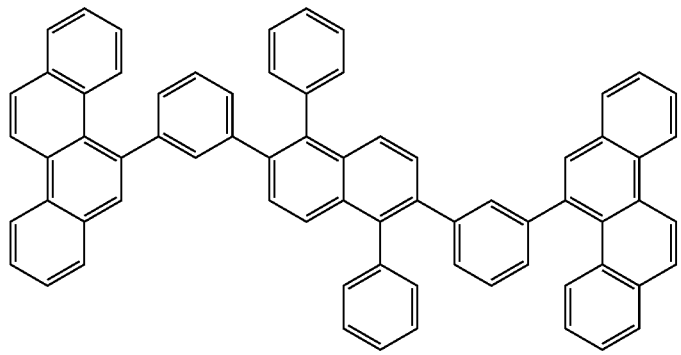
1-13
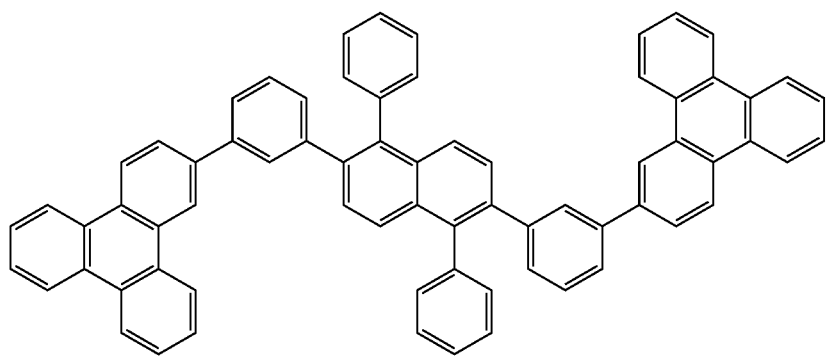
1-14
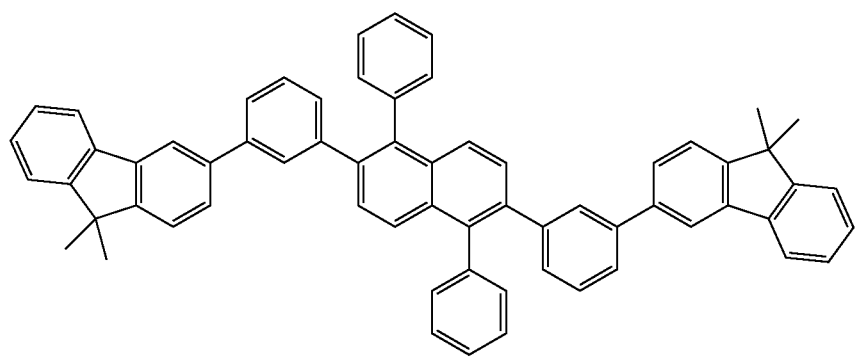
1-15
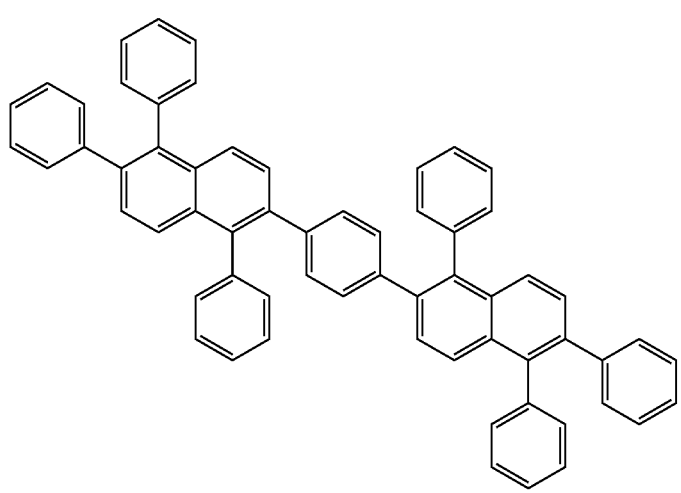

1-16
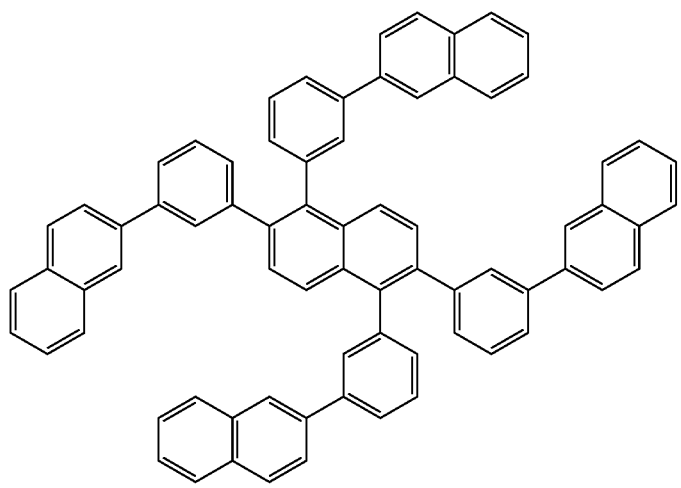
1-17
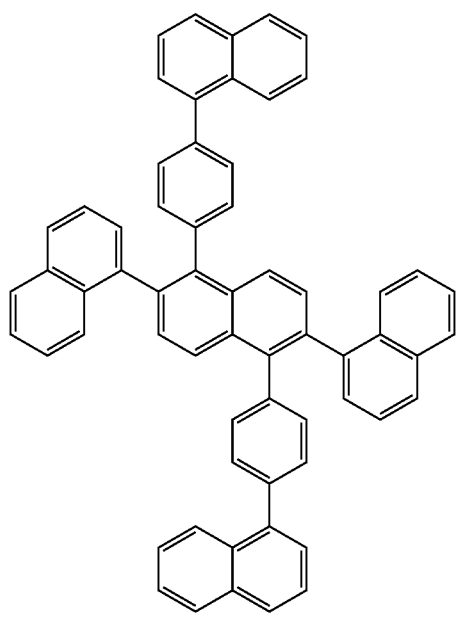
1-18
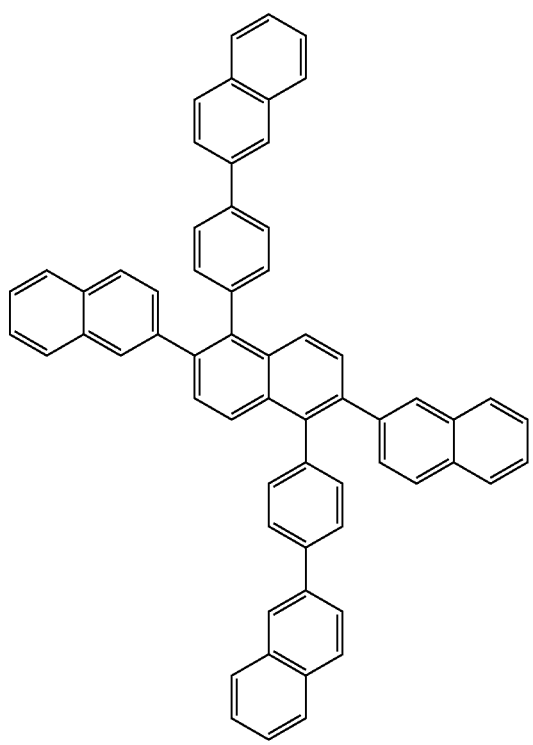

1-19
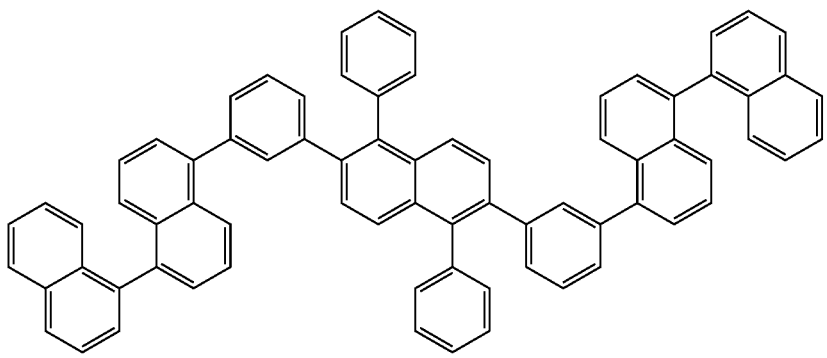
1-20
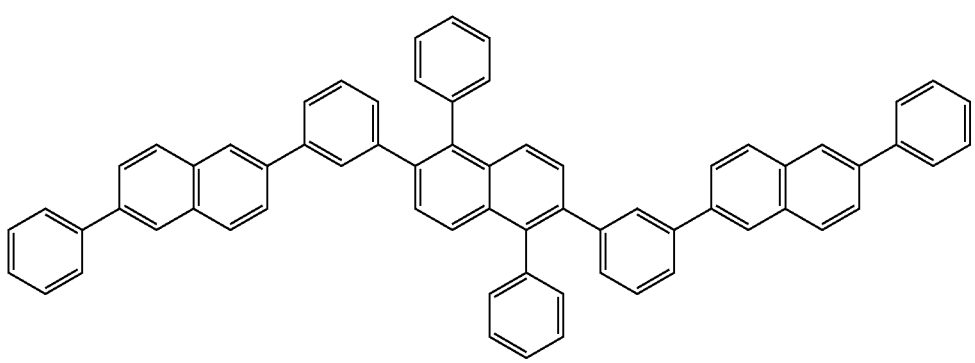
1-21
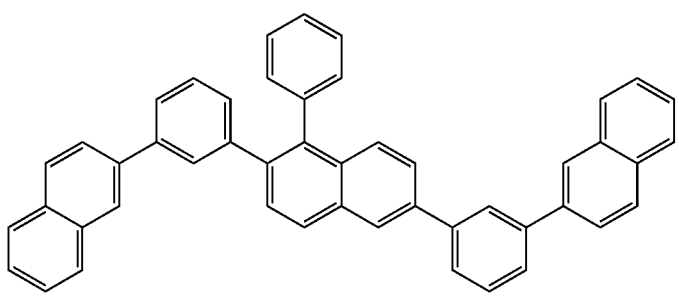
1-22
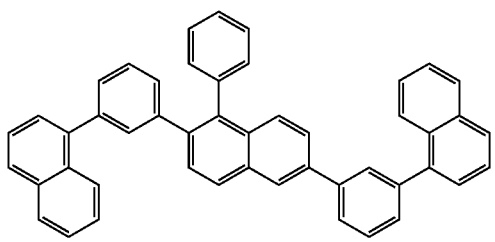
1-23
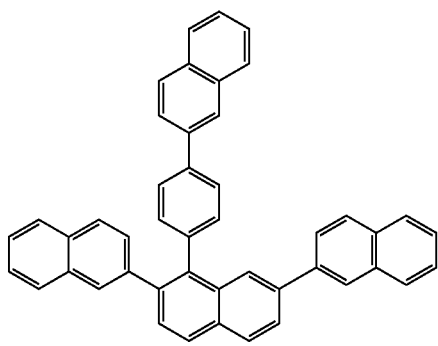

-continued
1-24
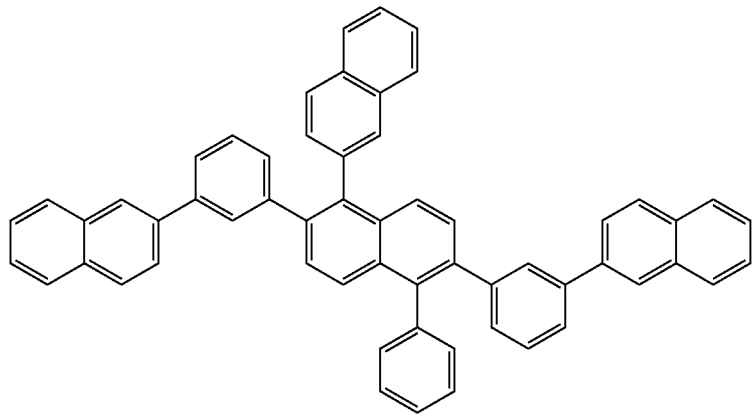
1-25
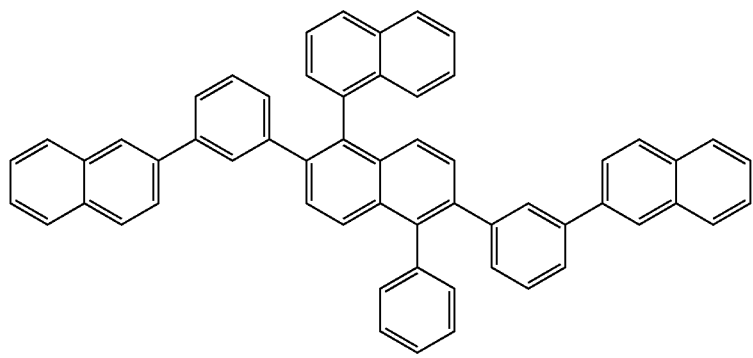
1-26
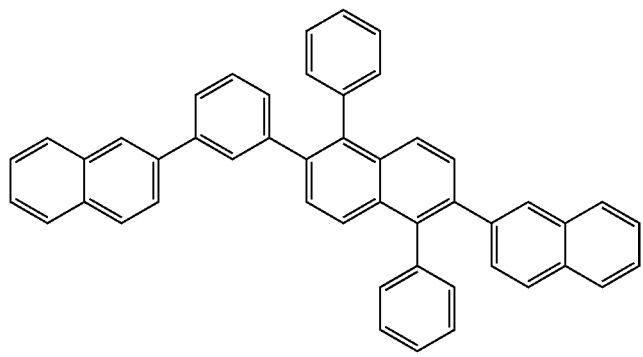
1-27
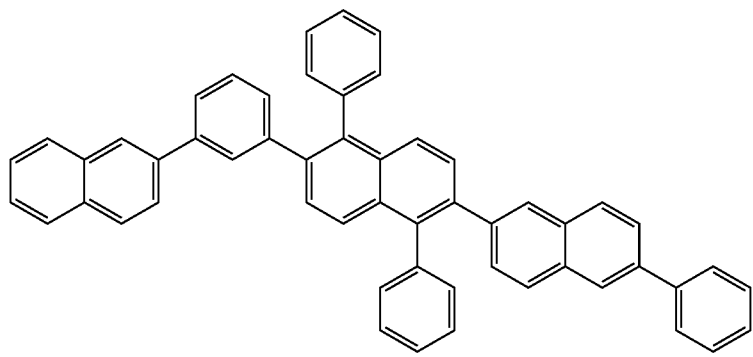

-continued
1-28
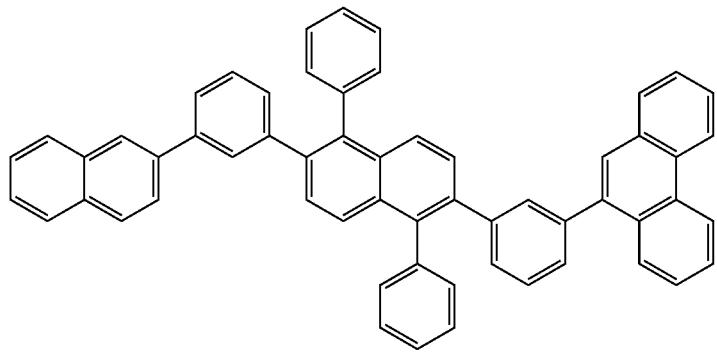
1-29
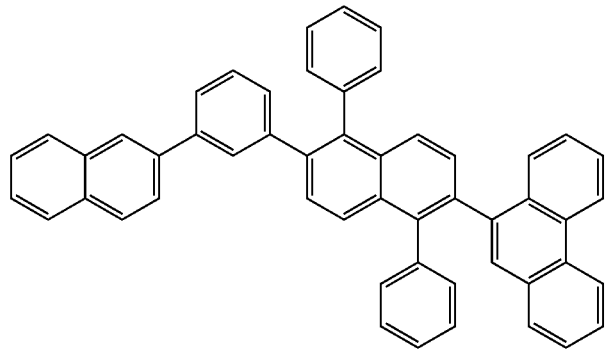
1-30
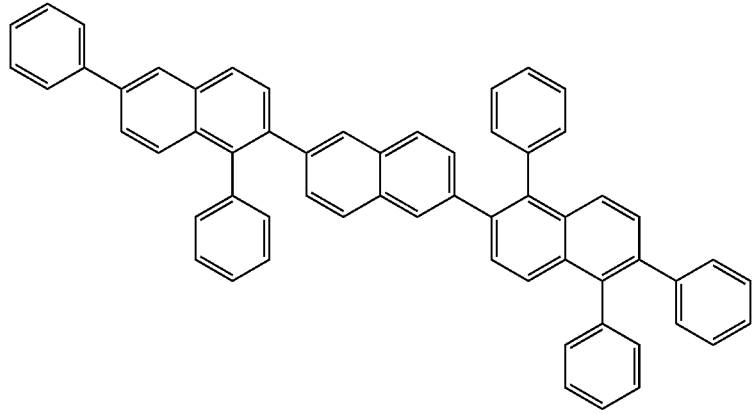
1-31
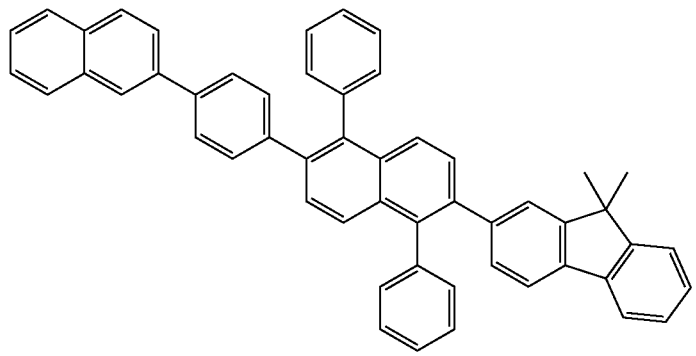

-continued
1-32
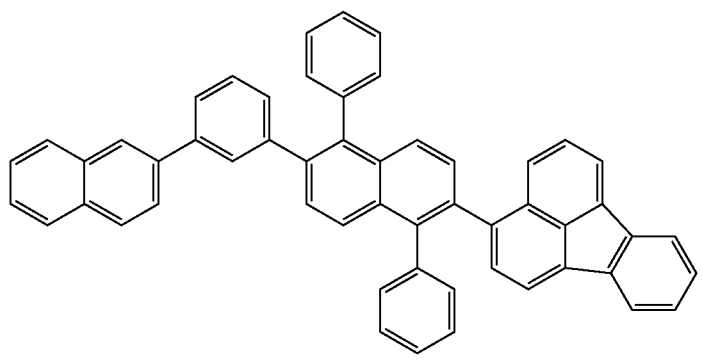
1-33
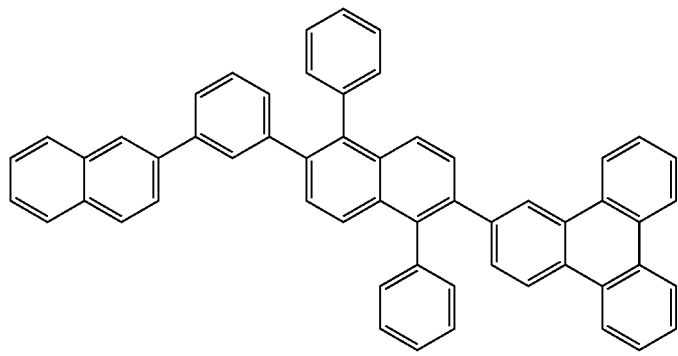
1-34
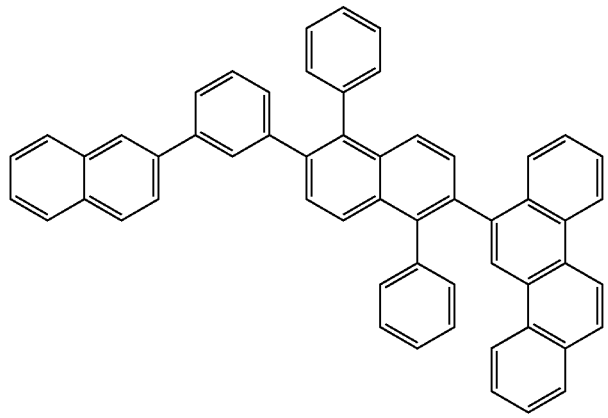
1-35
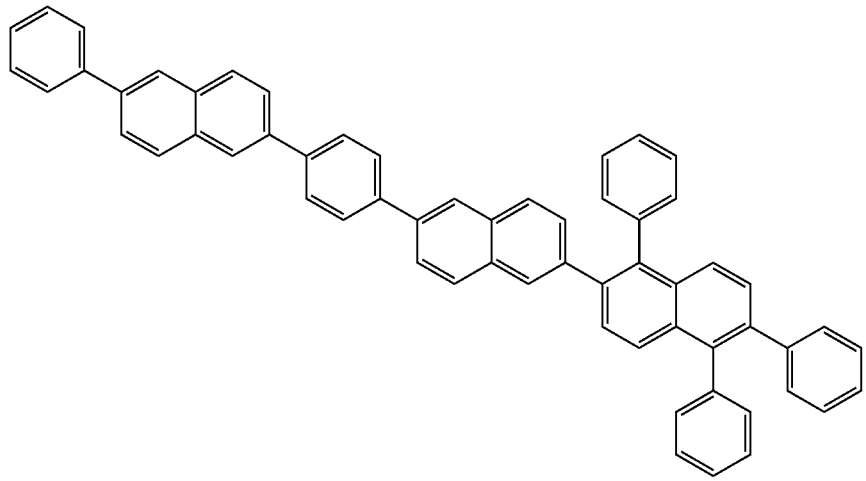

-continued
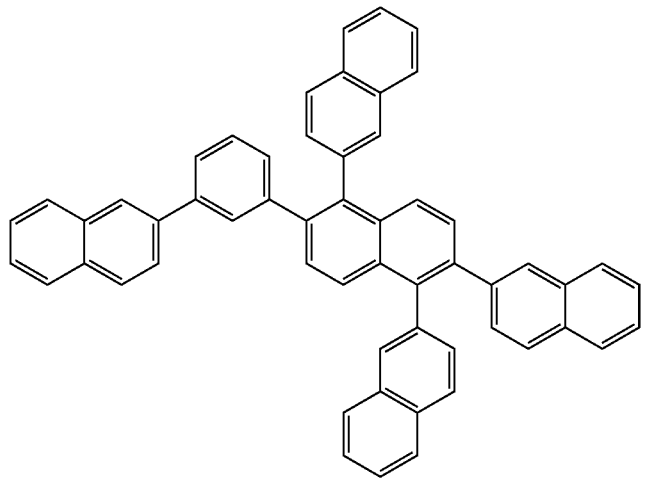
1-36
1-37
1-38

1-39
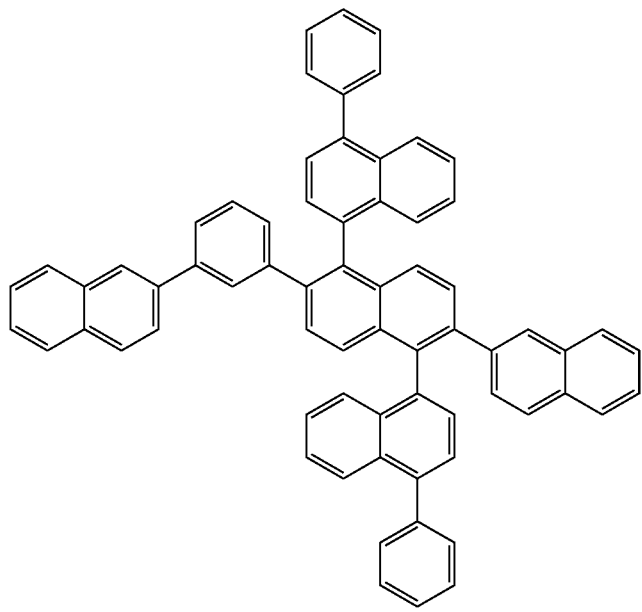
1-40
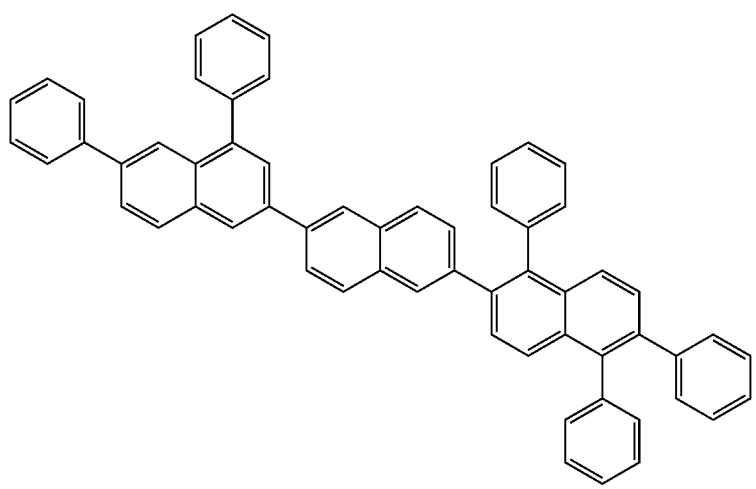
1-41
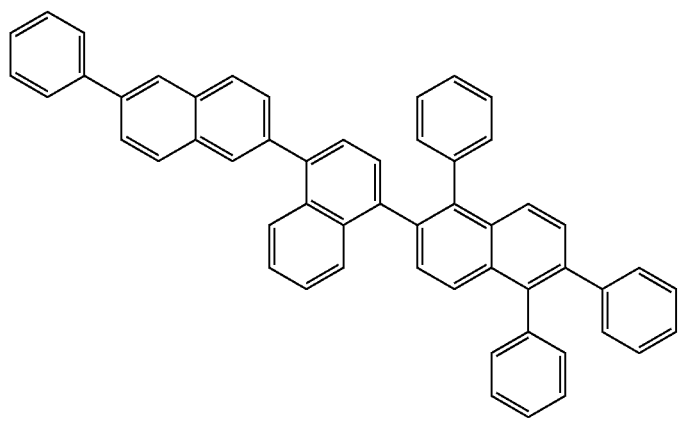

-continued
1-42
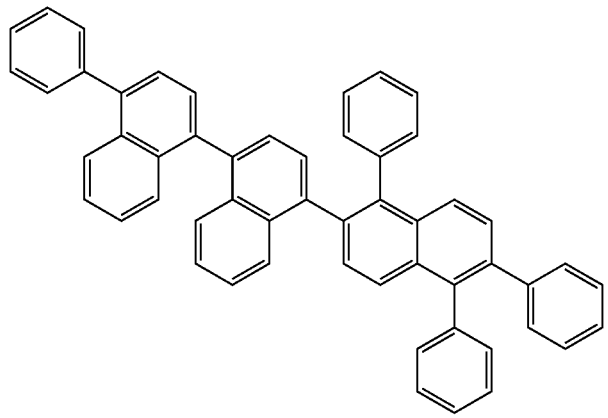
1-43
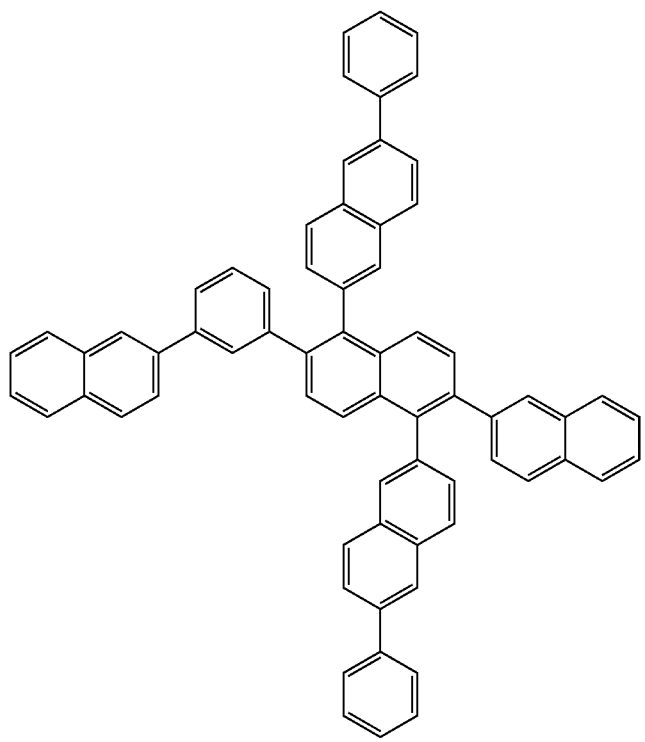
1-44
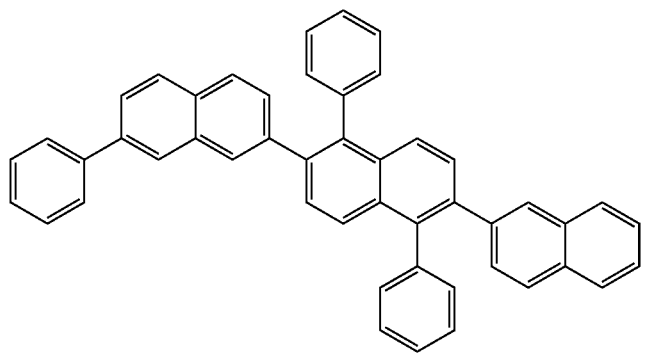

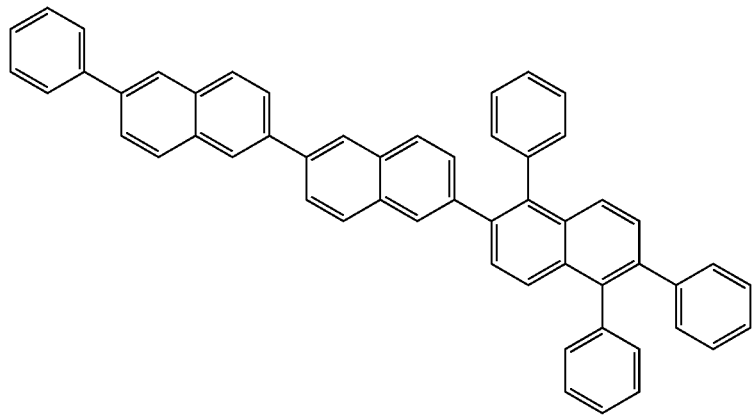
1-45
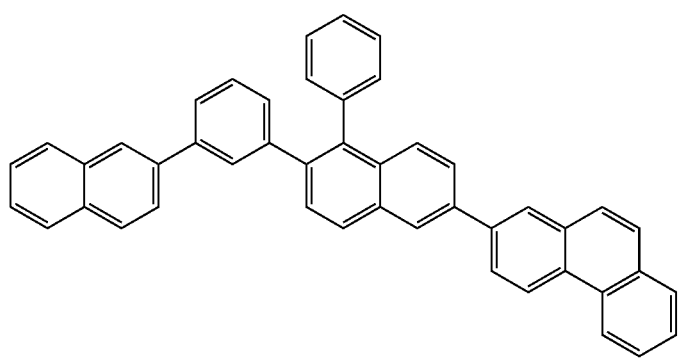
1-46
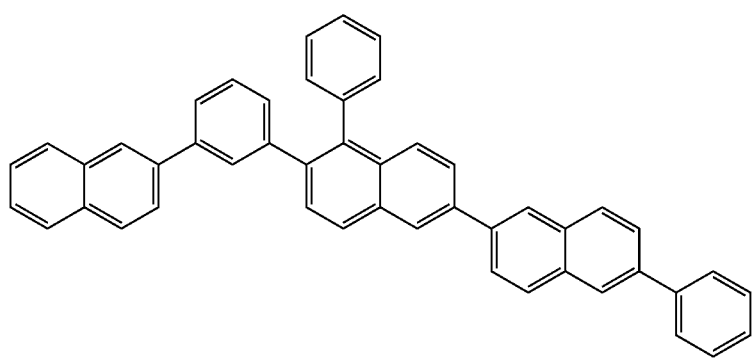
1-47

-continued
1-48
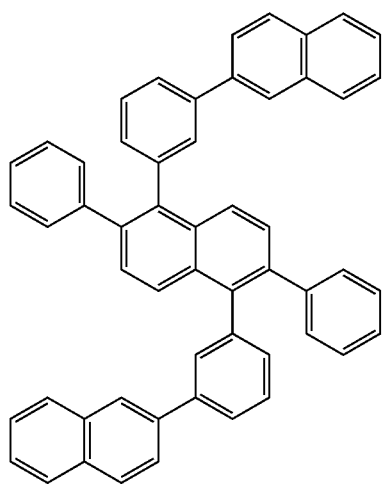
1-49
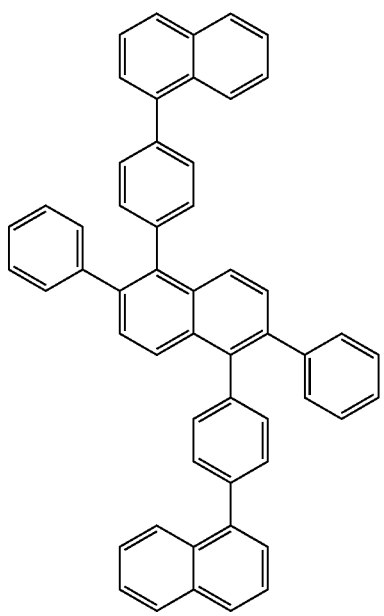
1-50
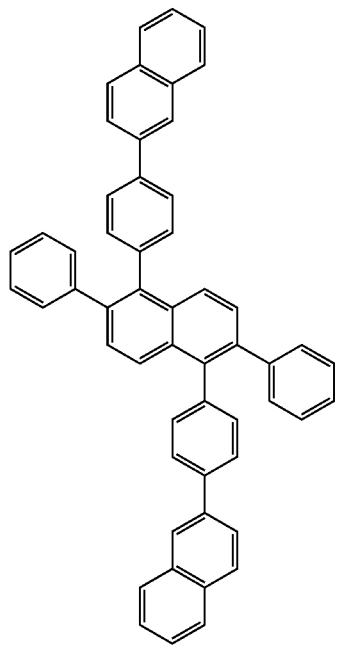
1-51
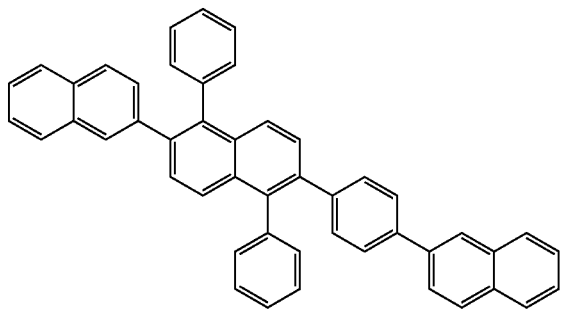
1-52
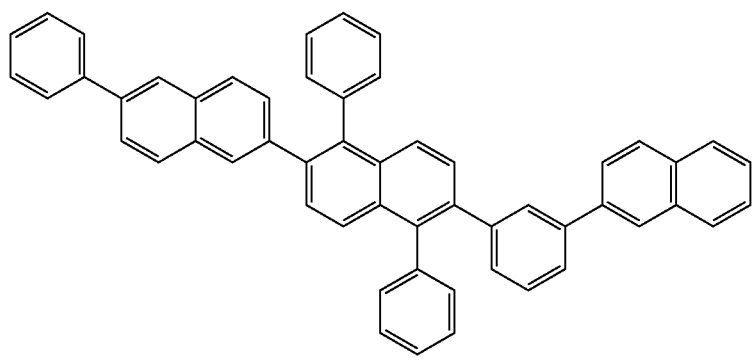

-continued
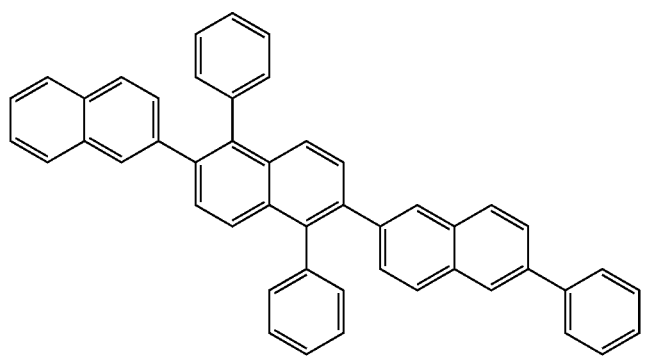
1-53
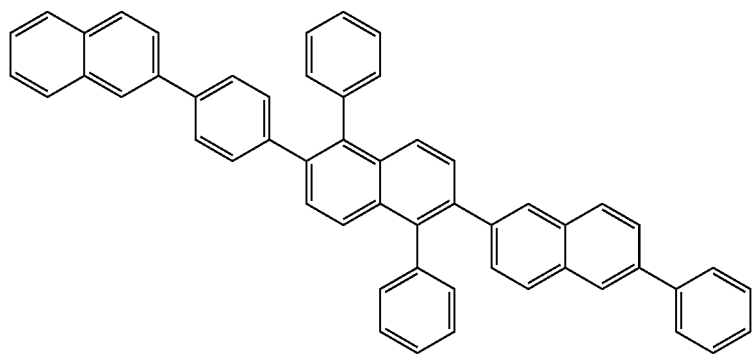
1-54
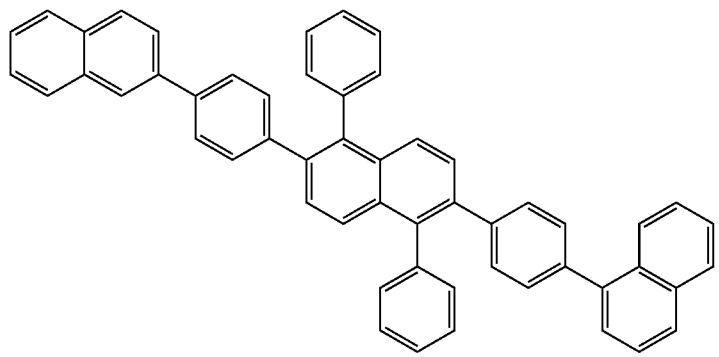
1-55
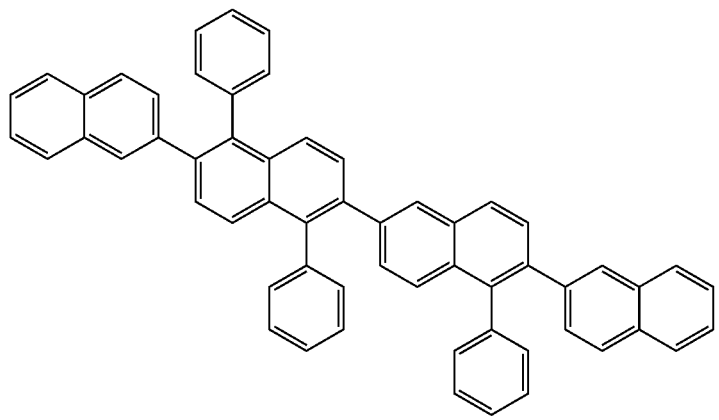
1-56

1-57
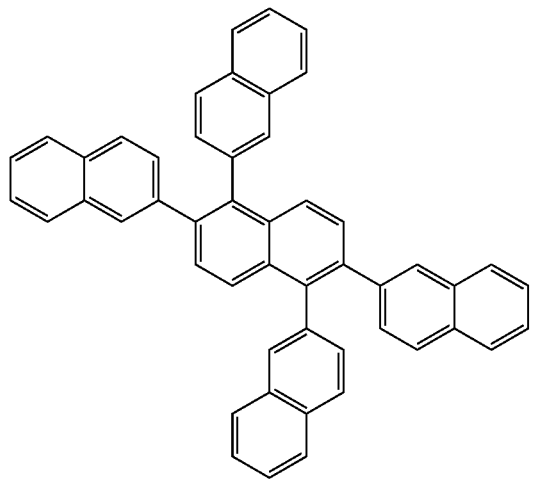
1-58
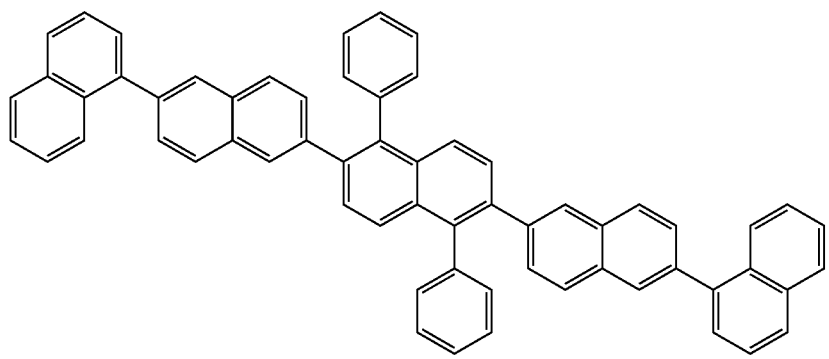
1-59
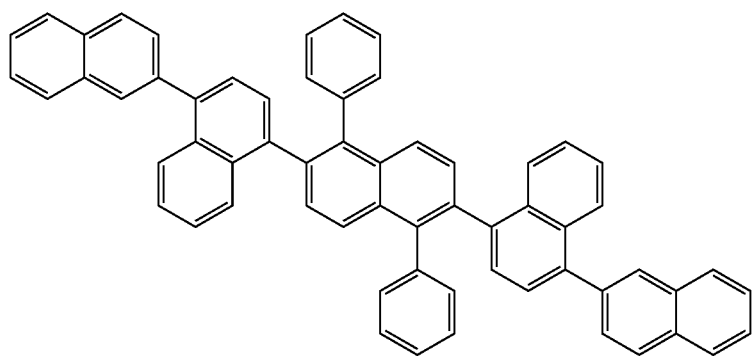

-continued 1-60

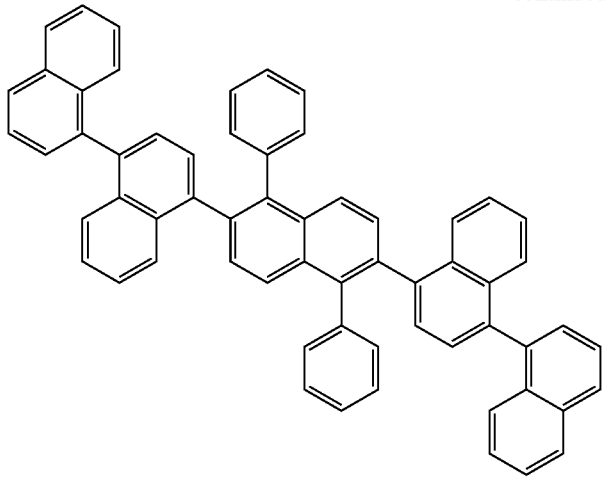

[Material for Organic EL Device]

A material for an organic EL device according another aspect of the present invention contains the naphthalene derivative represented by the formula (1).

The material for an organic EL device according to the aspect of the present invention is preferably used as a host material of an emitting layer.

By using the material containing the naphthalene derivative represented by the formula (1) as the host material of the emitting layer, the emitting layer can exhibit high efficiency and long lifetime.

[Organic EL Device]

Next, an organic EL device according to still further aspect of the present invention will be described.

An organic EL device according to still further aspect of the present invention includes: a cathode; an anode; and an organic thin-film layer provided between the cathode and the anode. The organic thin-film layer includes at least one layer, and the at least one layer of the organic thin-film layer includes an emitting layer. The at least one layer of the organic thin-film layer contains the material for an organic EL device according to the present invention.

A multilayer organic EL device may be exemplarily structured as anode/hole transporting layer (hole injecting layer)/emitting layer/cathode, anode/emitting layer/electron transporting layer (electron injecting layer)/cathode, anode/hole transporting layer (hole injecting layer)/emitting layer/electron transporting layer (electron injecting layer)/cathode, or anode/hole transporting layer (hole injecting layer)/emitting layer/hole blocking layer/electron transporting layer (electron injecting layer)/cathode.

FIG. 1 schematically shows an arrangement of an exemplary organic EL device according to the present invention.

An organic EL device 1 includes a transparent substrate 2, an anode 3, a cathode 4 and an organic thin-film layer 10 disposed between the anode 3 and the cathode 4.

The organic thin-film layer 10 includes a phosphorescent emitting layer 5 containing a host and a phosphorescent dopant. A layer such as a hole injecting/transporting layer 6 may be provided between the phosphorescent emitting layer 5 and the anode 3 while a layer such as an electron injecting/transporting layer 7 may be provided between the phosphorescent emitting layer 5 and the cathode 4.

In addition, an electron blocking layer may be provided to the phosphorescent emitting layer 5 adjacent to the anode 3 while a hole blocking layer may be provided to the phosphorescent emitting layer 5 adjacent to the cathode 4.

With this arrangement, electrons and holes can be confined in the phosphorescent emitting layer 5, thereby enhancing probability of exciton generation in the phosphorescent emitting layer 5.

It should be noted that the "hole injecting/transporting layer" herein means "at least one of hole injecting layer and hole transporting layer" while "electron injecting/transporting layer" herein means "at least one of electron injecting layer and electron transporting layer".

In the organic EL device according to the present invention, the emitting layer preferably contains the material for an organic EL device according to the present invention as the host material. In addition, the emitting layer is preferably formed of a host material and phosphorescent material while the host material is the material for an organic EL device according to the present invention.

An example of the phosphorescent material is a metal complex formed of a metal selected from a group consisting of Ir, Pt, Os, Au, Cu, Re and Ru and a ligand. The phosphorescent material is preferably a compound containing a metal selected from a group of iridium (Ir), osmium (Os) and platinum (Pt) because such a compound, which exhibits high phosphorescence quantum yield, can further enhance external quantum efficiency of the emitting device. The phosphorescent material is more preferably a metal complex such as an iridium complex, an osmium complex or a platinum complex, among which an iridium complex and a platinum complex are more preferable and ortho metalation of an iridium complex is the most preferable. More preferable examples of ortho metalation of a metal complex are iridium complexes as follows.

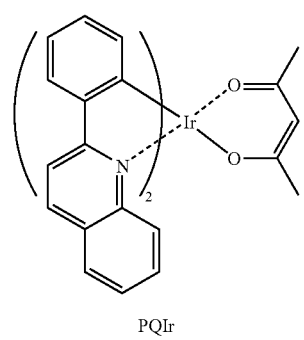

PQIr

-continued
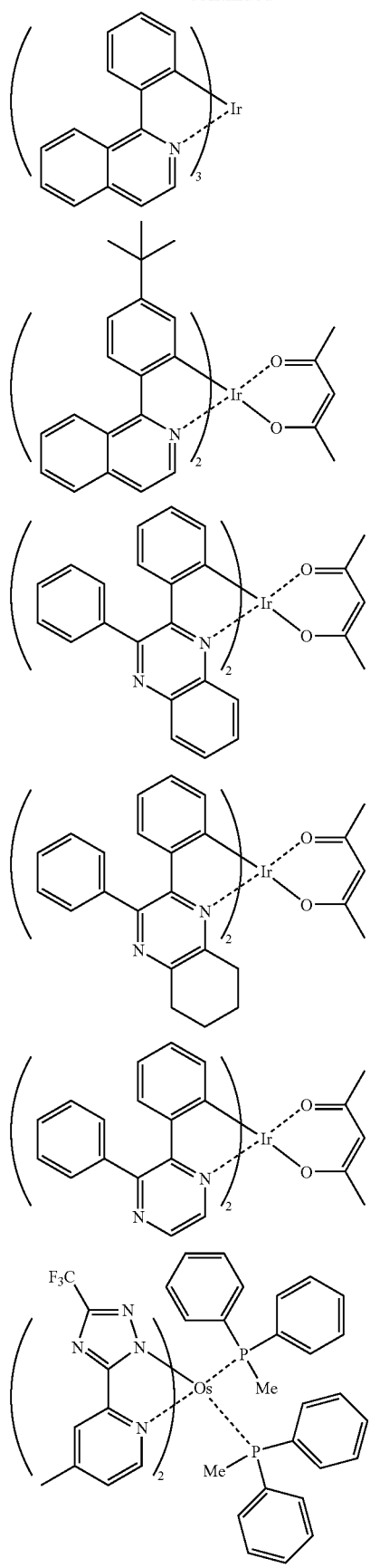
-continued
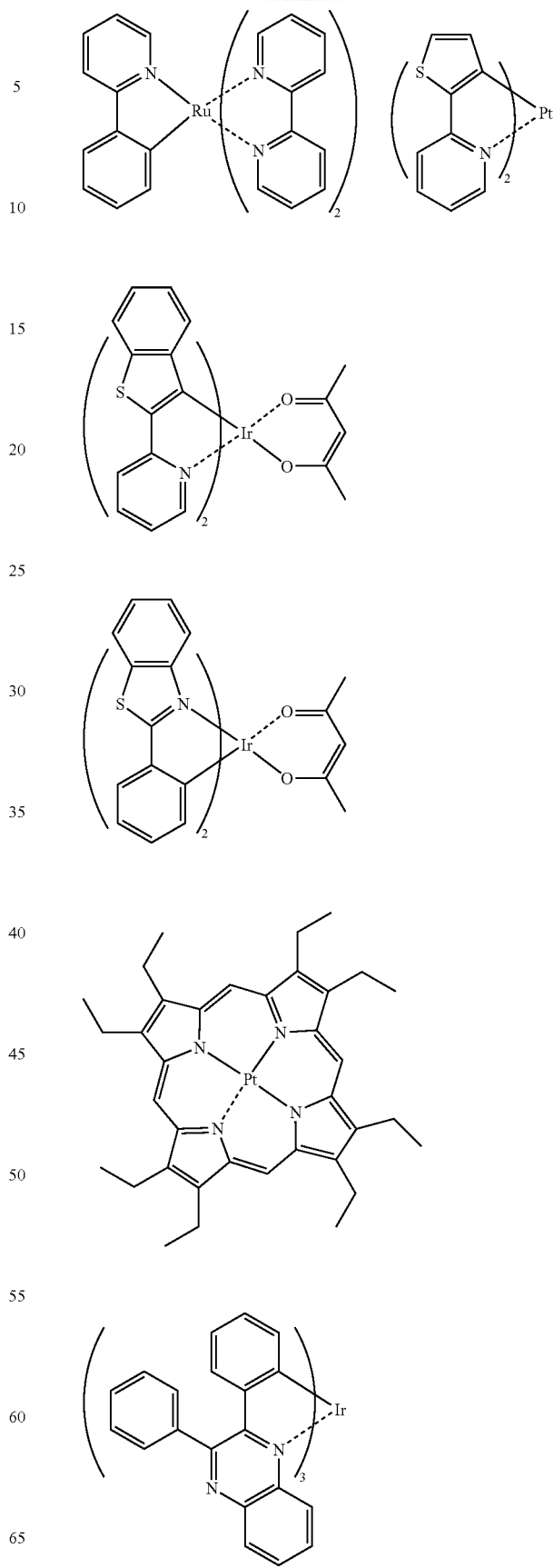

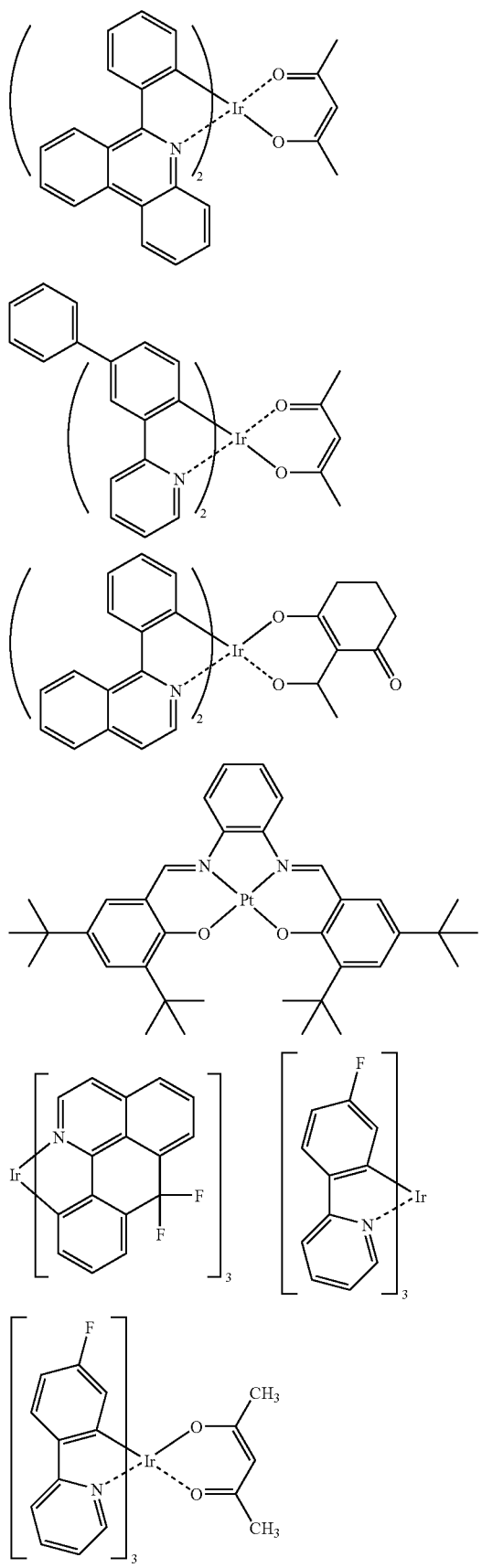
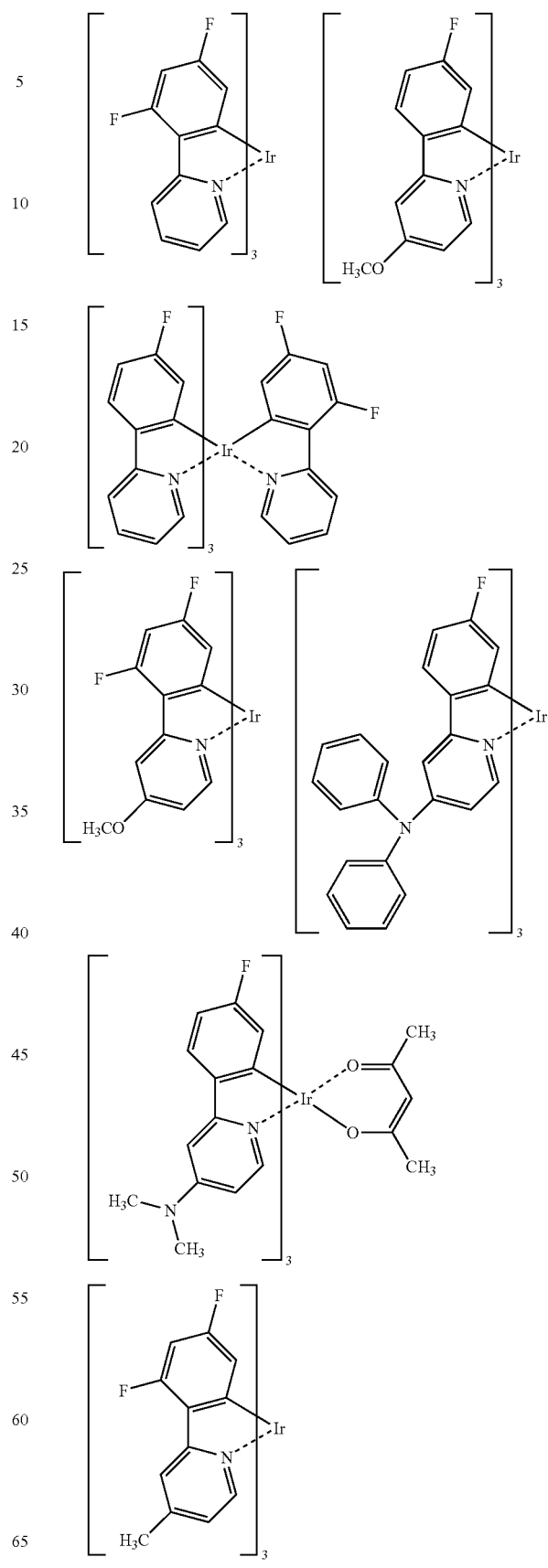

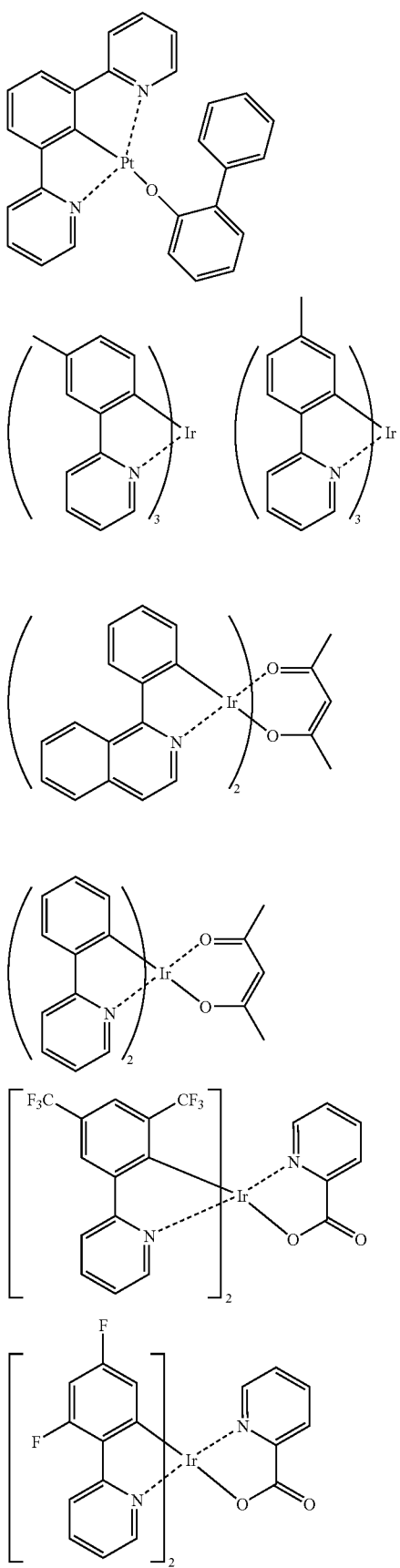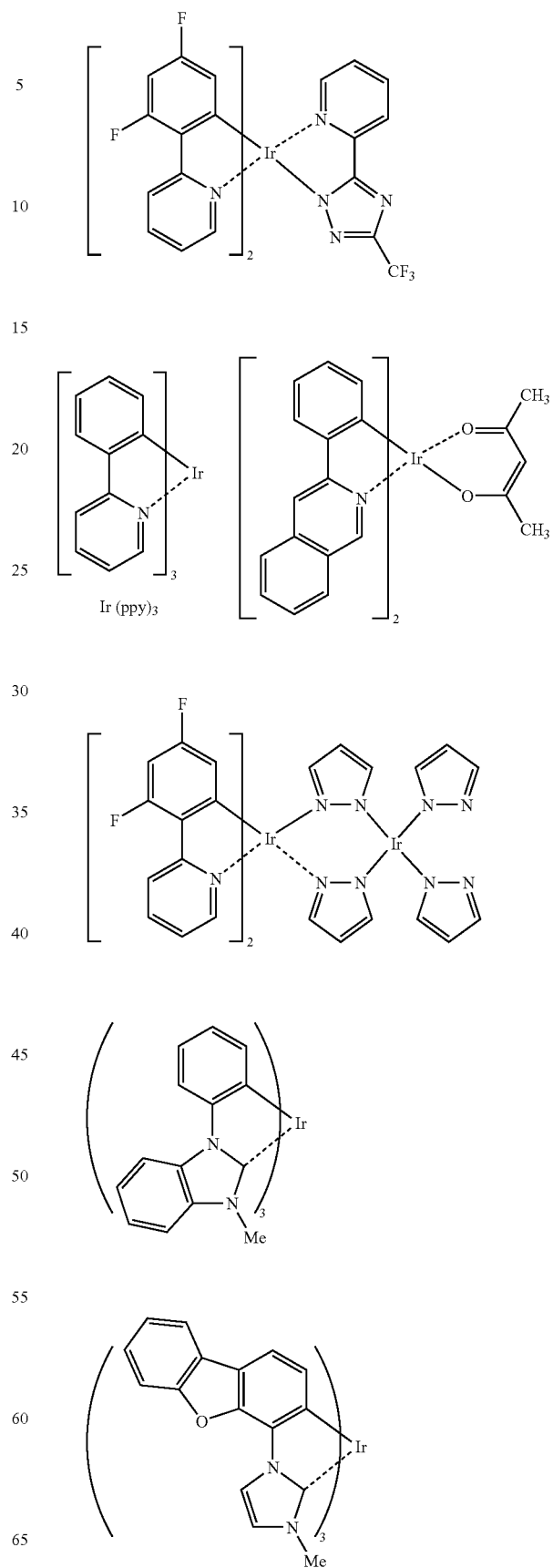
Ir (ppy)₃

-continued
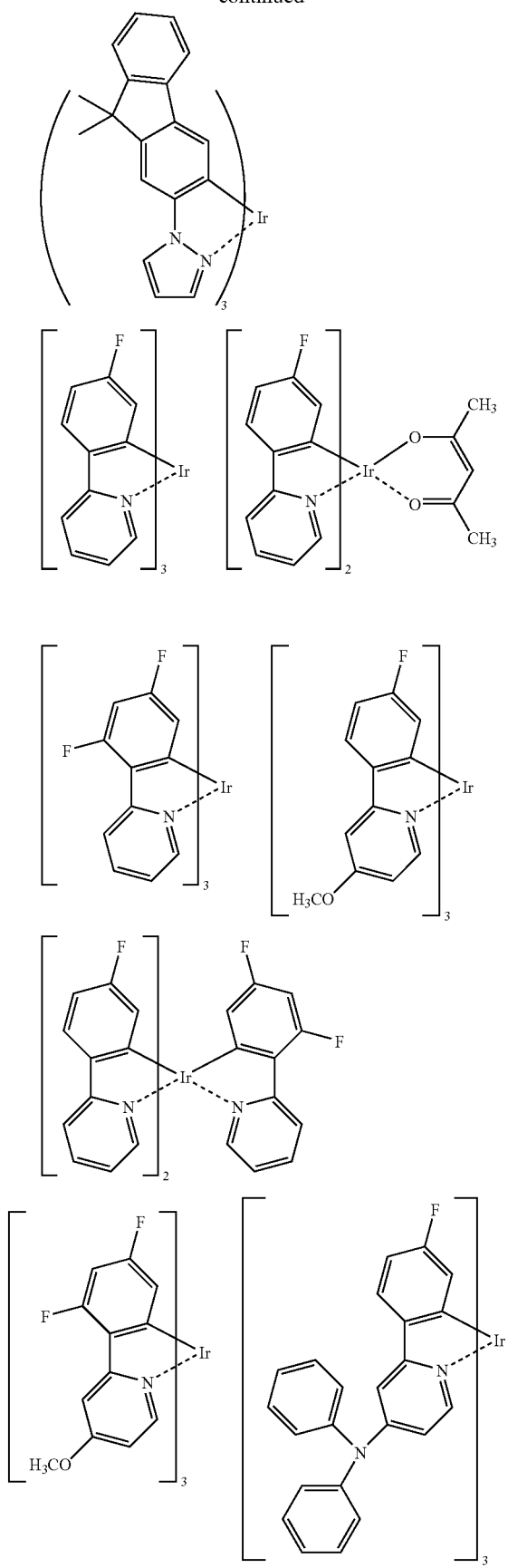
-continued
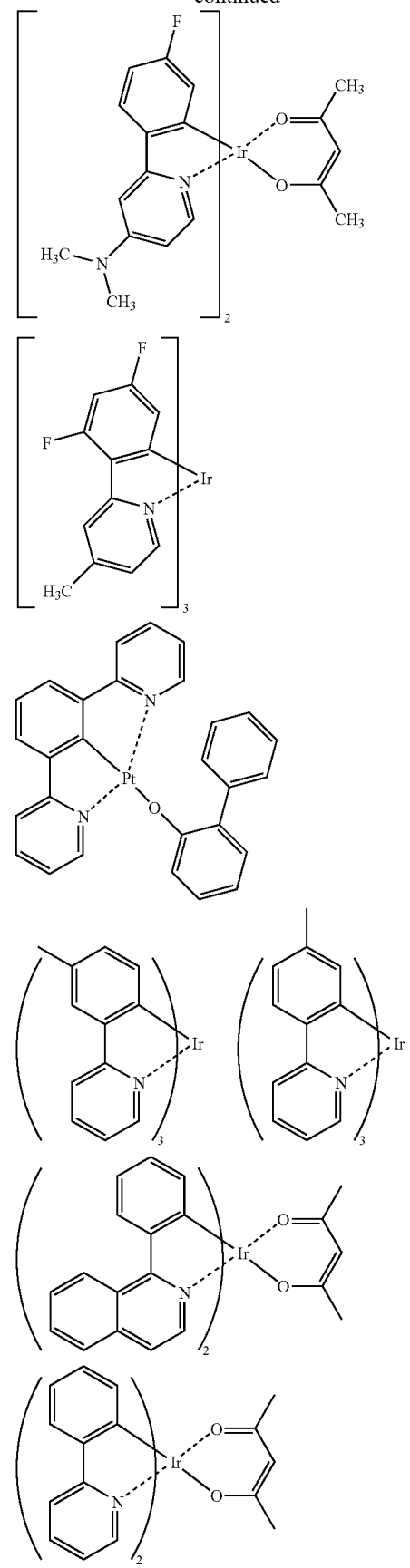

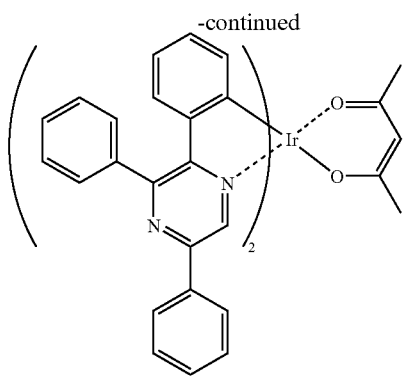

In the organic EL device according to the present invention, the emitting layer contains the host material and the phosphorescent material. Examples of the phosphorescent material are the compounds exemplified as the above-described iridium complexes.

According to the present invention, the phosphorescent material preferably emits light with maximum wavelength of 520 nm to 700 nm, more preferably 590 nm to 700 nm.

By doping the phosphorescent material (phosphorescent dopant) having such an emission wavelength to the material for an organic EL device according to the present invention so as to form the emitting layer, the organic EL device can exhibit high efficiency.

In the organic EL device according to the present invention, the hole transporting layer (or the hole injecting layer) included therein may contain the material for an organic EL device according to the present invention. Alternatively, when the organic EL device according to the present invention includes at least either one of the electron transporting layer and the hole blocking layer, at least either one of the electron transporting layer and the hole blocking layer may contain the material for an organic El device according to the present invention.

In the organic EL device according to the present invention, a reductive dopant may be contained in an interfacial region between the cathode and the organic thin-film layer.

With this arrangement, the organic EL device can emit light with enhanced luminance intensity and have a longer lifetime.

The reductive dopant may be at least one compound selected from a group of an alkali metal, an alkali metal complex, an alkali metal compound, an alkali earth metal, an alkali earth metal complex, an alkali earth metal compound, a rare-earth metal, a rare-earth metal complex, a rare-earth metal compound and the like.

Examples of the alkali metal are Na (work function: 2.36 eV), K (work function: 2.28 eV), Rb (work function: 2.16 eV), Cs (work function: 1.95 eV) and the like, among which a substance having a work function of 2.9 eV or less is particularly preferable. Among the above, the reductive dopant is preferably K, Rb or Cs, more preferably Rb or Cs, the most preferably Cs.

Examples of the alkali earth metal are Ca (work function: 2.9 eV), Sr (work function: 2.0 to 2.5 eV), Ba (work function: 2.52 eV), and the like, among which a substance having a work function of 2.9 eV or less is particularly preferable.

Examples of the rare-earth metal are Sc, Y, Ce, Tb, Yb and the like, among which a substance having a work function of 2.9 eV or less is particularly preferable.

Since the above preferable metals have particularly high reducibility, addition of a relatively small amount of these alkali metals to an electron injecting zone can enhance luminance intensity and lifetime of the organic EL device.

Examples of the alkali metal compound are an alkali oxide such as $Li_2O$, $Cs_2O$ or $K_2O$, an alkali halogen compound such as LiF, NaF, CsF or KF and the like, among which LiF, $Li_2O$ and NaF are preferable.

Examples of the alkali earth metal compound are BaO, SrO, CaO, a mixture thereof such as $Ba_xSr_{1-x}O$ (0<x<1) or $Ba_xCa_{1-x}O$ (0<x<1) and the like, among which BaO, SrO and CaO are preferable.

Examples of the rare-earth metal compound are $YbF_3$, $ScF_3$, $ScO_3$, $Y_2O_3$, $Ce_2O_3$, $GdF_3$, $TbF_3$ and the like, among which $YbF_3$, $ScF_3$ and $TbF_3$ are preferable.

The alkali metal complex, the alkali earth metal complex and the rare-earth metal complex are not specifically limited, as long as at least one of alkali metal ion, alkali earth metal ion and rare-earth metal ion is contained therein as metal ion. Ligand for each of the complexes is preferably quinolinol, benzoquinolinol, acridinol, phenanthridinol, hydroxyphenyl oxazole, hydroxyphenyl thiazole, hydroxydiaryl oxadiazole, hydroxydiaryl thiadiazole, hydroxyphenyl pyridine, hydroxyphenyl benzoimidazole, hydroxybenzo triazole, hydroxy fluborane, bipyridyl, phenanthroline, phthalocyanine, porphyrin, cyclopentadiene, β-diketones, azomethines, or a derivative thereof, but the ligand is not limited thereto.

The reductive dopant is preferably added to form a layer or an island pattern in the interfacial region. The layer of the reductive dopant or the island pattern of the reductive dopant is preferably formed by depositing the reductive dopant by resistance heating deposition while an emitting material for forming the interfacial region or an organic substance as a electron-injecting material are simultaneously deposited, so that the reductive dopant is dispersed in the organic substance. Dispersion concentration at which the reductive dopant is dispersed in the organic substance is a mole ratio (organic substance to reductive dopant) of 100:1 to 1:100, preferably 5:1 to 1:5.

When the reductive dopant forms the layer, the emitting material or the electron injecting material for forming the organic layer of the interfacial region is initially layered, and the reductive dopant is subsequently deposited singularly thereon by resistance heating deposition to form a preferably 0.1 to 15 nm-thick layer.

When the reductive dopant forms the island pattern, the emitting material or the electron injecting material for forming the organic layer of the interfacial region is initially formed in an island shape, and the reductive dopant is subsequently deposited singularly thereon by resistance heating deposition to form a preferably 0.05 to 1 nm-thick island shape.

A ratio of the main component to the reductive dopant in the organic EL device according to the present invention is preferably a mole ratio (main component to reductive dopant) of 5:1 to 1:5, more preferably 2:1 to 1:2.

The organic EL device according to the present invention preferably includes the electron injecting layer between the emitting layer and the cathode, and the electron injecting layer preferably contains a nitrogen-containing cyclic derivative as the main component.

It should be noted that "as the main component" means that the nitrogen-containing cyclic derivative is contained in the electron injecting layer with a content of 50 mass % or more.

The electron injecting layer or the electron transporting layer, which aids injection of the electrons into the emitting layer, has a high electron mobility. The electron injecting layer is provided for adjusting energy level, by which, for instance, sudden changes of the energy level can be reduced.

A preferable example of an electron transporting material for forming the electron injecting layer is an aromatic heterocyclic compound having in the molecule at least one heteroatom. Particularly, a nitrogen-containing cyclic derivative is preferable.

A preferable example of the nitrogen-containing cyclic derivative is a nitrogen-containing cyclic metal chelate complex represented by the following formula (A).

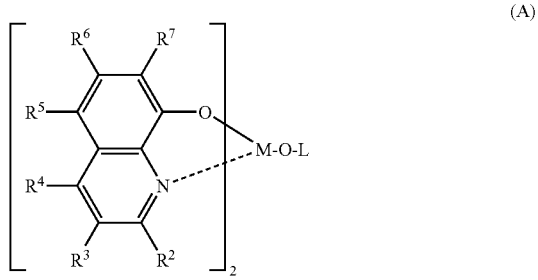

(A)

In the formula, $R^2$ to $R^7$ each independently represent a hydrogen atom, a halogen atom, an oxy group, an amino group, a hydrocarbon group having 1 to 40 carbon atoms, an alkoxy group, an aryloxy group, an alkoxycarbonyl group or a heterocyclic group. $R^2$ to $R^7$ may be substituted or unsubstituted.

Examples of the halogen atom are fluorine, chlorine, bromine, iodine and the like. Examples of a substituted or unsubstituted amino group are an alkylamino group, an arylamino group and an aralkylamino group.

Examples of the hydrocarbon group having 1 to 40 carbon atoms are a substituted or unsubstituted alkyl group, an alkenyl group, a cycloalkyl group, an aryl group, an aralkyl group and the like.

Examples of the alkyl group are a methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neo-pentyl group, 1-methylpentyl group, 2-methylpentyl group, 1-pentylhexyl group, 1-butylpentyl group, 1-heptyloctyl group, 3-methylpentyl group, hydroxymethyl group, 1-hydroxyethyl group, 2-hydroxyethyl group, 2-hydroxyisobutyl group, 1,2-dihydoroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 1,2-dinitroethyl group, 2,3-dinitro-t-butyl group and 1,2,3-trinitropropyl group.

Among the above, the alkyl group is preferably a methyl group, an ethyl group, a propyl group, an isopropyl group, an n-butyl group, a s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an neo-pentyl group, a 1-methylpentyl group, a 1-pentylhexyl group, a 1-butylpentyl group, or a 1-heptyloctyl group.

Examples of the alkenyl group are a vinyl group, allyl group, 1-butenyl group, 2-butenyl group, 3-butenyl group, 1,3-butanedienyl group, 1-methylvinyl group, styryl group, 2,2-diphenylvinyl group, 1,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl-1-butenyl group and 3-phenyl-1-butenyl group, among which a styryl group, 2,2-phenylvinyl group, 1,2-diphenylvinyl group and the like are preferable.

Examples of the cycloalkyl group are a cyclopentyl group, cyclohexyl group, cyclooctyl group, and 3,5-tetramethylcyclohexyl group, among which cyclohexyl group, cyclooctyl group and 3,5-tetramethylcyclohexyl group are preferable.

The alkoxy group is a group represented by —OY. Examples of Y are the same as the examples described in relation to the alkyl group, and preferable examples of Y are also the same as those described in relation to the alkyl group.

Examples of non-condensed aryl group are a phenyl group, biphenyl-2-yl group, biphenyl-3-yl group, biphenyl-4-yl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 4'-methylbiphenylyl group, 4"-t-butyl-p-terphenyl-4-yl group, o-cumenyl group, m-cumenyl group, p-cumenyl group, 2,3-xylyl group, 3,4-xylyl group, 2,5-xylyl group, mesityl group, m-quater-phenyl group and the like.

Among the above, a phenyl group, a biphenyl-2-yl group, a biphenyl-3-yl group, a biphenyl-4-yl group, an m-terphenyl-4-yl group, an m-terphenyl-3-yl group, an m-terphenyl-2-yl group, a p-tolyl group, a 3,4-xylyl group, an m-quarter-phenyl-2-yl group are preferable.

Examples of a condensed aryl group are a 1-naphthyl group and 2-naphtyl group.

The heterocyclic group, which may be monocyclic or condensed, preferably has 1 to 20 carbon atoms forming the ring, more preferably 1 to 12 carbon atoms forming the ring, further preferably 2 to 10 carbon atoms forming the ring. The heterocyclic group is an aromatic heterocyclic group having at least one heteroatom selected from a group of a nitrogen atom, an oxygen atom, a sulfur atom and a selenium atom. Examples of the heterocyclic group are groups induced by pirrolidine, piperidine, piperazine, morpholine, thiophene, selenophene, furane, pyrrole, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzoimidazole, benzooxazole, benzothiazole, benzotriazole, tetra-aza indene, carbazole, azepine and the like, preferably groups induced by furane, thiophene, pyridine, pyrazine, pyrimidine, pyridazine, triazine, quinoline, phthalazine, naphthyridine, quinoxaline and quinazoline, further preferably groups induced by frane, thiophene, pyridine and quinoline, further more preferably a quinolinyl group.

Examples of the aralkyl group are a benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, 1-chloro-2-phenylisopropyl group and the like.

Among the above, a benzyl group, p-cyanobenzyl group, m-cyanobenzyl group, o-cyanobenzyl group, 1-phenylethyl group, 2-phenylethyl group, 1-phenylisopropyl group and 2-phenylisopropyl group are preferable.

The aryloxy group is represented by —OY'. Preferable examples of Y' are a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group and the like.

A heteroaryloxy group of the aryloxy group is represented by —OZ'. Examples of Z' are a 2-pyroryl group, 3-pyroryl group, pyrazinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzolfuranyl group, 4-berzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthrydinyl group, 2-phenanthrydinyl group, 3-phenanthrydinyl group, 4-phenanthrydinyl group, 6-phenanthrydinyl group, 7-phenanthrydinyl group, 8-phenanthrydinyl group, 9-phenanthrydinyl group, 10-phenanthrydinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-3-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group and the like.

The alkoxycarbonyl group is represented by —COOY'. Examples of Y' are the same as the examples of the alkyl group.

The alkylamino group and the aralkylamino group are represented by —NQ$^1$Q$^2$. Examples for each of Q$^1$ and Q$^2$ are the same as the examples described in relation to the alkyl group and the aralkyl group, and preferable examples for each of Q$^1$ and Q$^2$ are also the same as those described in relation to the alkyl group and the aralkyl group. Either one of Q$^1$ and Q$^2$ may be a hydrogen atom.

The arylamino group is represented by —NAr$^1$Ar$^2$. Examples for each of Ar$^1$ and Ar$^2$ are the same as the examples described in relation to the non-condensed aryl group and the condensed aryl group. Either one of Ar$^1$ and Ar$^2$ may be a hydrogen atom.

M represents aluminum (Al), gallium (Ga) or indium (In), among which In is preferable.

L in the formula (A) represents a group represented by the following formula (A') or the following formula (A").

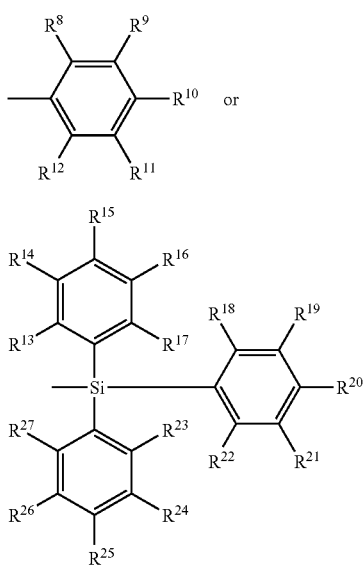

(A')

(A")

In the formula, $R^8$ to $R^{12}$ each independently represent a hydrogen atom or a substituted or unsubstituted hydrocarbon group having 1 to 40 carbon atoms. Adjacent groups may form a cyclic structure $R^{13}$ to $R^{27}$ each independently represent a hydrogen atom or a substituted or unsubstituted hydrocarbon group having 1 to 40 carbon atoms. Adjacent groups may form a cyclic structure.

Examples of the hydrocarbon group having 1 to 40 carbon atoms represented by each of $R^8$ to $R^{12}$ and $R^{13}$ to $R^{27}$ in the formulae (A') and (A") are the same as those of $R^2$ to $R^7$.

Examples of a divalent group formed when an adjacent set of $R^8$ to $R^{12}$ and $R^{13}$ to $R^{27}$ forms a cyclic structure are a tetramethylene group, a pentamethylene group, a hexamethylene group, a diphenylmethane-2,2'-diyl group, a diphenylethane-3,3'-diyl group, a diphenylpropane-4,4'-diyl group and the like.

Examples of the nitrogen-containing cyclic metal chelate complex represented by the formula (A) will be shown below. However, the nitrogen-containing cyclic metal chelate complex is not limited to the exemplary compounds shown below.

(A-1)

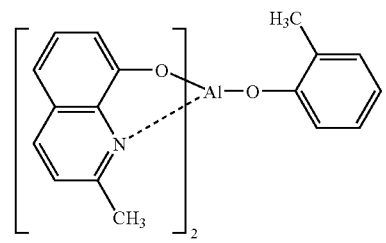

(A-2)

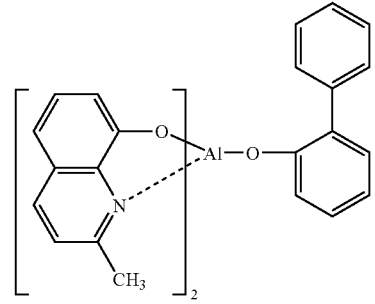

(A-3)

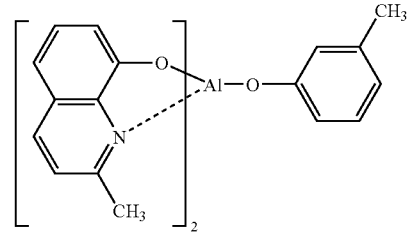

(A-4)

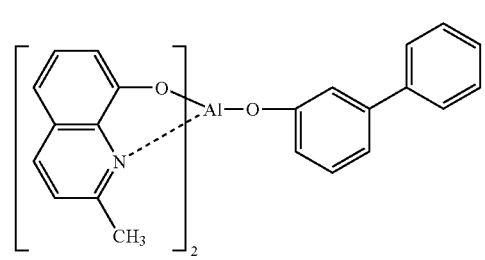

(A-5)

(A-6)

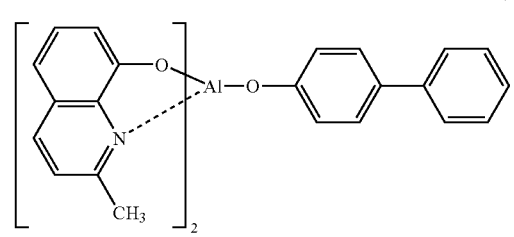

(A-7)

(A-8)

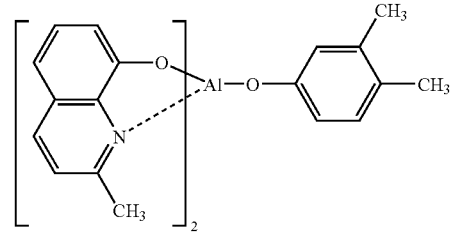

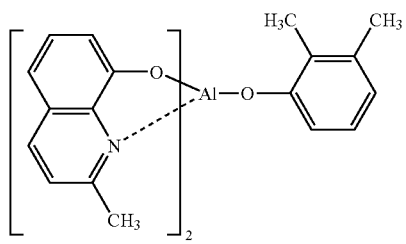 (A-9)
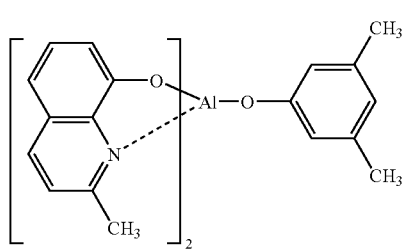 (A-10)
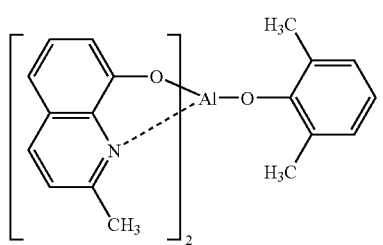 (A-11)
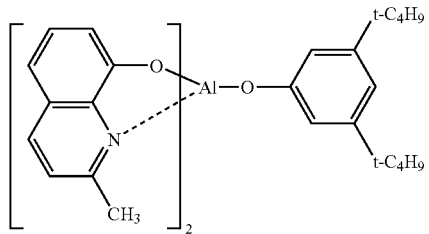 (A-12)
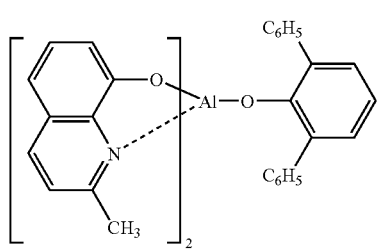 (A-13)
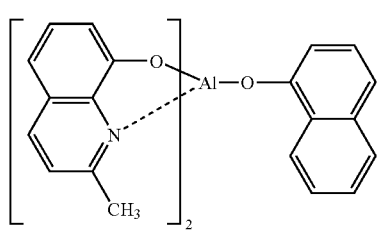 (A-14)
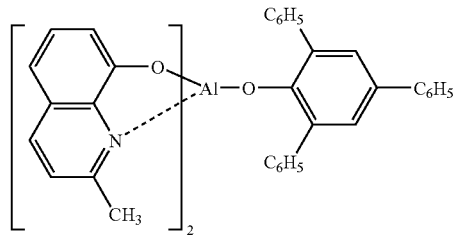 (A-15)
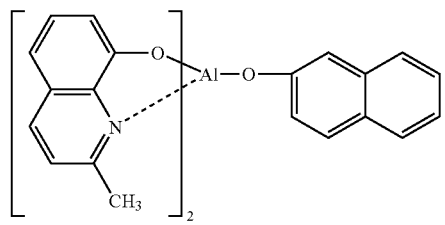 (A-16)
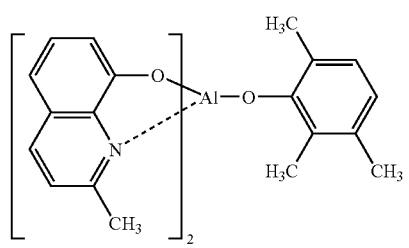 (A-17)
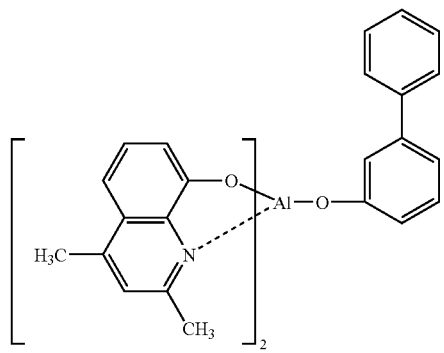 (A-18)
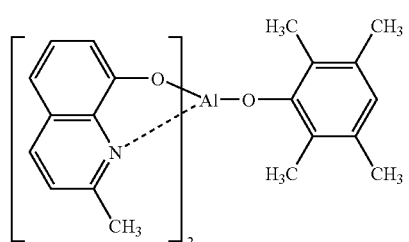 (A-19)
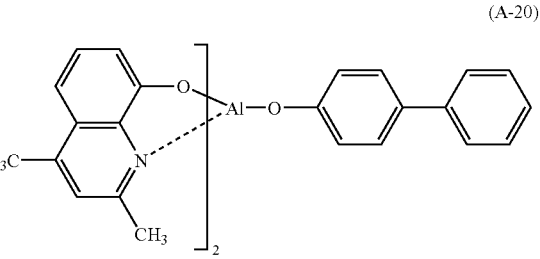 (A-20)

(A-21)
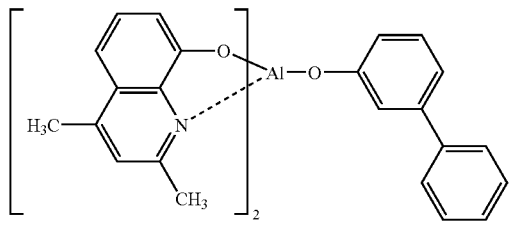
(A-22)
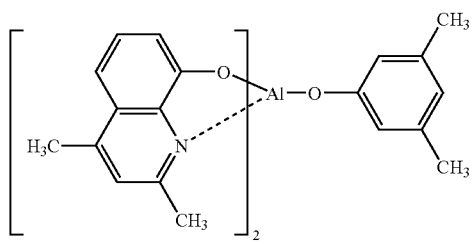
(A-23)
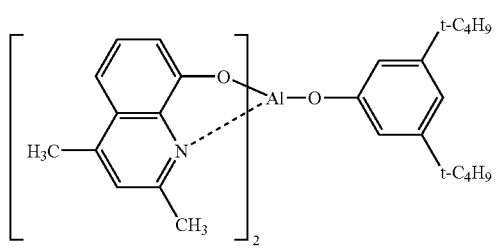
(A-24)
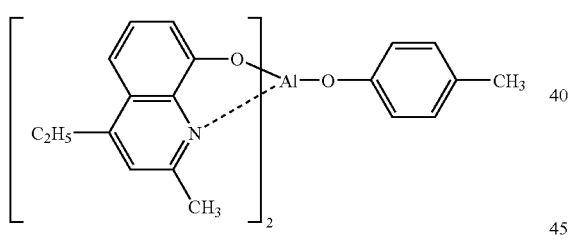
(A-25)
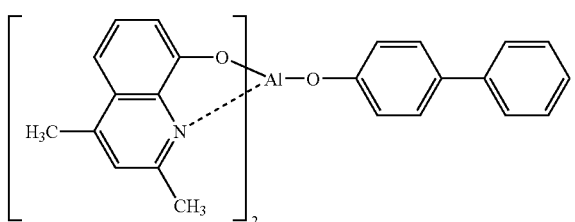
(A-26)
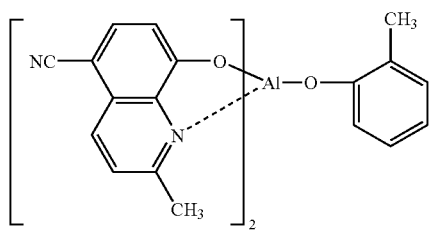
(A-27)
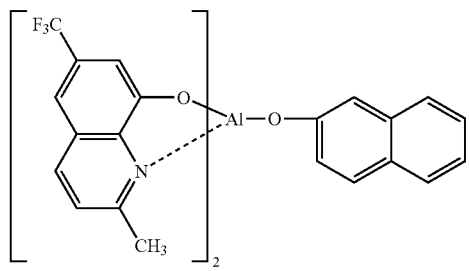
(A-28)
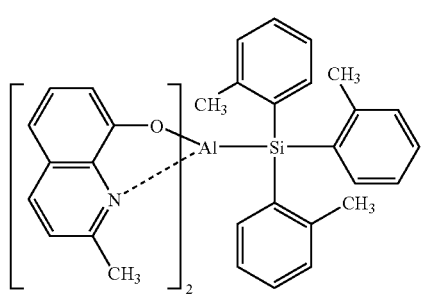
(A-29)
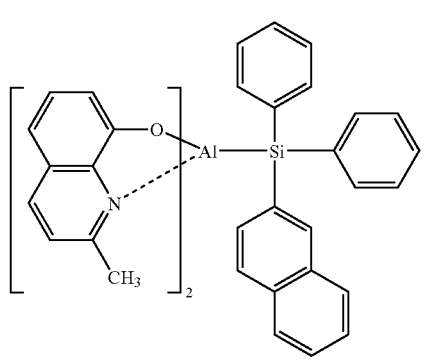
(A-30)
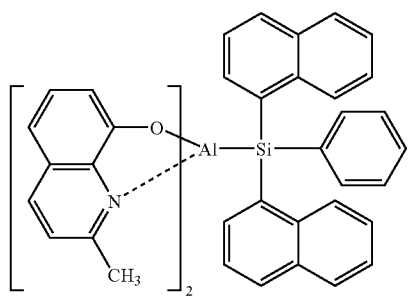
(A-31)
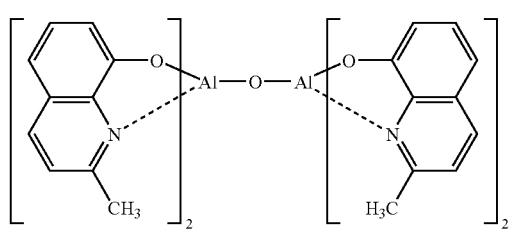

-continued

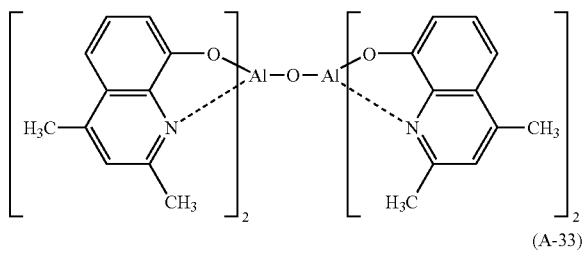
(A-32)

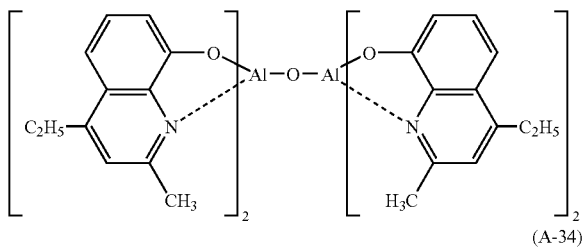
(A-33)

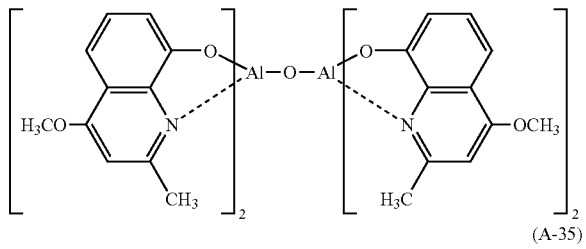
(A-34)

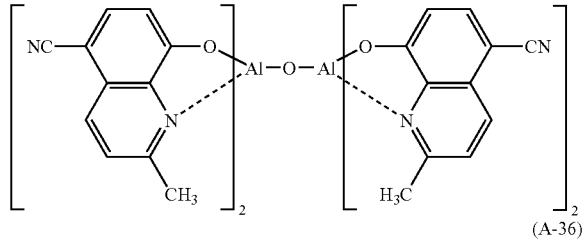
(A-35)

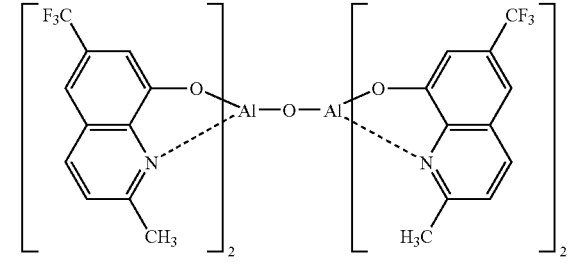
(A-36)

According to the present invention, the organic thin-film layer preferably includes the electron injecting layer between the phosphorescent emitting layer and the cathode, and the electron injecting layer preferably contains a nitrogen-containing cyclic derivative. The electron injecting layer or the electron transporting layer, which aids injection of the electrons into the emitting layer, has a high electron mobility. The electron injecting layer is provided for adjusting energy level, by which, for instance, sudden changes of the energy level can be reduced. As a material for the electron injecting layer or the electron transporting layer, 8-hydroxyquinoline or a metal complex of its derivative, an oxadiazole derivative and a nitrogen-containing heterocyclic derivative are preferable. An example of the 8-hydroxyquinoline or the metal complex of its derivative is a metal chelate oxinoid compound containing a chelate of oxine (typically 8-quinolinol or 8-hydroxyquinoline). For instance, tris(8-quinolinol) aluminum can be used. Examples of the oxadiazole derivative are as follows.

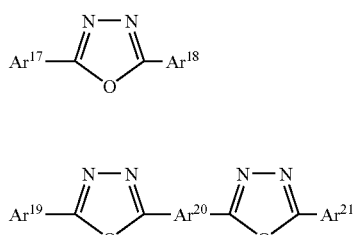

In the formula, $Ar^{17}$, $Ar^{18}$, $Ar^{19}$, $Ar^{21}$, $Ar^{22}$ and $Ar^{25}$ each represent a substituted or unsubstituted aryl group. $Ar^{17}$, $Ar^{19}$ and $Ar^{22}$ may be respectively the same as or different from $Ar^{18}$, $Ar^{21}$ and $Ar^{25}$. $Ar^{20}$, $Ar^{23}$ and $Ar^{24}$ each represent a substituted or unsubstituted arylene group. $Ar^{23}$ and $Ar^{24}$ may be mutually the same or different.

Examples of the arylene group are a phenylene group, a naphtylene group, a biphenylene group, an anthranylene group, a perylenylene group and a pyrenylene group. Examples of the substituent therefor are an alkyl group having 1 to 10 carbon atoms, an alkoxy group having 1 to 10 carbon atoms and a cyano group. Such an electron transport compound is preferably an electron transport compound that can be favorably formed into a thin film(s). Examples of the electron transport compounds are as follows.

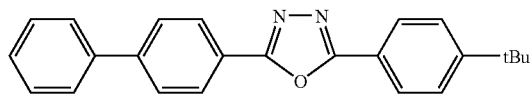
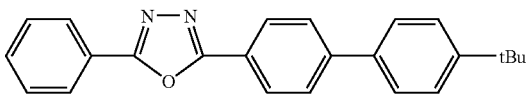
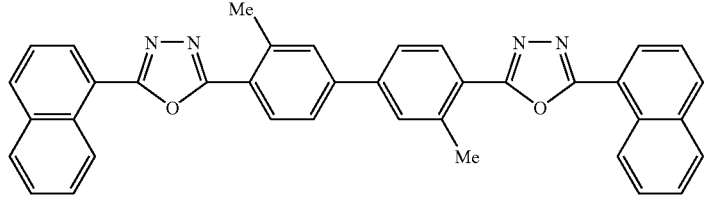

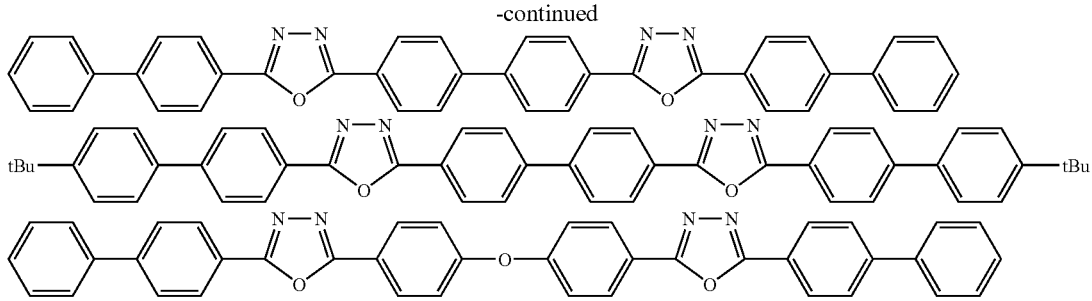

An example of the nitrogen-containing heterocyclic derivative is a nitrogen-containing heterocyclic derivative that is not a metal complex, the derivative being formed of an organic compound represented by either one of the following general formulae. Specific examples of the nitrogen-containing heterocyclic derivative are five-membered ring or six-membered ring derivative having a skeleton represented by the formula (A) and a derivative having a structure represented by the formula (B).

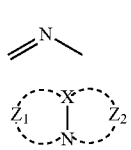

In the formula (B), X represents a carbon atom or a nitrogen atom. $Z_1$ and $Z_2$ each independently represent an atom group from which a nitrogen-containing heterocycle can be formed.

Preferably, the nitrogen-containing heterocyclic derivative is an organic compound having a nitrogen-containing aromatic polycyclic group having a five-membered ring or six-membered ring. When the nitrogen-containing heterocyclic derivative is such a nitrogen-containing aromatic polycyclic group that contains plural nitrogen atoms, the nitrogen-containing heterocyclic derivative may be a nitrogen-containing aromatic polycyclic organic compound having a skeleton formed by a combination of the skeletons respectively represented by the formulae (A) and (B), or by a combination of the skeletons respectively represented by the formulae (A) and (C).

A nitrogen-containing group of the nitrogen-containing organic compound is selected from nitrogen-containing heterocyclic groups respectively represented by the following general formulae.

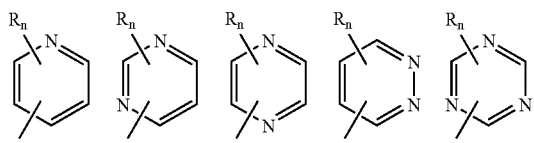

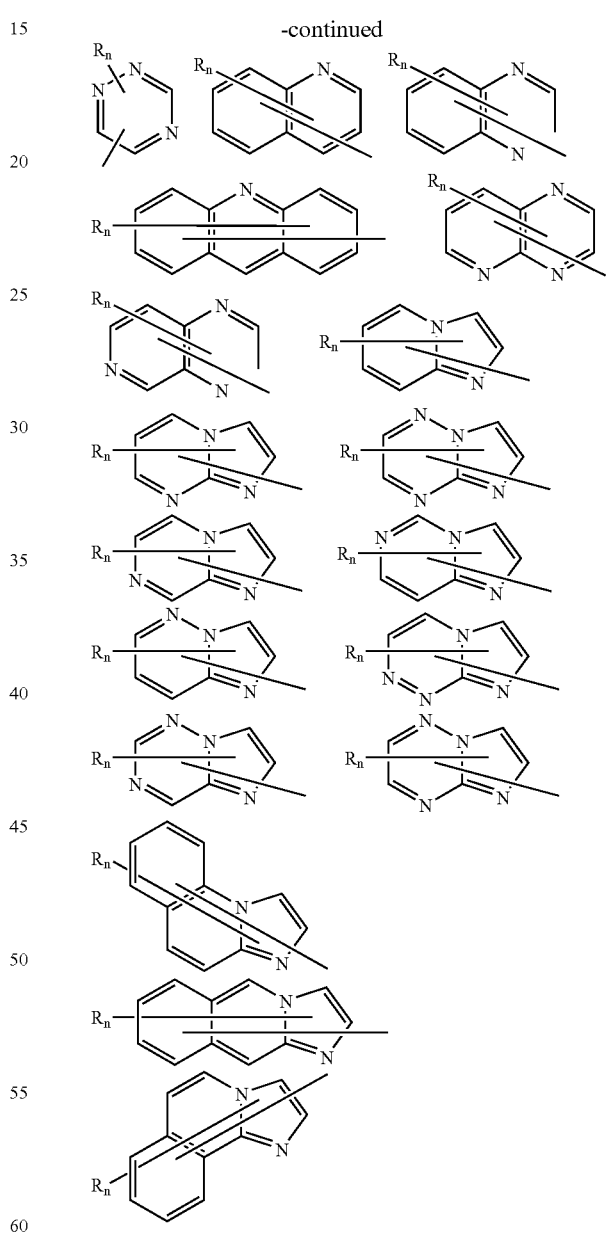

In the formulae: R represents an aryl group having 6 to 40 carbon atoms, a heteroaryl group having 3 to 40 carbon atoms, an alkyl group having 1 to 20 carbon atoms or an alkoxy group having 1 to 20 carbon atoms; and n represents an integer in a range of 0 to 5. When n is an integer of 2 or more, plural R may be mutually the same or different.

A preferable specific compound is a nitrogen-containing heterocyclic derivative represented by the following formula.

In the formula, HAr represents a substituted or unsubstituted nitrogen-containing heterocycle having 3 to 40 carbon atoms; $L^1$ represents a single bond, a substituted or unsubstituted arylene group having 6 to 40 carbon atoms, or a substituted or unsubstituted heteroarylene group having 3 to 40 carbon atoms; $Ar^1$ represents a substituted or unsubstituted divalent aromatic hydrocarbon group having 6 to 40 carbon atoms; and $Ar^2$ represents a substituted or unsubstituted aryl group having 6 to 40 carbon atoms, or a substituted or unsubstituted heteroaryl group having 3 to 40 carbon atoms.

HAr is exemplarily selected from the following group.

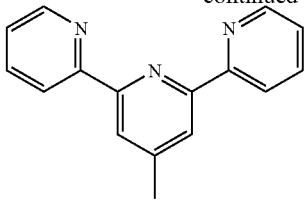

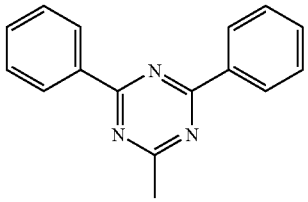

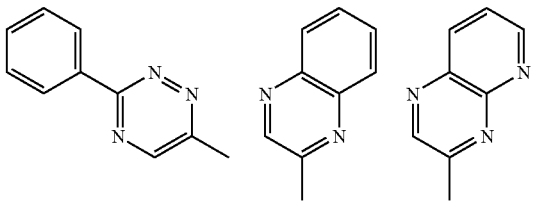

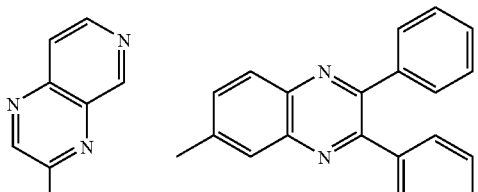

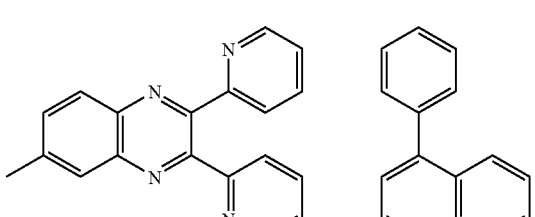

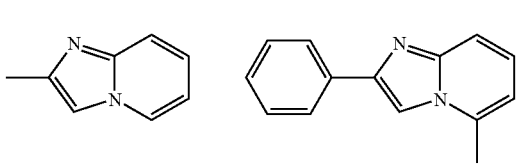

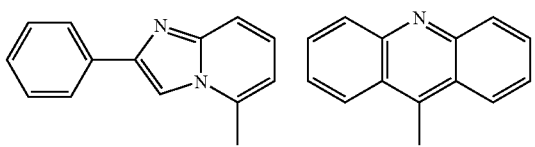

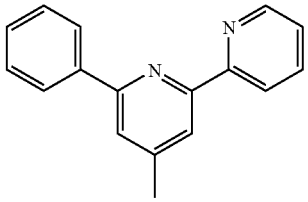

$L^1$ is exemplarily selected from the following group.

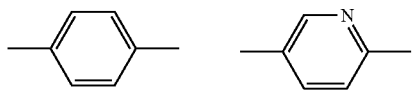

$Ar^2$ is exemplarily selected from the following group.

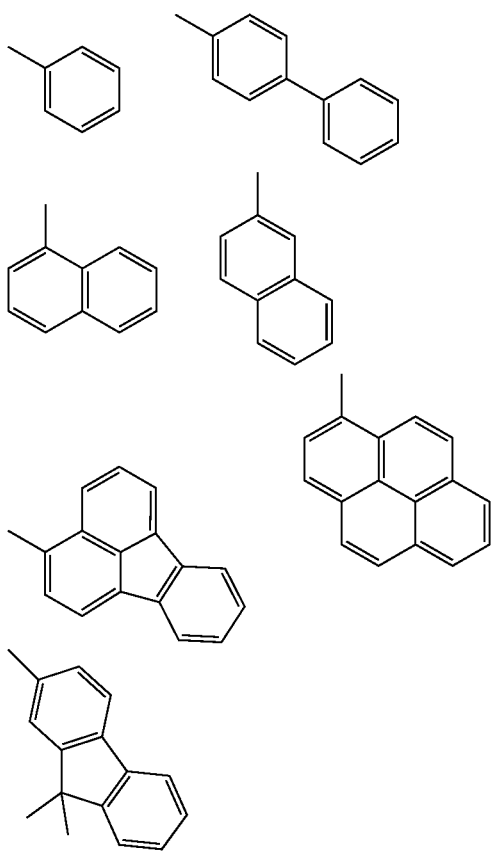

$Ar^1$ is exemplarily selected from the following arylanthranil groups.

In the formula, $R^1$ to $R^{14}$ each independently represent a hydrogen atom, a halogen atom, an alkyl group having 1 to 20 carbon atoms, an alkoxy group having 1 to 20 carbon atoms, an aryloxy group having 6 to 40 carbon atoms, a substituted or unsubstituted aryl group having 6 to 40 carbon atoms, or a heteroaryl group having 3 to 40 carbon atoms. $Ar^3$ represents a substituted or unsubstituted aryl group having 6 to 40 carbon atoms, or a heteroaryl group having 3 to 40 carbon atoms.

The nitrogen-containing heterocyclic derivative may be a nitrogen-containing heterocyclic derivative in which $R^1$ to $R^8$ in $Ar^1$ represented by the above formula each represent a hydrogen atom.

Other than the above, the following compound (see JP-A-9-3448) can be favorably used.

In the formula, $R_1$ to $R_4$ each independently represent a hydrogen atom, a substituted or unsubstituted aliphatic group, a substituted or unsubstituted aliphatic cyclic group, a substituted or unsubstituted carbocyclic aromatic cyclic group, substituted or unsubstituted heterocyclic group. $X_1$ and $X_2$ each independently represent an oxygen atom, a sulfur atom or a dicyanomethylene group.

Alternatively, the following compound (see JP-A-2000-173774) can also be favorably used.

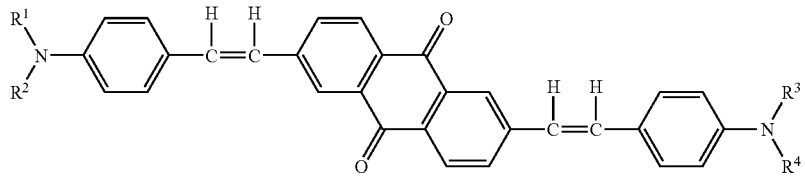

In the formula, $R^1$, $R^2$, $R^3$ and $R^4$, which may be mutually the same or different, each are represented by the following formula.

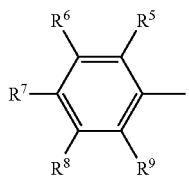

In the formula, $R^5$, $R^6$, $R^7$, $R^8$ and $R^9$, which may be mutually the same or different, each represent a hydrogen atom, a saturated or unsaturated alkoxy group, an alkyl group, an amino group or an alkylamino group. At least one of $R^5$, $R^6$, $R^7$, $R^8$ and $R^9$ represents a saturated or unsaturated alkoxy group, an alkyl group, an amino group or an alkylamino group.

A polymer compound containing the nitrogen-containing heterocyclic group or a nitrogen-containing heterocyclic derivative may be used.

The electron transporting layer preferably contains at least one of nitrogen-containing heterocycle derivatives respectively represented by the following formulae (201) to (203).

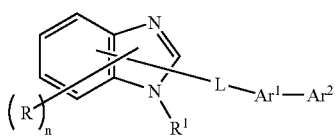

(201)

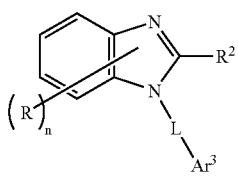

(202)

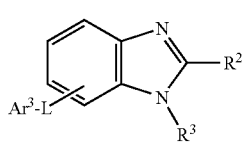

(203)

In the formulae (201) to (203): R represents a hydrogen atom, a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms; n represents an integer in a range of 0 to 4; $R^1$ represents a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or an alkoxy group having 1 to 20 carbon atoms; $R^2$ and $R^3$ each independently represent a hydrogen atom, a substituted or unsubstituted aryl group having 6 to 60 carbon atoms, a substituted or unsubstituted pyrydyl group, a substituted or unsubstituted quinolyl group, a substituted or unsubstituted alkyl group having 1 to 20 carbon atoms, or a substituted or unsubstituted alkoxy group having 1 to 20 carbon atoms; L represents a substituted or unsubstituted arylene group having 6 to 60 carbon atoms, a substituted or unsubstituted pyridinylene group, a substituted or unsubstituted quinolinylene group, or a substituted or unsubstituted fluorenylene group; $Ar^1$ represents a substituted or unsubstituted arylene group having 6 to 60 carbon atoms, a substituted or unsubstituted pyridinylene group, or a substituted or unsubstituted quinolinylene group; and $Ar^2$ represents a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms or a substituted or unsubstituted alkoxy group having 1 to 20 carbon atoms.

$Ar^3$ represents a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, a substituted or unsubstituted alkoxy group having 1 to 20 carbon atoms, or a group represented by $-Ar^1-Ar^2$ ($Ar^1$ and $Ar^2$ may be the same as the above).

In the formulae (201) to (203), R represents a hydrogen atom, a substituted or unsubstituted aryl group having 6 to 60 carbon atoms, a substituted or unsubstituted pyridyl group, substituted or unsubstituted quinolyl group, a substituted or unsubstituted alkyl group having 1 to 20 carbon atoms, or a substituted or unsubstituted alkoxy group having 1 to 20 carbon atoms.

The aryl group having 6 to 60 carbon atom is preferably an aryl group having 6 to 40 carbon atoms, more preferably an aryl group having 6 to 20 carbon atoms. Examples of such an aryl group are a phenyl group, naphthyl group, anthryl group, phenanthryl group, naphthacenyl group, chrysenyl group, pyrenyl group, biphenyl group, terphenyl group, tolyl group, t-butylphenyl group, (2-phenylpropyl) phenyl group, fluoranthenyl group, fluorenyl group, a monovalent group formed of spirobifluorene, perfluorophenyl group, perfluoronaphthyl group, perfluoroanthryl group, perfluorobiphenyl group, a monovalent group formed of 9-phenylanthracene, a monovalent group formed of 9-(1'naphthyl) anthracene, a monovalent group formed of 9-(2'-naphthyl) anthracene, a monovalent group formed of 6-phenylchrysene, and a monovalent group formed of 9-[4-(diphenylamine)phenyl]anthracene, among which a phenyl group, naphthyl group, biphenyl group, terphenyl group, 9-(10-phenyl)anthryl group, 9-[10-(1'-naphthyl)]anthryl group and 9-[10-(2'-naphthyl)]anthryl group are preferable.

The alkyl group having 1 to 20 carbon atoms is preferably an alkyl group having 1 to 6 carbon atoms. Examples of such an alkyl group are a methyl group, ethyl group, propyl group, butyl group, pentyl group, hexyl group, and a haloalkyl group such as trifluoromethyl group. When such an alkyl group has 3 or more carbon atoms, the alkyl group may be linear, cyclic or branched.

The alkoxy group having 1 to 20 carbon atoms is preferably an alkoxy group having 1 to 6 carbon atoms. Examples of such an alkoxy group are a methoxy group, ethoxy group, propoxy group, butoxy group, pentyloxy group, and hexyloxy group. When such an alkoxy group has 3 or more carbon atoms, the alkoxy group may be linear, cyclic or branched.

Examples of a substituent for the group represented by R are a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms, or a substituted or unsubstituted heteroaryl group having 3 to 40 carbon atoms.

Examples of the halogen atom are fluorine, chlorine, bromine, iodine and the like.

Examples for each of the alkyl group having 1 to 20 carbon atoms, the alkoxy group having 1 to 20 carbon atoms, and an aryl group having 6 to 40 carbon atoms may be the same as the above examples.

Examples of the aryloxy group having 6 to 40 carbon atoms are a phenoxy group and a biphenyloxy group.

Examples of the heteroaryl group having 3 to 40 carbon atoms are a pyroryl group, furyl group, thienyl group, silolyl group, pyridyl group, quinolyl group, isoquinolyl group, benzofuryl group, imidazolyl group, pyrimidyl group, carbazolyl group, selenophenyl group, oxadiazolyl group and triazolyl group.

n is an integer in a range of 0 to 4, preferably 0 to 2.

In the formula (201), $R^1$ represents a substituted or unsubstituted aryl group having 6 to 60 carbon atoms, a substituted or unsubstituted pyridyl group, substituted or unsubstituted quinolyl group, a substituted or unsubstituted alkyl group having 1 to 20 carbon atoms, or an alkoxy group having 1 to 20 carbon atoms.

Examples for each of the groups, the preferable number of carbon atoms contained in each of the groups, and preferable examples of the substituent for each of the groups are the same as those described in relation to R.

In the formulae (202) and (203), $R^2$ and $R^3$ each independently represent a hydrogen atom, a substituted or unsubstituted aryl group having 6 to 60 carbon atoms, a substituted or unsubstituted pyridyl group, substituted or unsubstituted quinolyl group, a substituted or unsubstituted alkyl group having 1 to 20 carbon atoms, or a substituted or unsubstituted alkoxy group having 1 to 20 carbon atoms.

Examples for each of the groups, the preferable number of carbon atoms contained in each of the groups, and preferable examples of the substituent for each of the groups are the same as those described in relation to R.

In the formulae (201) to (203), L represents a substituted or unsubstituted arylene group having 6 to 60 carbon atoms, a substituted or unsubstituted pyridinylene group, a substituted or unsubstituted quinolinylene group, or a substituted or unsubstituted fluorenylene group.

The arylene group having 6 to 60 carbon atoms is preferably an arylene group having 6 to 40 carbon atoms, more preferably an arylene group having 6 to 20 carbon atoms. An example of such an arylene group is a divalent group formed by removing one hydrogen atom from the aryl group having been described in relation to R. Examples of a substituent for the group represented by L are the same as those described in relation to R.

Alternatively, L is preferably a group selected from a group consisting of the following.

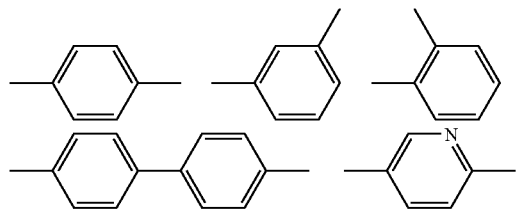

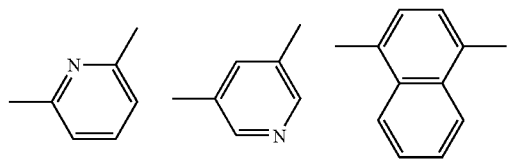

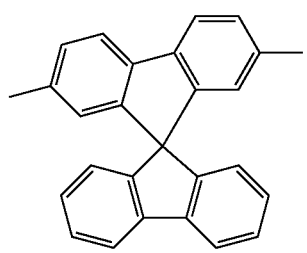

In the formula (201), $Ar^1$ represents a substituted or unsubstituted arylene group having 6 to 60 carbon atoms, a substituted or unsubstituted pyridinylene group, or a substituted or unsubstituted quinolinylene group. Examples of a substituent for the groups respectively represented by $Ar^1$ and $Ar^3$ are the same as those described in relation to R.

Alternatively, $Ar^1$ is preferably selected from a group consisting of condensed cyclic groups respectively represented by the following formulae (101) to (110).

(101)

(102)

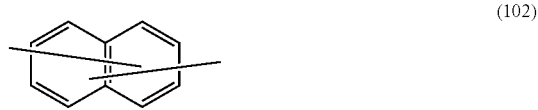

(103)

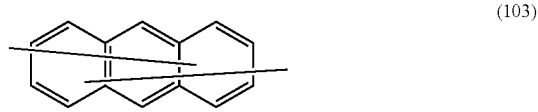

(104)

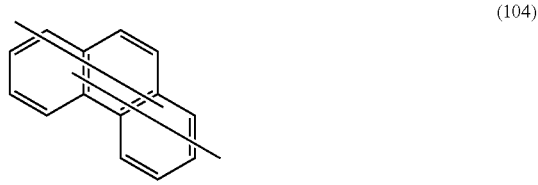

(105)

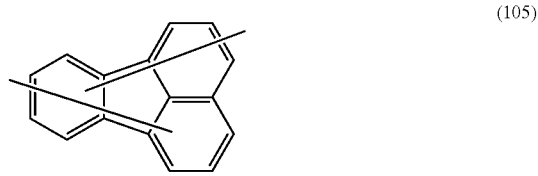

(106)

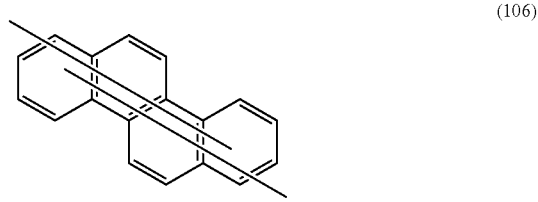

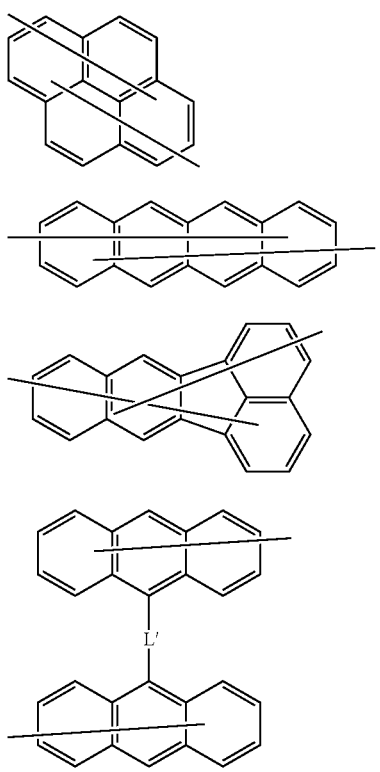

(107)

(108)

(109)

(110)

In the formulae (101) to (110), the condensed rings each may be linked with a link group formed of a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms or a substituted or unsubstituted heteroaryl group having 3 to 40 carbon atoms. When the rings each is linked with plural link groups, the plural link groups may be mutually the same or different. Examples for each of the groups are the same as those described above.

In the formula (110), L' represents a single bond or a group selected from a group consisting of the following.

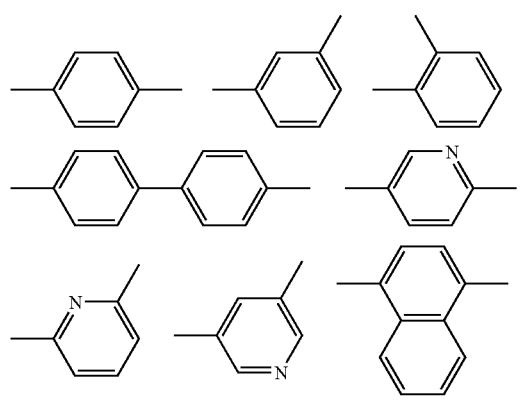

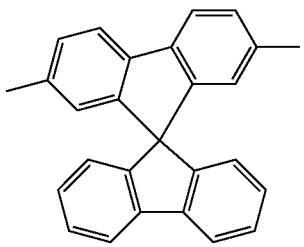

The structure of $Ar^1$ represented by the formula (103) is preferably a condensed cyclic group represented by any one of the following formulae (111) to (125).

(111)

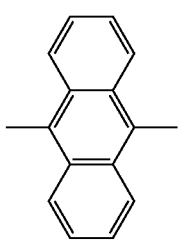

(112)

(113)

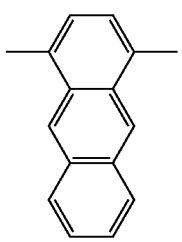

(114)

(115)
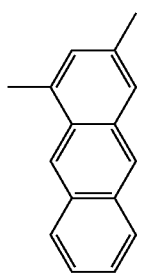

(116)
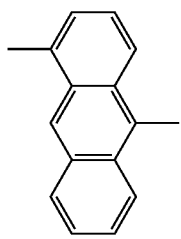

(117)
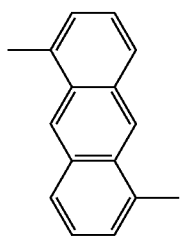

(118)
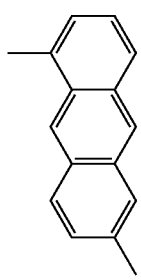

(119)
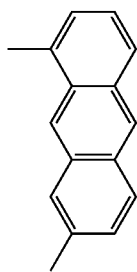

(120)
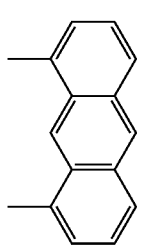

(121)
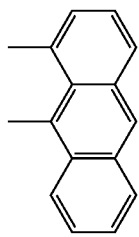

(122)
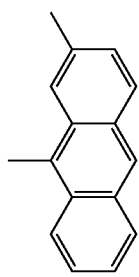

(123)
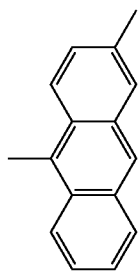

(124)
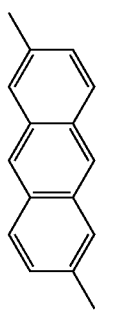

(125)
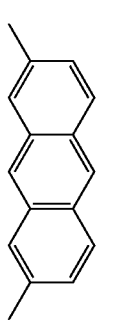

In the formulae (111) to (125), the condensed rings each may be linked with a link group formed of a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms or a substituted or unsubstituted heteroaryl group having 3 to 40 carbon atoms. When the rings each is linked with plural link groups, the plural link groups may be mutually the same or different. Examples for each of the groups are the same as those described above.

In the formula (201), $Ar^2$ represents a substituted or unsubstituted aryl group having 6 to 60 carbon atoms, a substituted or unsubstituted pyridyl group, substituted or unsubstituted quinolyl group, a substituted or unsubstituted alkyl group having 1 to 20 carbon atoms, or a substituted or unsubstituted alkoxy group having 1 to 20 carbon atoms.

Examples for each of the groups, the preferable number of carbon atoms contained in each of the groups, and preferable examples of the substituent for each of the groups are the same as those described in relation to R.

In the formulae (202) and (203), $Ar^3$ represents a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, a substituted or unsubstituted alkoxy group having 1 to 20 carbon atoms, or a group represented by —$Ar^1$—$Ar^2$ ($Ar^1$ and $Ar^2$ may be the same as the above).

Examples for each of the groups, the preferable number of carbon atoms contained in each of the groups, and preferable examples of the substituent for each of the groups are the same as those described in relation to R.

Alternatively, $Ar^3$ is preferably selected from a group consisting of condensed cyclic groups respectively represented by the following formulae (126) to (135).

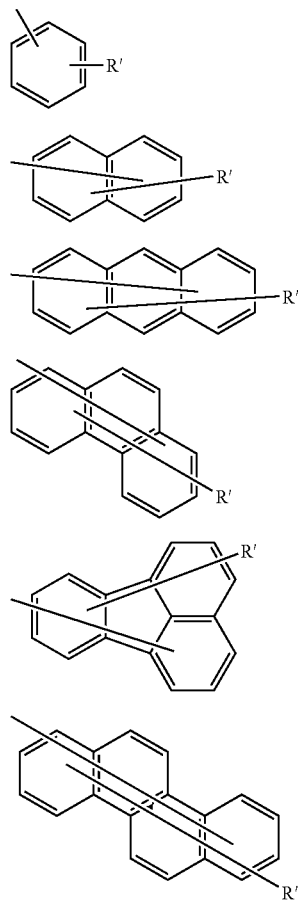

(126)
(127)
(128)
(129)
(130)
(131)

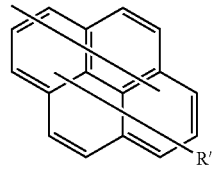

(132)

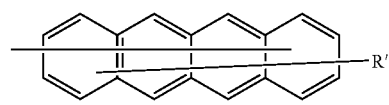

(133)

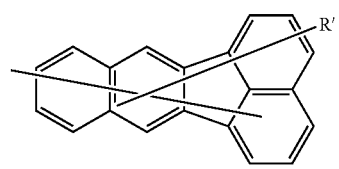

(134)

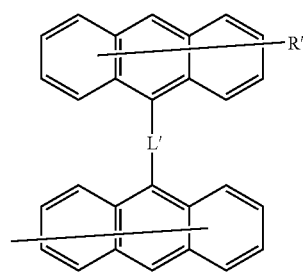

(135)

In the formulae (126) to (135), the condensed rings each may be linked with a link group formed of a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms or a substituted or unsubstituted heteroaryl group having 3 to 40 carbon atoms. When the rings each is linked with plural link groups, the plural link groups may be mutually the same or different. Examples for each of the groups are the same as those described above.

In the formula (135), L' represents the same as the above.

In the formulae (126) to (135), R' represents a hydrogen atom, a substituted or unsubstituted alkyl group having 1 to 20 carbon atoms, a substituted or unsubstituted aryl group having 6 to 40 carbon atoms, or substituted or unsubstituted heteroaryl group having 3 to 40 carbon atoms. Examples for each of the groups are the same as those described above.

A structure represented by the formula (128), which is an example of $Ar^3$, is preferably a condensed cyclic group represented by any one of the following formulae (136) to (158).

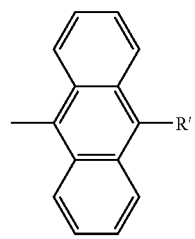

(136)

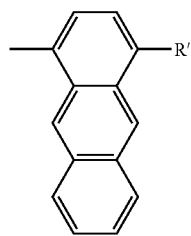 (137)
 (138)
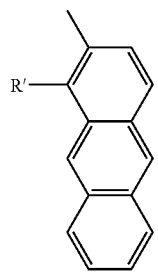 (139)
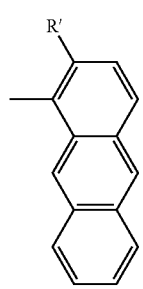 (140)
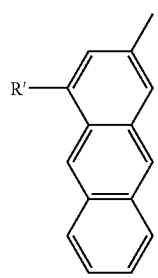 (141)
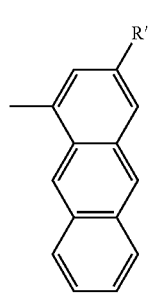 (142)
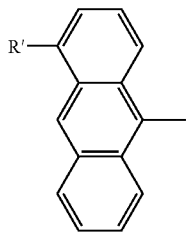 (143)
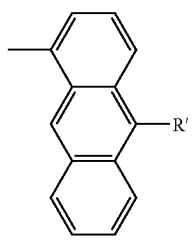 (144)
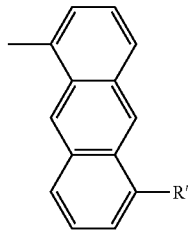 (145)
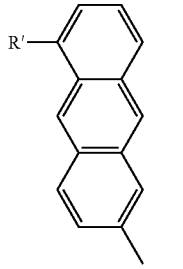 (146)
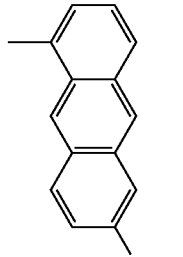 (147)
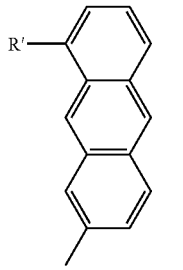 (148)

(149) 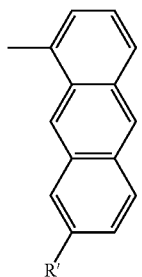

(150) 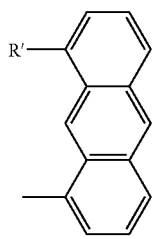

(151) 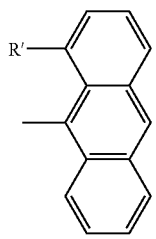

(152) 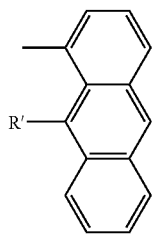

(153) 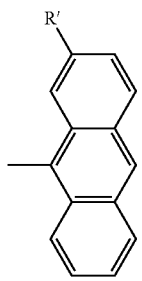

(154) 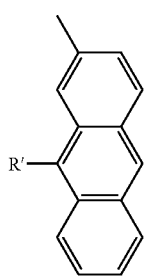

(155) 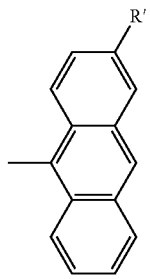

(156) 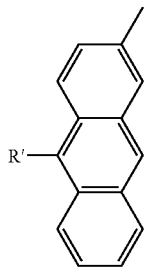

(157) 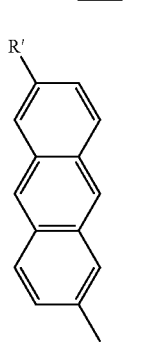

(158) 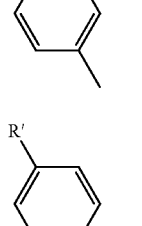

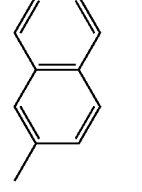

In the formulae (136) to (158), the condensed rings each may be linked with a link group formed of a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms or a substituted or unsubstituted heteroaryl group having 3 to 40 carbon atoms. When the rings each is linked with plural link groups, the plural link groups may be mutually the same or different. Examples for each of the groups are the same as those described above R' is the same as the above.

Alternatively, Ar² and Ar³ each independently are preferably a group selected from a group consisting of the following.

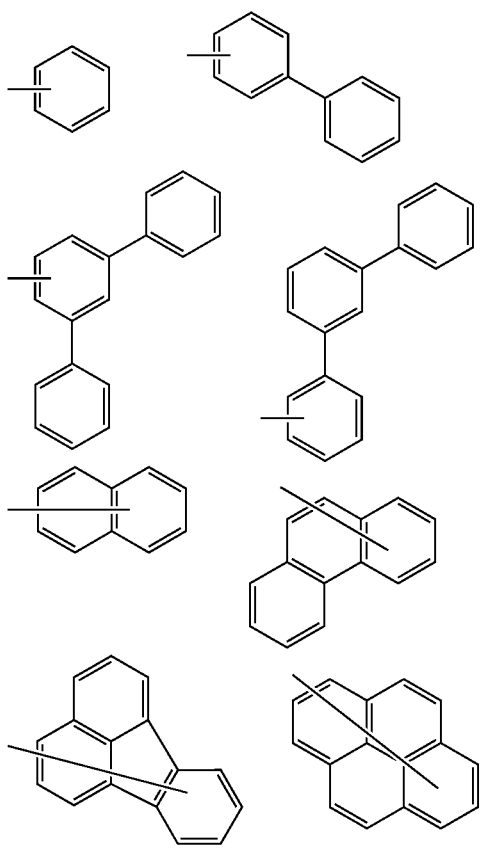
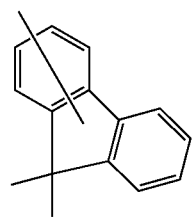

Examples of the nitrogen-containing heterocyclic derivative represented by any one of the general formulae (201) to (203) according to the present invention will be shown below. However, the present invention is not limited to the exemplary compounds shown below.

In the chart shown below, HAr represents any one of structures represented by the formulae (201) to (203).

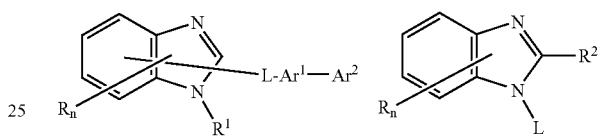
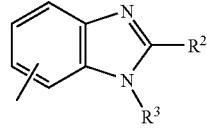

| | HAr—L—Ar¹—Ar² | | |
|---|---|---|---|
| HAr | L | Ar¹ | Ar² |
| 1-1 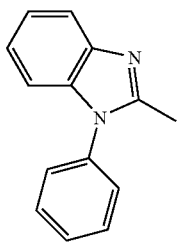 | 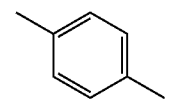 | 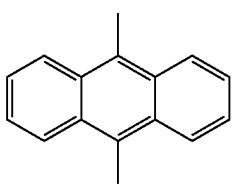 | 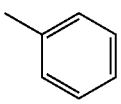 |
| 2 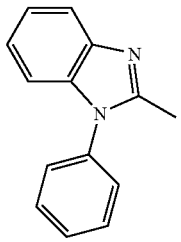 | 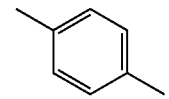 | 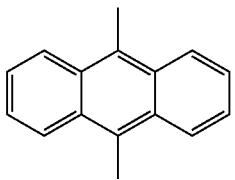 | 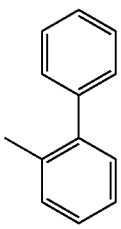 |

US 8,025,815 B2
-continued
| | HAr | L | Ar¹ | Ar² |
|---|---|---|---|---|
| 3 | 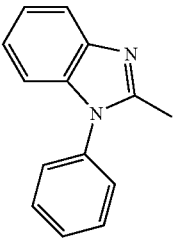 | 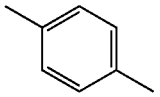 | 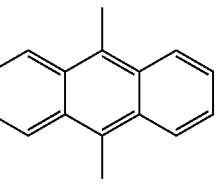 | 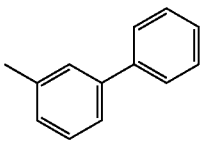 |
| 4 | 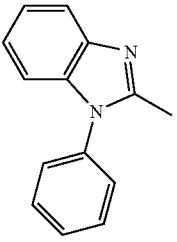 | 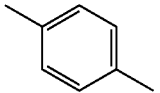 | 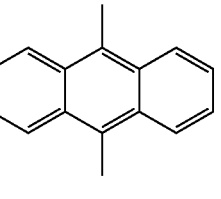 | 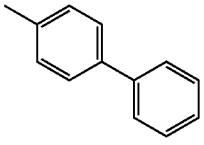 |
| 5 | 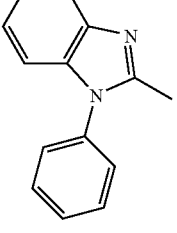 | 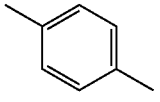 | 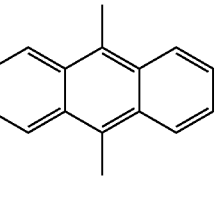 | 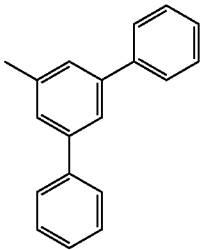 |
| 6 | 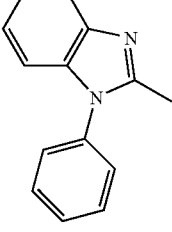 | 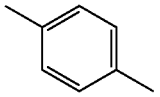 | 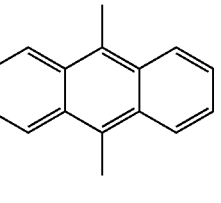 | 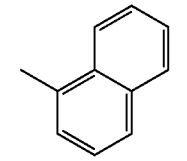 |
| 7 | 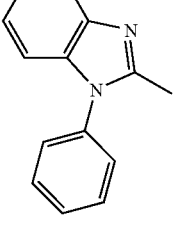 | 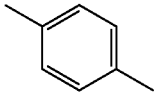 | 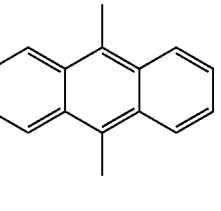 | 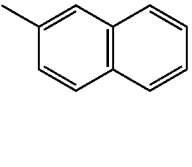 |
| 8 | 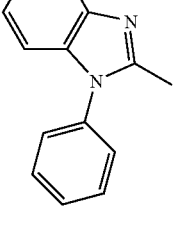 | 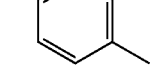 | 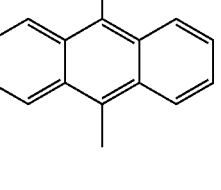 | 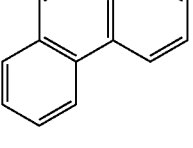 |

-continued
| | HAr | L | Ar¹ | Ar² |
|---|---|---|---|---|
| 9 | 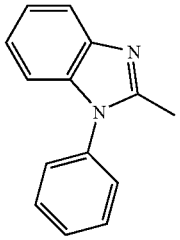 | 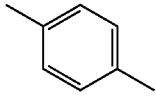 | 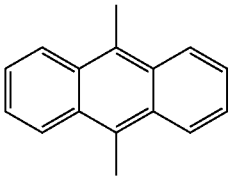 | 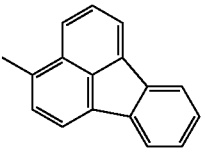 |
| 10 | 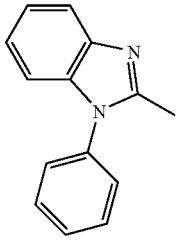 | 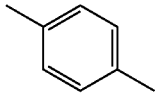 | 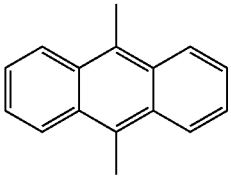 | 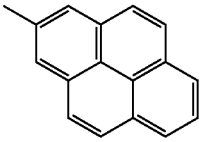 |
| 11 | 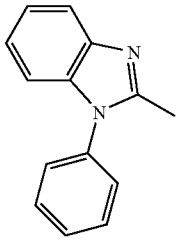 | 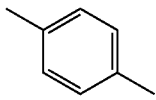 | 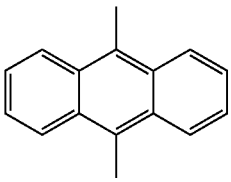 | 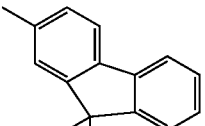 |
| 12 | 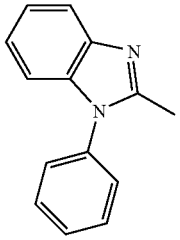 | 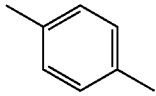 | 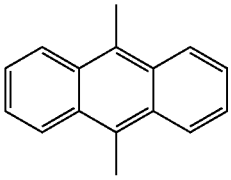 | 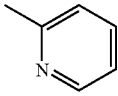 |
| 13 | 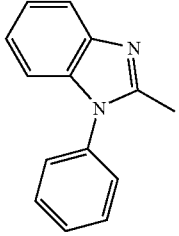 | 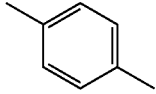 | 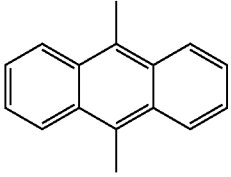 | 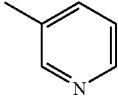 |
| 14 | 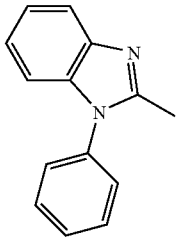 | 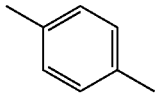 | 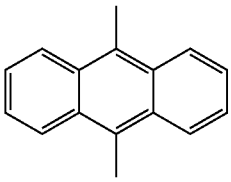 | 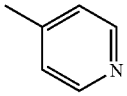 |

-continued
| | HAr | L | Ar¹ | Ar² |
|---|---|---|---|---|
| 2-1 | 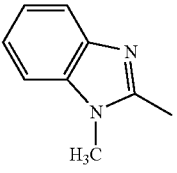 | 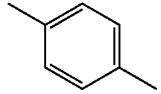 | 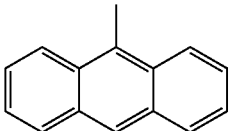 | 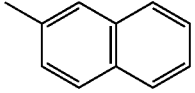 |
| 2 | 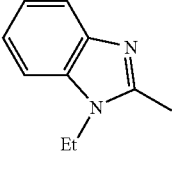 | 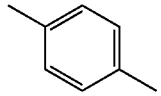 | 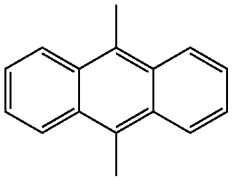 | 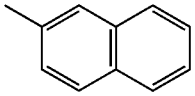 |
| 3 | 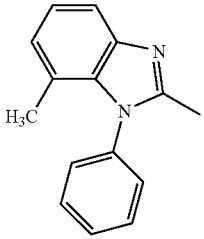 | 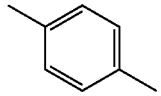 | 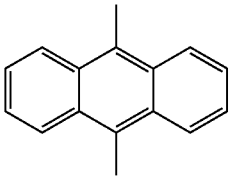 | 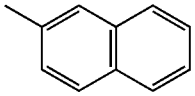 |
| 4 | 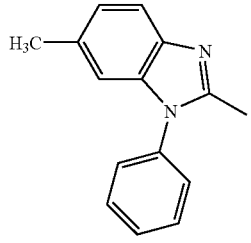 | 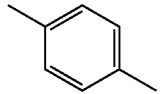 | 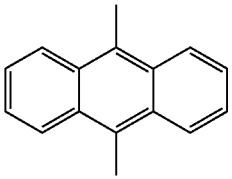 | 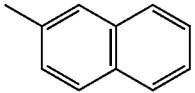 |
| 5 | 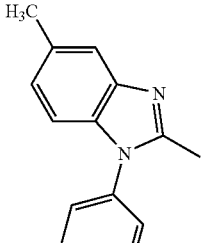 | 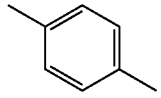 | 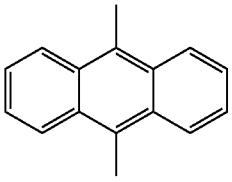 | 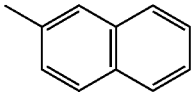 |
| 6 | 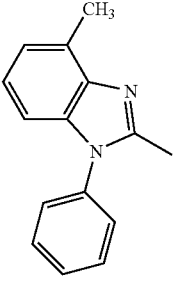 | 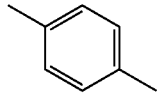 | 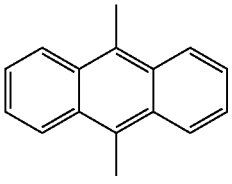 | 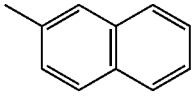 |

-continued
| | HAr | L | Ar¹ | Ar² |
|---|---|---|---|---|
| 7 | 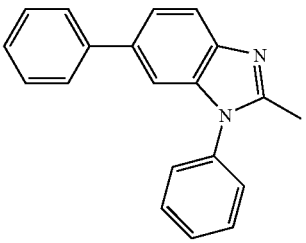 | 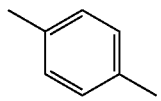 | 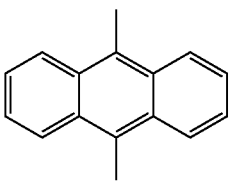 | 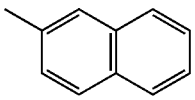 |
| 8 | 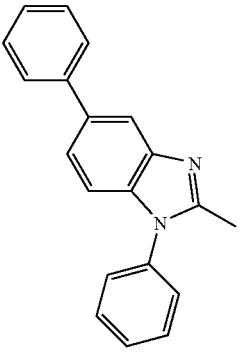 | 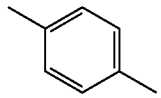 | 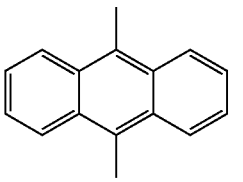 | 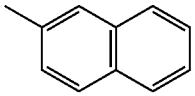 |
| 9 | 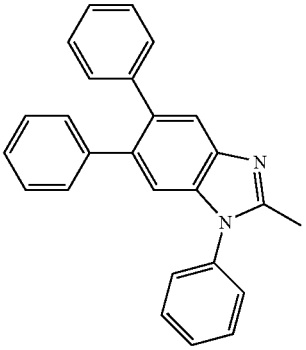 | 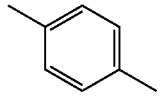 | 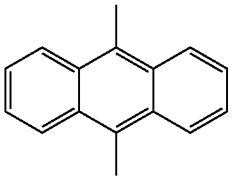 | 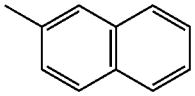 |
| 3-1 | 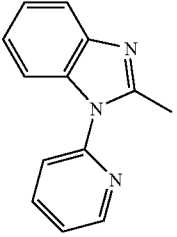 | 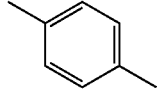 | 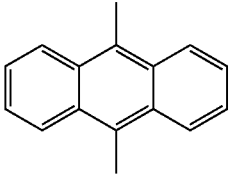 | 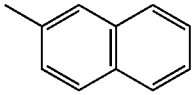 |
| 2 | 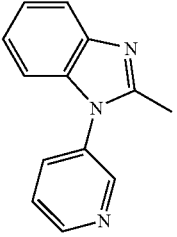 | 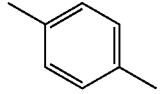 | 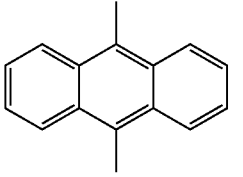 | 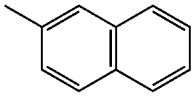 |

-continued
| | HAr | L | Ar¹ | Ar² |
|---|---|---|---|---|
| 3 | 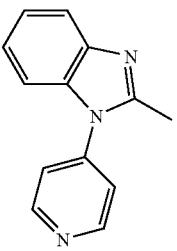 | 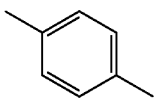 | 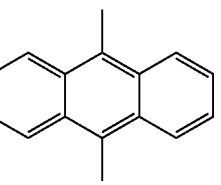 | 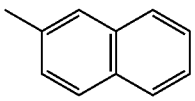 |
| 4 | 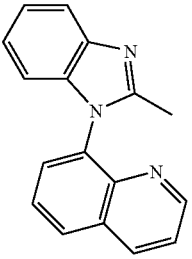 | 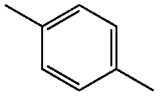 | 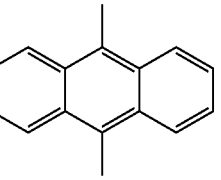 | 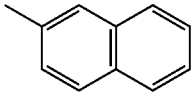 |
| 5 | 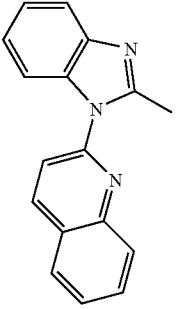 | 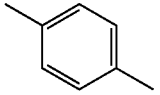 | 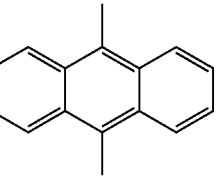 | 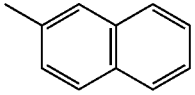 |
| 6 | 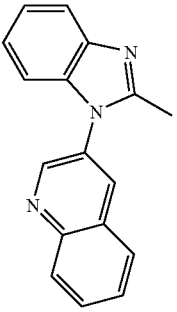 | 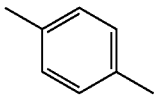 | 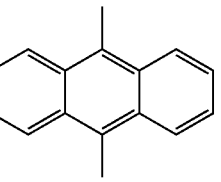 | 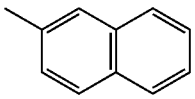 |
| 4-1 | 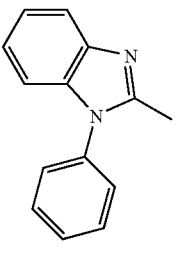 | — | 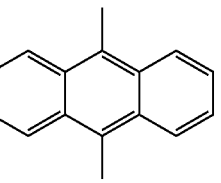 | 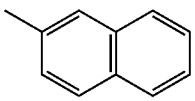 |

-continued
| | HAr | L | Ar¹ | Ar² |
|---|---|---|---|---|
| 2 | 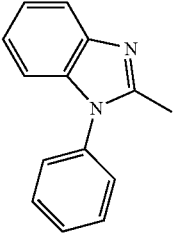 | 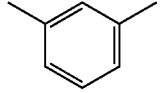 | 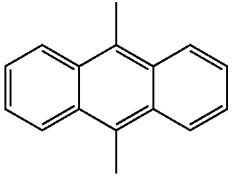 | 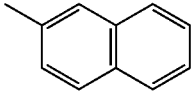 |
| 3 | 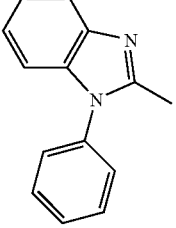 | 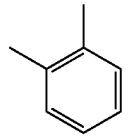 | 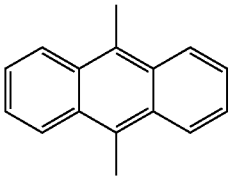 | 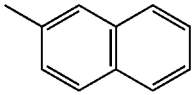 |
| 4 | 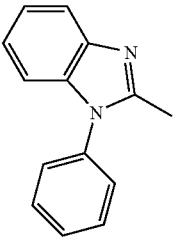 | 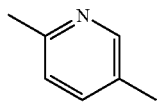 | 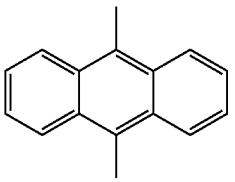 | 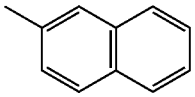 |
| 5 | 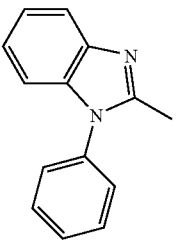 | 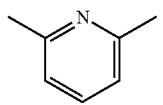 | 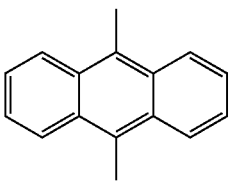 | 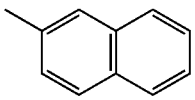 |
| 6 | 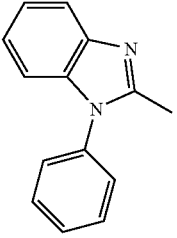 | 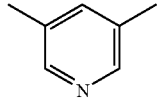 | 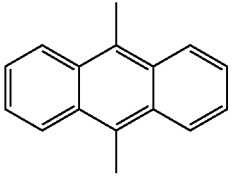 | 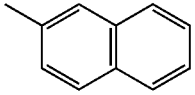 |
| 7 | 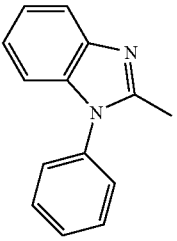 | 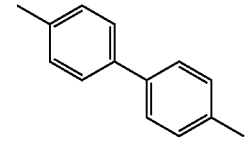 | 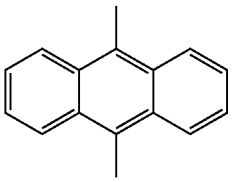 | 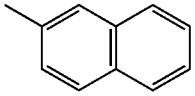 |

-continued
| | HAr | L | Ar¹ | Ar² |
|---|---|---|---|---|
| 8 | 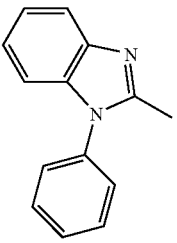 | 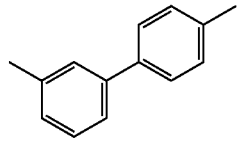 | 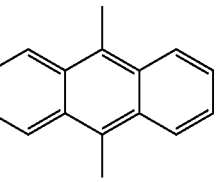 | 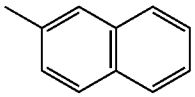 |
| 9 | 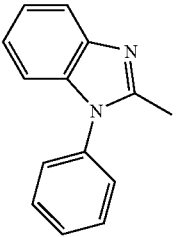 | 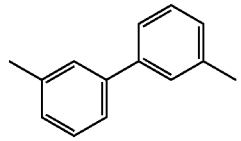 | 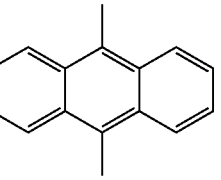 | 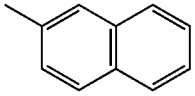 |
| 10 | 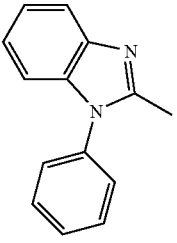 | 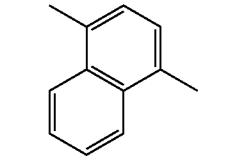 | 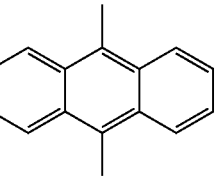 | 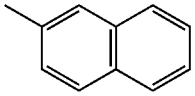 |
| 11 | 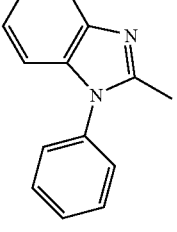 | 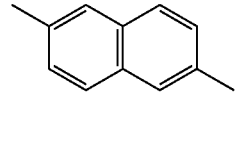 | 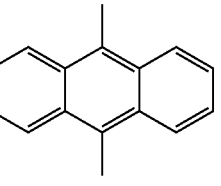 | 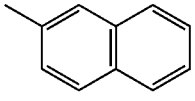 |
| 12 | 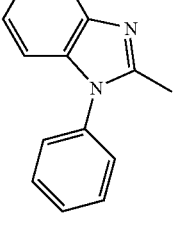 | 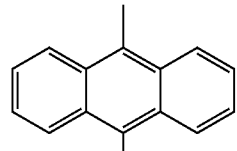 | 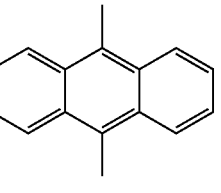 | 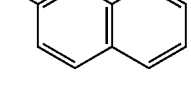 |
| 5-1 | 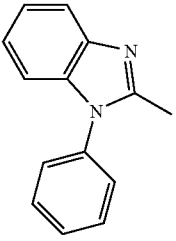 | 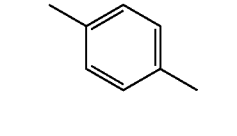 | 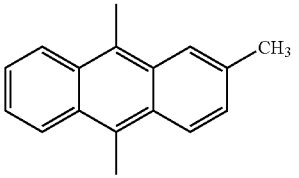 | 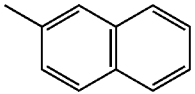 |

-continued
| | HAr | L | Ar¹ | Ar² |
|---|---|---|---|---|
| 2 | 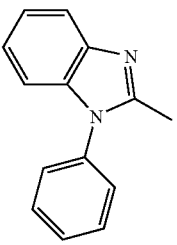 | 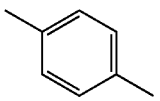 | 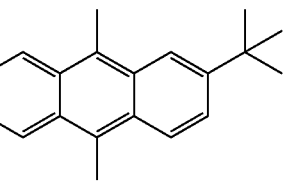 | 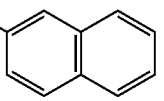 |
| 3 | 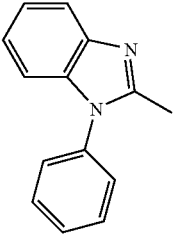 | 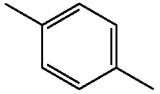 | 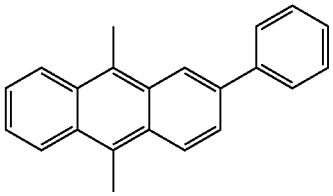 | 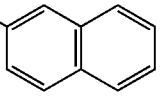 |
| 4 | 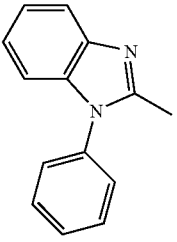 | 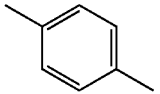 | 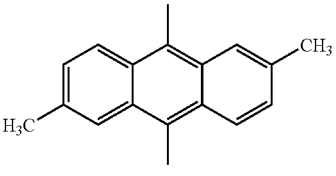 | 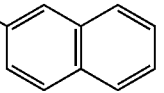 |
| 5 | 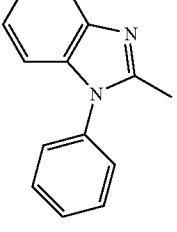 | 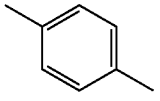 | 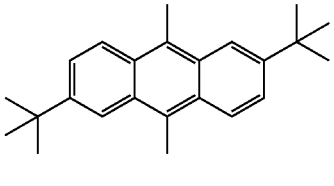 | 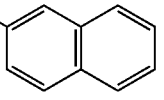 |
| 6 | 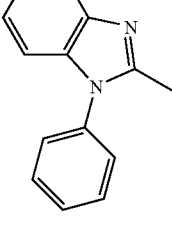 | 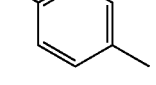 | 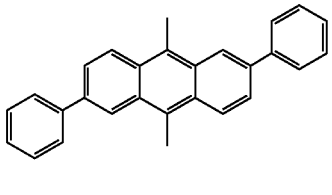 | 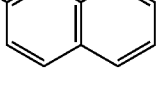 |
| 6-1 | 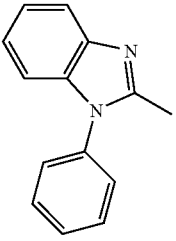 | 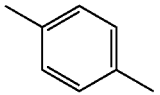 | 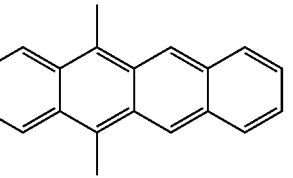 | 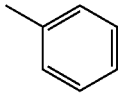 |

| | HAr | L | Ar¹ | Ar² |
|---|---|---|---|---|
| 2 | | | | |
| 3 | | | | |
| 4 | | | | |
| 5 | | | | |
| 7-1 | | | | |
| 2 | | | | |

-continued

| | HAr | L | Ar¹ | Ar² |
|---|---|---|---|---|
| 3 | | | | |
| 4 | | | | |
| 5 | | | | |
| 6 | | | | |
| 7 | | | | |
| 8 | | | | |

-continued

| | HAr | L | Ar¹ | Ar² |
|---|---|---|---|---|
| 9 | 1-methyl-2-phenyl-benzimidazole | p-phenylene | 9,10-anthracenyl | 2-naphthyl |
| 10 | 1,2-dimethyl-benzimidazole | p-phenylene | 9,10-anthracenyl | 2-naphthyl |
| 8-1 | 1-phenyl-2-methyl-benzimidazole | p-phenylene | p-phenylene | phenyl |
| 2 | 1-phenyl-2-methyl-benzimidazole | p-phenylene | m-phenylene | phenyl |
| 3 | 1-phenyl-2-methyl-benzimidazole | p-phenylene | 1,4-naphthyl | phenyl |
| 4 | 1-phenyl-2-methyl-benzimidazole | p-phenylene | 2,6-naphthyl | phenyl |

-continued
| | HAr | L | Ar¹ | Ar² |
|---|---|---|---|---|
| 5 | 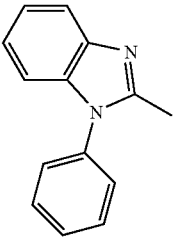 | 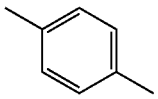 | 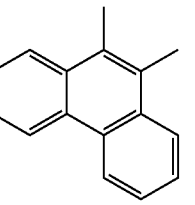 | 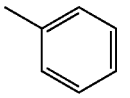 |
| 6 | 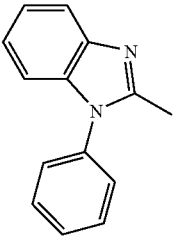 | 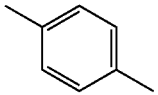 | 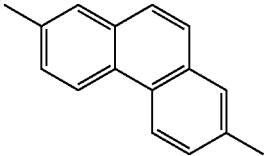 | 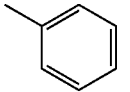 |
| 7 | 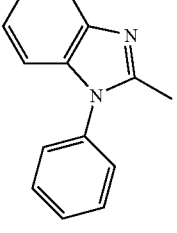 | 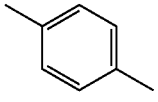 | 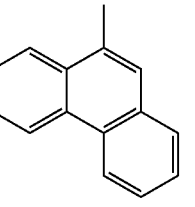 |  |
| 8 | 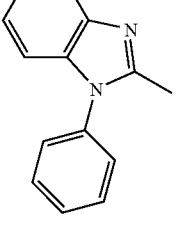 | 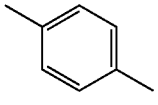 | 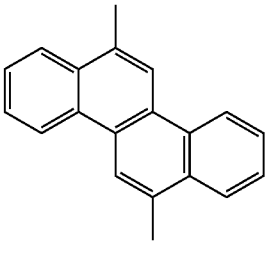 | 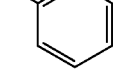 |
| 9 | 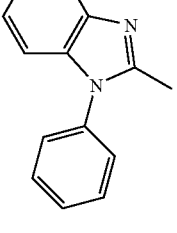 | 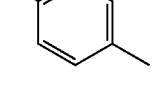 | 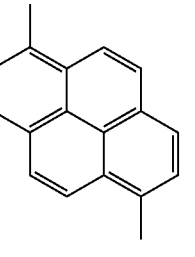 | 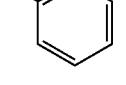 |
| 10 | 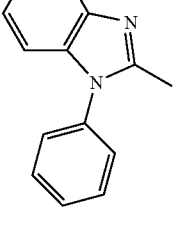 | 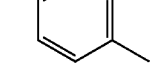 | 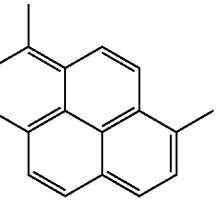 | 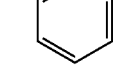 |

US 8,025,815 B2

111 112

-continued

| | HAr | L | Ar¹ | Ar² |
|---|---|---|---|---|
| 11 | 1-phenyl-2-methyl-benzimidazole | p-phenylene | pyrenyl | H |
| 12 | 1-phenyl-2-methyl-benzimidazole | p-phenylene | 10,10'-dimethyl-9,9'-bianthryl | phenyl |
| 13 | 1-phenyl-2-methyl-benzimidazole | p-phenylene | 1,4-bis(10-methylanthracen-9-yl)phenylene | phenyl |
| 9-1 | 1-methyl-2-phenyl-benzimidazole | p-phenylene | 10-methylanthracen-9-yl | phenyl |
| 2 | 1-methyl-2-phenyl-benzimidazole | p-phenylene | 10-methylanthracen-9-yl | 2-biphenyl |
| 3 | 1-methyl-2-phenyl-benzimidazole | p-phenylene | 10-methylanthracen-9-yl | 3-biphenyl |
| 4 | 1-methyl-2-phenyl-benzimidazole | p-phenylene | 10-methylanthracen-9-yl | 4-biphenyl |

-continued

| | HAr | L | Ar¹ | Ar² |
|---|---|---|---|---|
| 5 | 1-methyl-2-phenylbenzimidazole | 1,4-phenylene | 9,10-anthracenediyl | 3,5-diphenylphenyl |
| 6 | 1-methyl-2-phenylbenzimidazole | 1,4-phenylene | 9,10-anthracenediyl | 1-naphthyl |
| 7 | 1-methyl-2-phenylbenzimidazole | 1,4-phenylene | 9,10-anthracenediyl | 2-naphthyl |
| 8 | 1-methyl-2-phenylbenzimidazole | 1,4-phenylene | 9,10-anthracenediyl | phenanthrenyl |
| 9 | 1-methyl-2-phenylbenzimidazole | 1,4-phenylene | 9,10-anthracenediyl | fluoranthenyl |
| 10 | 1-methyl-2-phenylbenzimidazole | 1,4-phenylene | 9,10-anthracenediyl | pyrenyl |
| 11 | 1-methyl-2-phenylbenzimidazole | 1,4-phenylene | 9,10-anthracenediyl | 9,9-dimethylfluorenyl |

-continued
| | HAr | L | Ar¹ | Ar² |
|---|---|---|---|---|
| 12 | 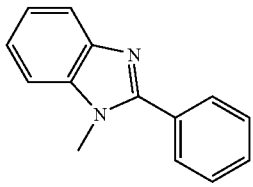 | 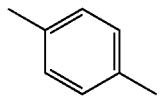 | 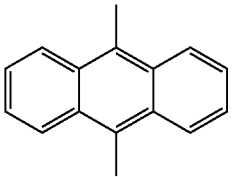 | 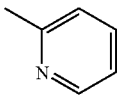 |
| 13 | 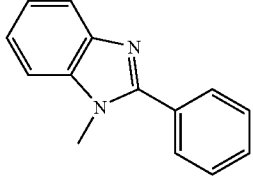 | 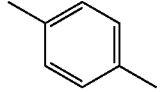 | 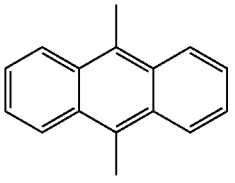 | 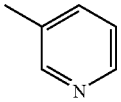 |
| 14 | 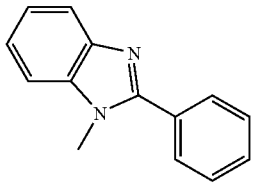 | 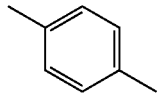 | 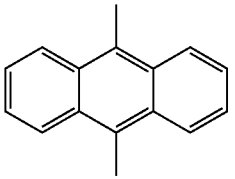 | 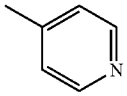 |
| 10-1 | 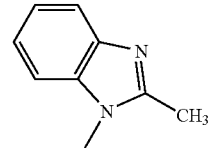 | 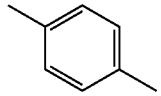 | 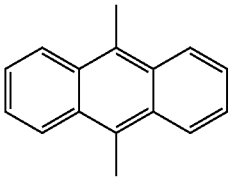 | 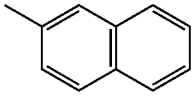 |
| 2 | 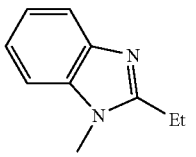 | 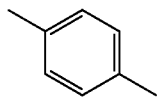 | 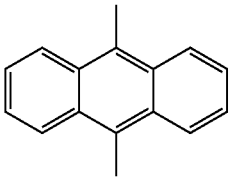 | 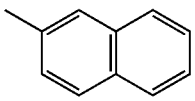 |
| 3 | 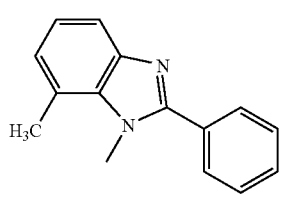 | 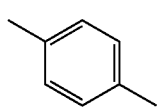 | 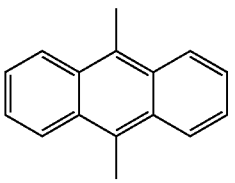 | 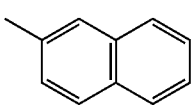 |
| 4 | 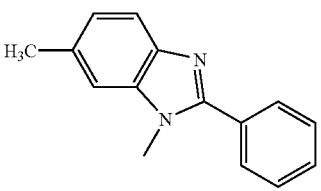 | 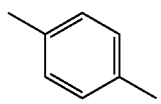 | 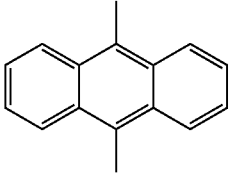 | 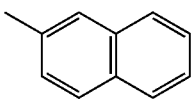 |

-continued

| | HAr | L | Ar¹ | Ar² |
|---|---|---|---|---|
| 5 | 5-methyl-1-methyl-2-phenylbenzimidazole | p-phenylene | 9,10-dimethylanthracene-linked | 2-naphthyl |
| 6 | 4-methyl-1-methyl-2-phenylbenzimidazole | p-phenylene | 9,10-dimethylanthracene-linked | 2-naphthyl |
| 7 | 6-phenyl-1-methyl-2-phenylbenzimidazole | p-phenylene | 9,10-dimethylanthracene-linked | 2-naphthyl |
| 8 | 5-phenyl-1-methyl-2-phenylbenzimidazole | p-phenylene | 9,10-dimethylanthracene-linked | 2-naphthyl |
| 9 | 5,6-diphenyl-1-methyl-2-phenylbenzimidazole | p-phenylene | 9,10-dimethylanthracene-linked | 2-naphthyl |
| 11-1 | 1-methyl-2-(2-pyridyl)benzimidazole | p-phenylene | 9,10-dimethylanthracene-linked | 2-naphthyl |

-continued
| | HAr | L | Ar¹ | Ar² |
|---|---|---|---|---|
| 2 | 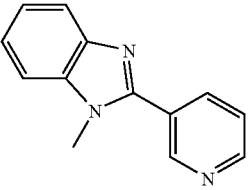 | 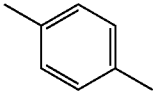 | 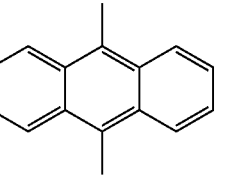 | 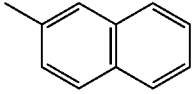 |
| 3 | 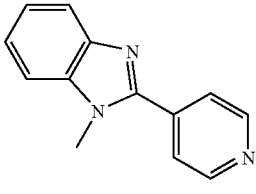 | 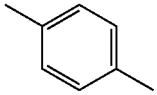 | 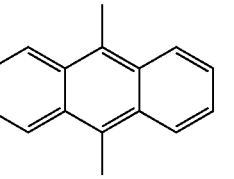 | 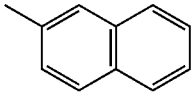 |
| 4 | 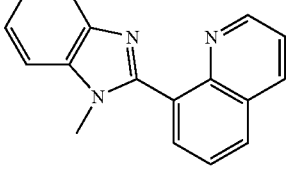 | 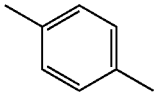 | 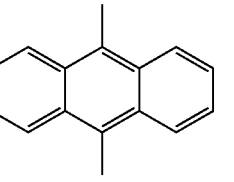 | 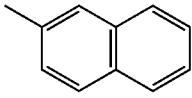 |
| 5 | 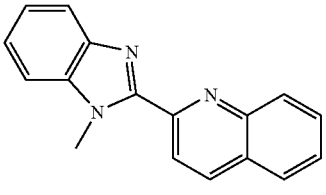 | 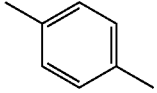 | 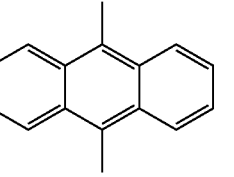 | 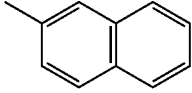 |
| 6 | 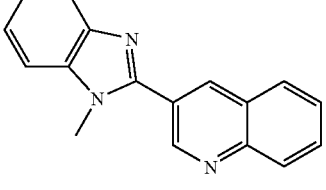 | 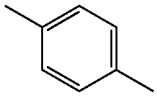 | 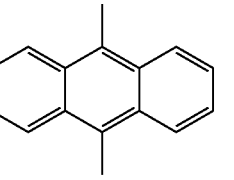 | 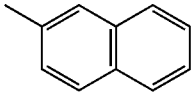 |
| 12-1 | 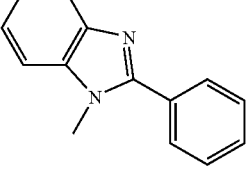 | | 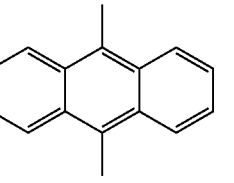 | 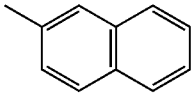 |
| 2 | 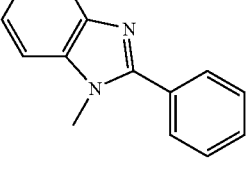 | 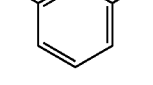 | 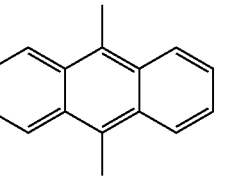 | 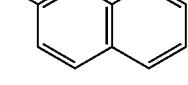 |

-continued
| | HAr | L | Ar¹ | Ar² |
|---|---|---|---|---|
| 3 | 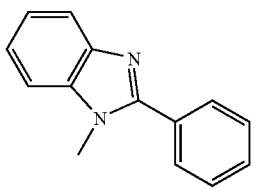 | 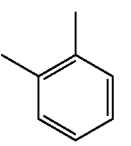 | 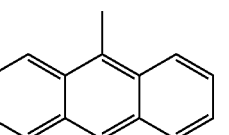 | 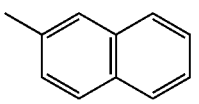 |
| 4 | 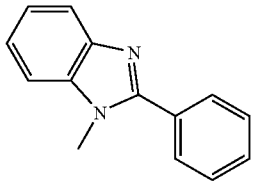 | 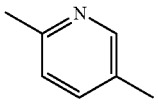 | 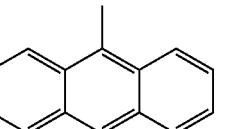 | 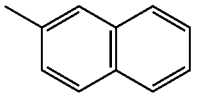 |
| 5 | 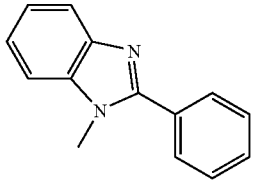 | 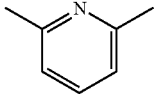 | 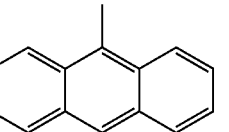 | 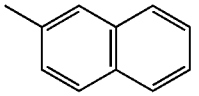 |
| 6 | 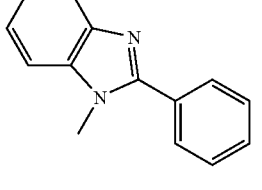 | 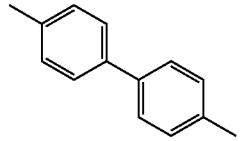 | 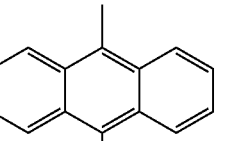 | 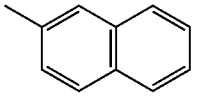 |
| 7 | 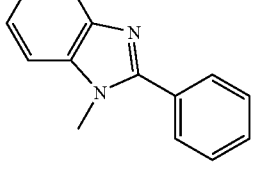 | 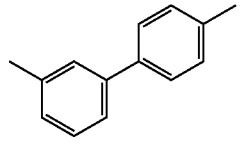 | 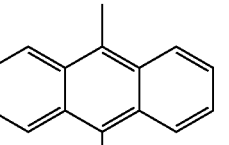 | 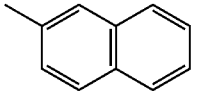 |
| 8 | 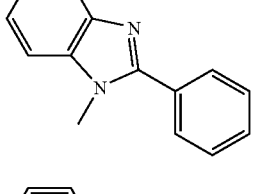 | 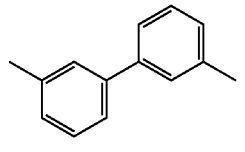 | 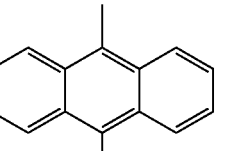 | 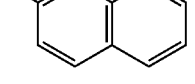 |
| 9 | 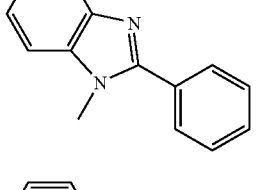 | 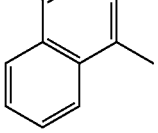 | 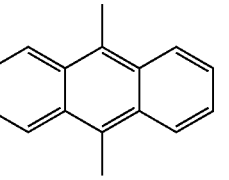 | 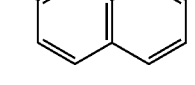 |
| 10 | 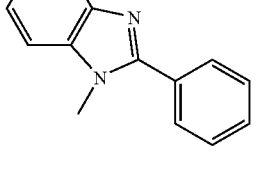 | 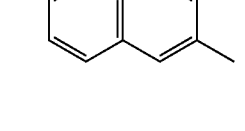 | 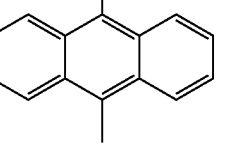 | 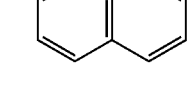 |

-continued

| | HAr | L | Ar¹ | Ar² |
|---|---|---|---|---|
| 11 | | | | |
| 13-1 | | | | |
| 2 | | | | |
| 3 | | | | |
| 4 | | | | |
| 5 | | | | |
| 6 | | | | |

-continued
| | HAr | L | Ar¹ | Ar² |
|---|---|---|---|---|
| 14-1 | 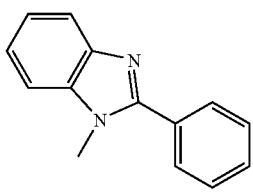 | 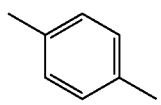 | 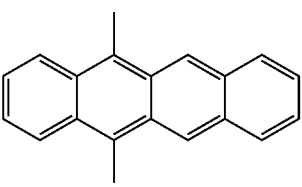 | 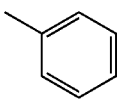 |
| 2 | 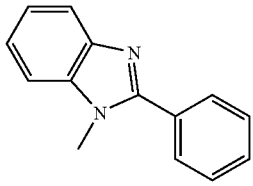 | 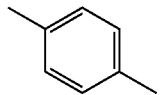 | 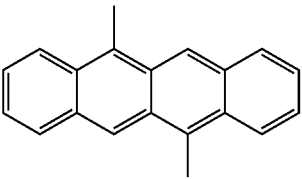 | 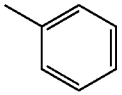 |
| 3 | 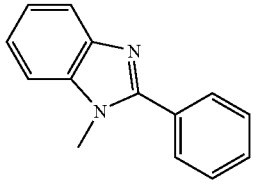 | 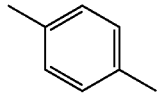 | 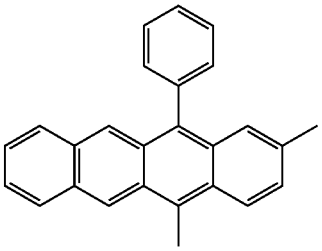 | 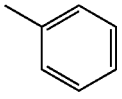 |
| 4 | 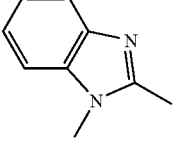 | 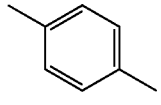 | 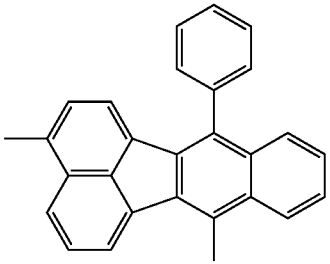 | 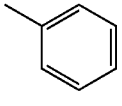 |
| 5 | 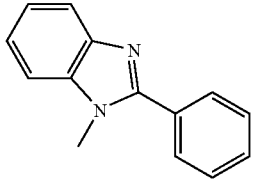 | 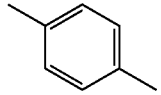 | 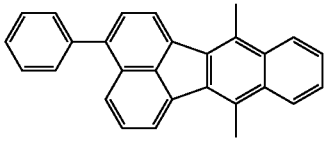 | 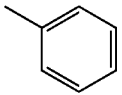 |
| 15-1 | 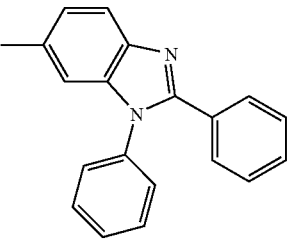 |  | 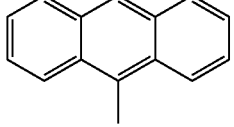 | 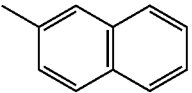 |

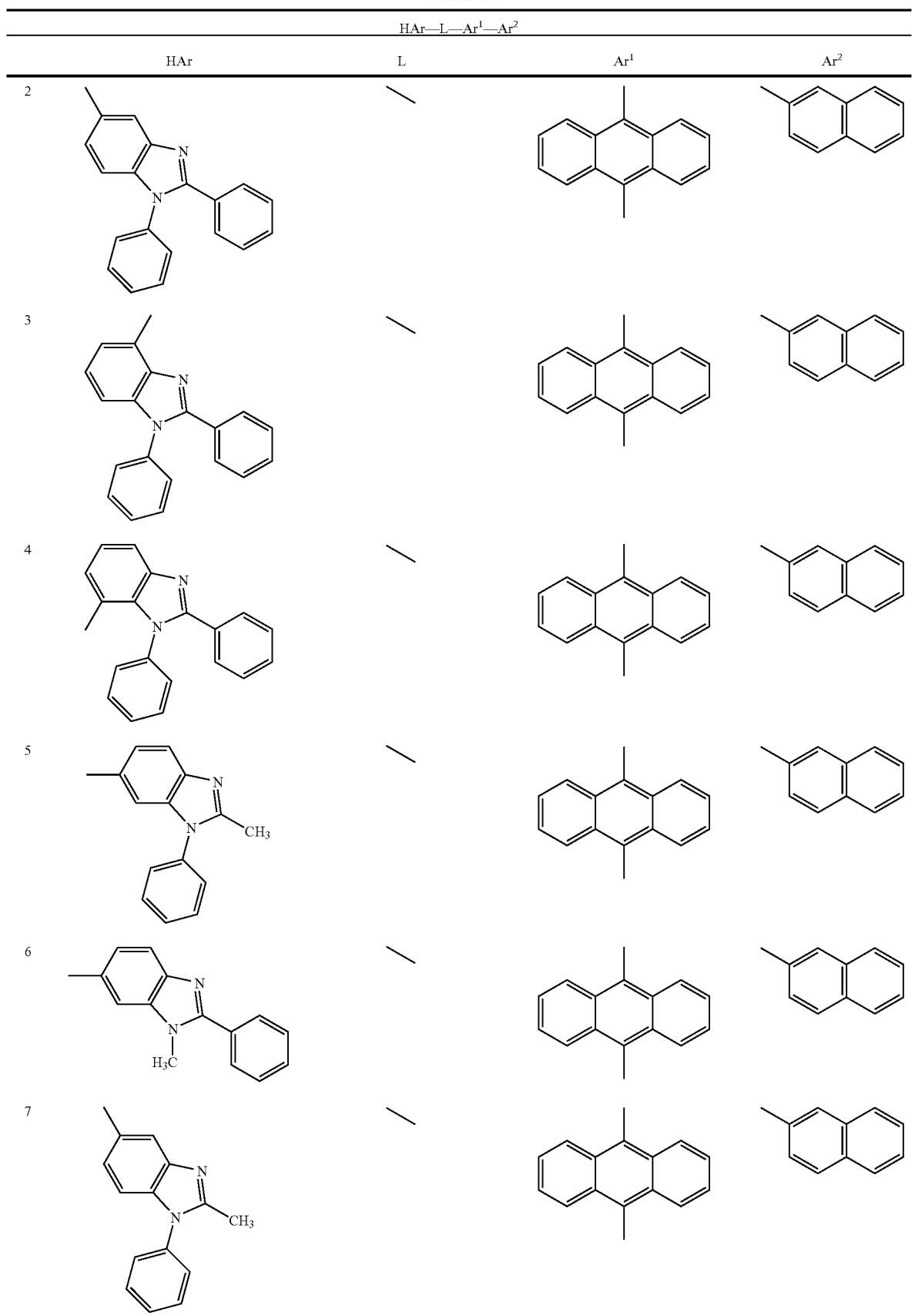

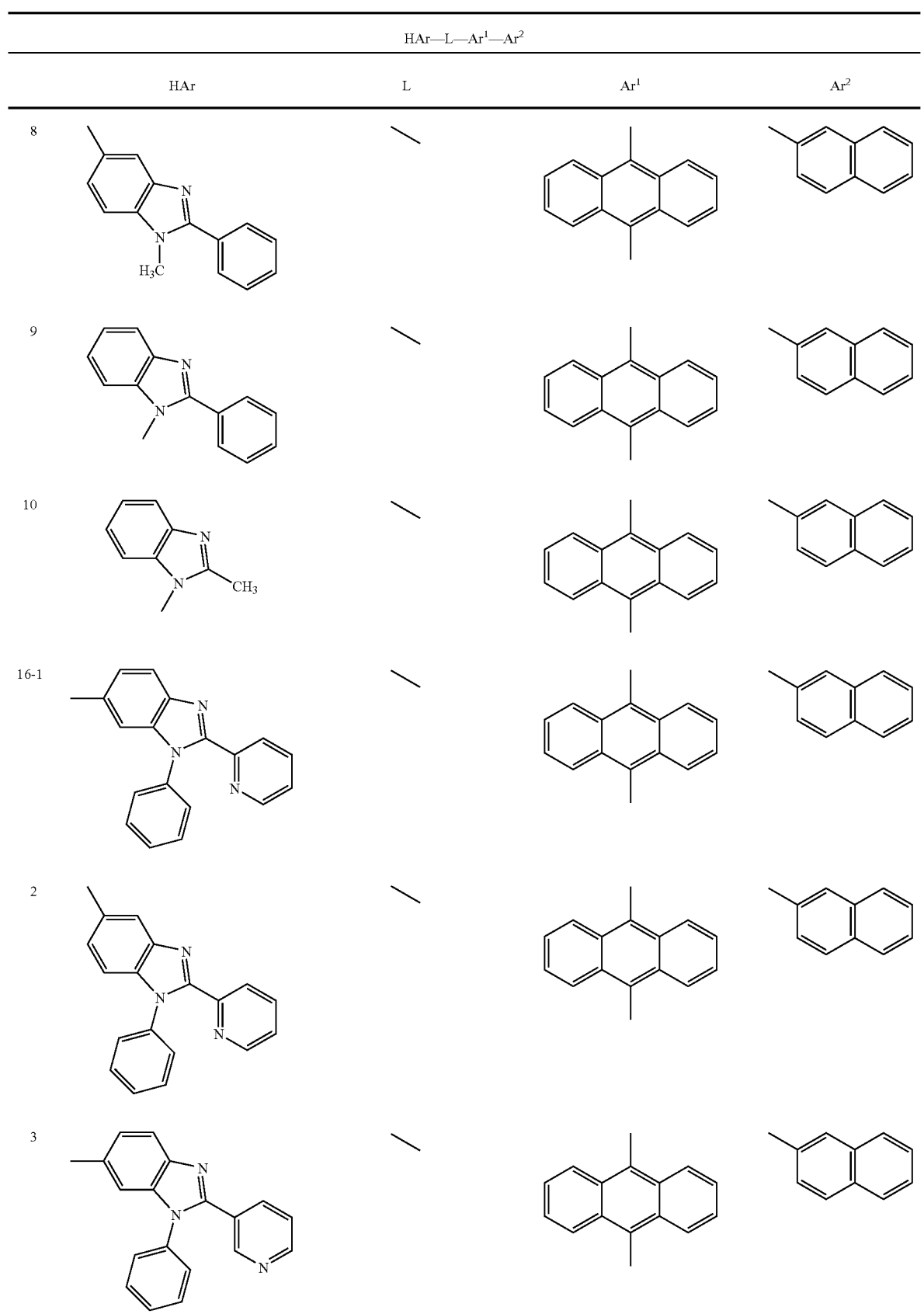

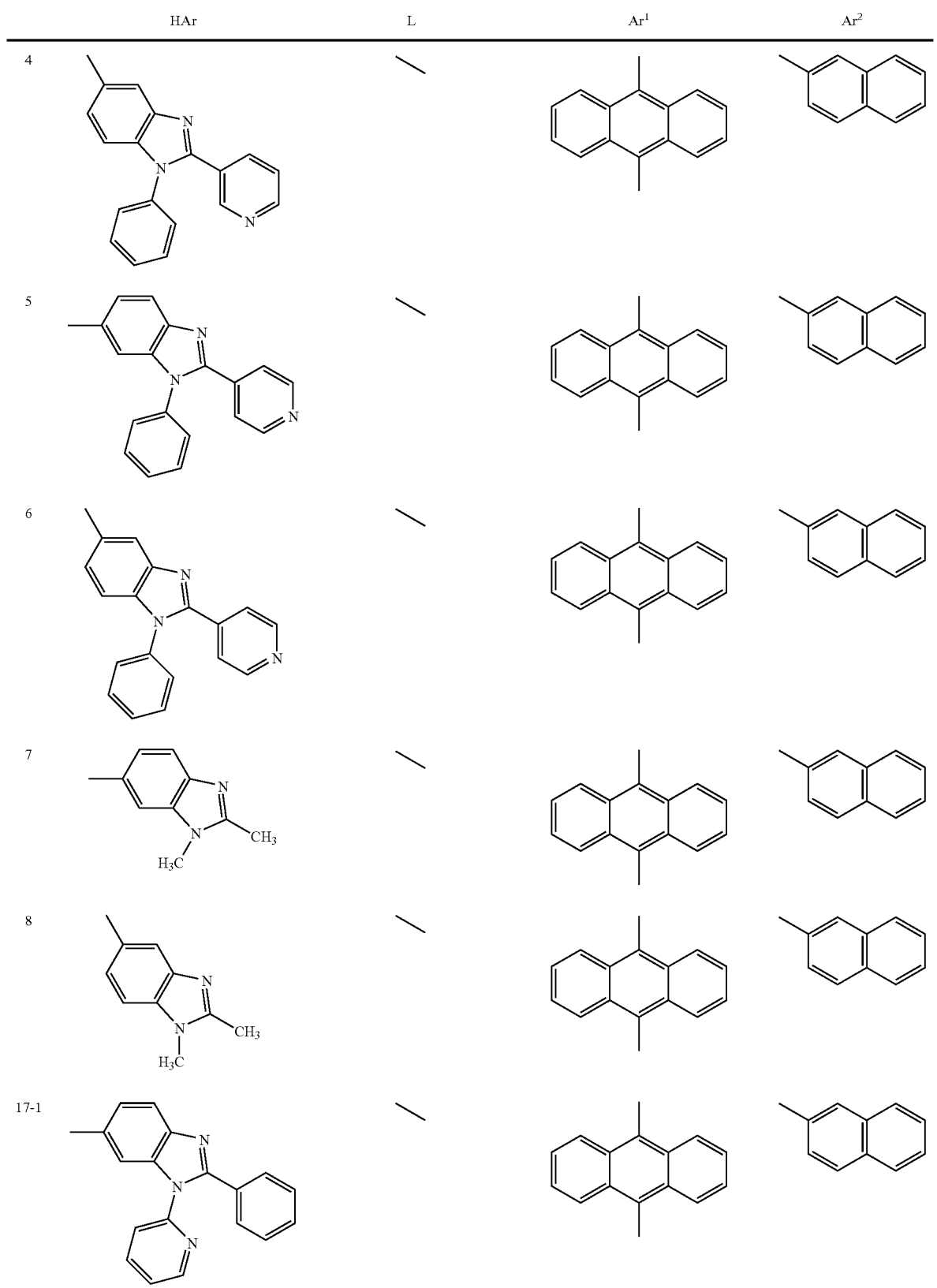

-continued
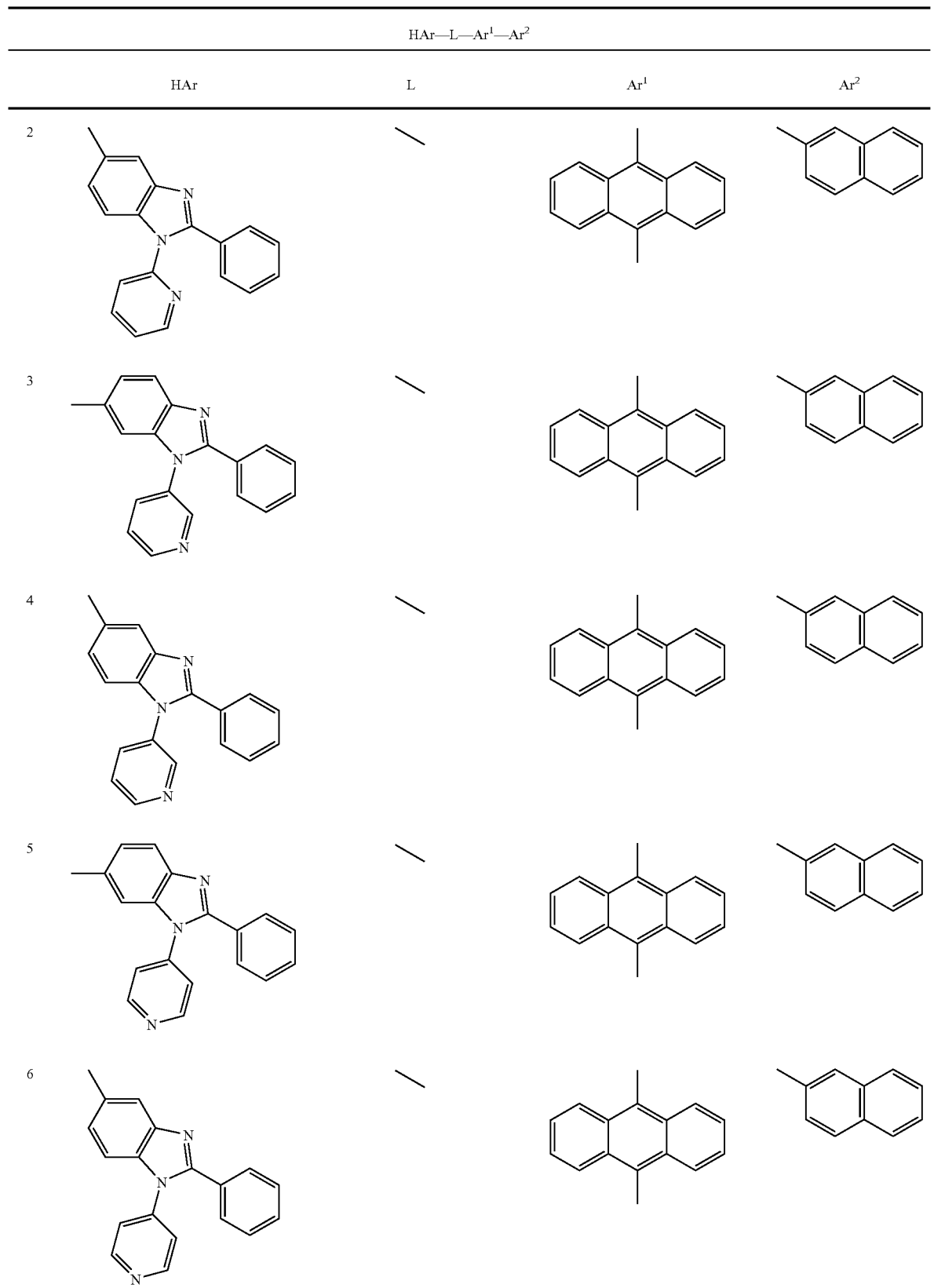

-continued

| HAr—L—Ar¹—Ar² | | | |
|---|---|---|---|
| HAr | L | Ar¹ | Ar² |

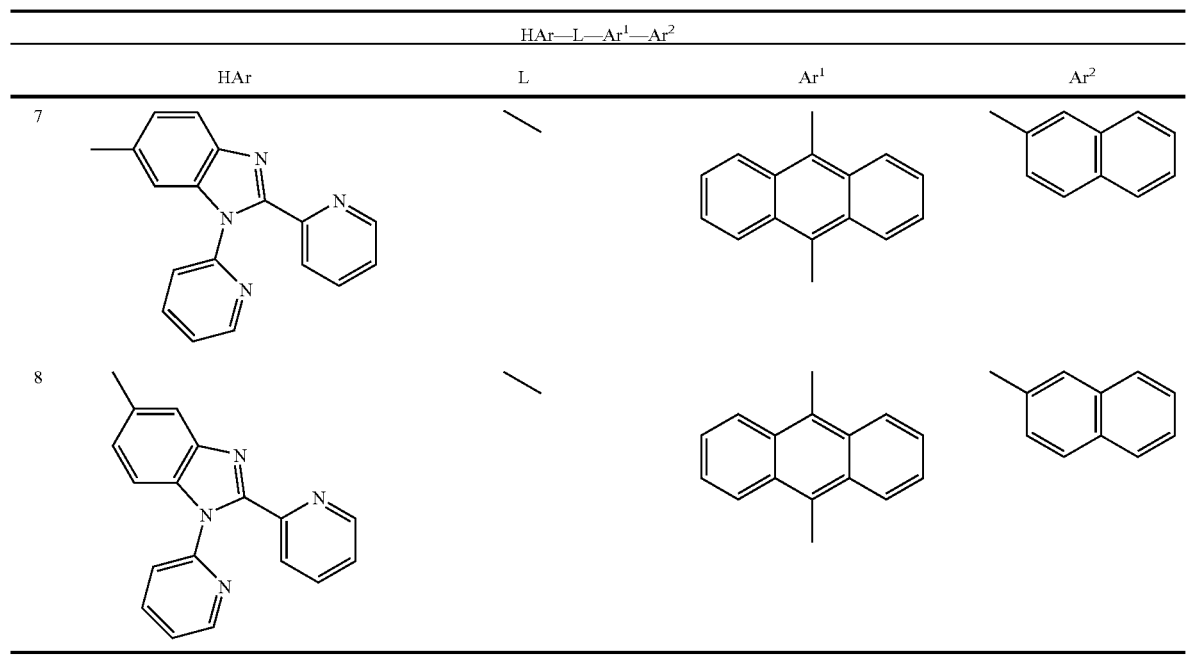

Among the above examples, examples (1-1), (1-5), (1-7), (2-1), (3-1), (4-2), (4-6), (7-2), (7-7), (7-8), (7-9), (9-1) and (9-7) are particularly preferred.

Although thickness of the electron injecting layer or the electron transporting layer is not specifically limited, the thickness is preferably 1 to 100 nm.

The electron injecting layer preferably contains an inorganic compound such as an insulator or a semiconductor in addition to the nitrogen-containing cyclic derivative. Such an insulator or a semiconductor, when contained in the electron injecting layer, can effectively prevent a current leak, thereby enhancing electron injectability of the electron injecting layer.

As the insulator, it is preferable to use at least one metal compound selected from a group consisting of an alkali metal chalcogenide, an alkali earth metal chalcogenide, a halogenide of alkali metal and a halogenide of alkali earth metal. By forming the electron injecting layer from the alkali metal chalcogenide or the like, the electron injecting capability can preferably be further enhanced. Specifically, preferable examples of the alkali metal chalcogenide are $Li_2O$, $K_2O$, $Na_2S$, $Na_2Se$ and $Na_2O$, while preferable example of the alkali earth metal chalcogenide are CaO, BaO, SrO, BeO, BaS and CaSe. Preferable examples of the halogenide of the alkali metal are LiF, NaF, KF, LiCl, KCl and NaCl. Preferable examples of the halogenide of the alkali earth metal are fluorides such as $CaF_2$, $BaF_2$, $SrF_2$, $MgF_2$ and $BeF_2$, and halogenides other than the fluoride.

Examples of the semiconductor are one of or a combination of two or more of an oxide, a nitride or an oxidized nitride containing at least one element selected from a group consisting of Ba, Ca, Sr, Yb, Al, Ga, In, Li, Na, Cd, Mg, Si, Ta, Sb and Zn. The inorganic compound for forming the electron injecting layer is preferably a microcrystalline or amorphous insulator film. When the electron injecting layer is formed of such insulator film, more uniform thin film can be formed, thereby reducing pixel defects such as a dark spot. Examples of such an inorganic compound are the above-described alkali metal chalcogenide, alkali earth metal chalcogenide, halogenide of the alkali metal and halogenide of the alkali earth metal.

The electron injecting layer according to the present invention may preferably contain the above-described reductive dopant.

The hole injecting layer or the hole transporting layer (including the hole injecting/transporting layer) may contain an aromatic amine compound such as an aromatic amine derivative represented by the following general formula (I).

(I)

In the above formula (I), $Ar^1$ to $Ar^4$ each represent a substituted or unsubstituted aryl group having 6 to 50 carbon atoms forming a ring or a substituted or unsubstituted heteroaryl group having 5 to 50 atoms forming a ring.

Examples of the substituted or unsubstituted aryl group having 6 to 50 ring carbon atoms are a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, fluoranthenyl group, fluorenyl group and the like.

Examples of the substituted or unsubstituted heteroaryl group having 5 to 50 ring atoms are a 1-pyroryl group, 2-pyroryl group, 3-pyroryl group, pyrazinyl group, 2-pyridiny group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthrydinyl group, 2-phenanthrydinyl group, 3-phenanthrydinyl group, 4-phenanthrydinyl group, 6-phenanthrydinyl group, 7-phenanthrydinyl group, 8-phenanthrydinyl group, 9-phenanthrydinyl group, 10-phenanthrydinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-3-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group and the like. Among the above, a phenyl group, a naphthyl group, biphenyl group, anthranil group, phenanthryl group, pyrenyl group, chrysenyl group, fluoranthenyl group, fluorenyl group and the like are preferable.

L represents a link group. Specifically, L represents a substituted or unsubstituted arylene group having 6 to 50 carbon atoms forming a ring, a substituted or unsubstituted heteroarylene group having 5 to 50 atoms forming a ring, a divalent group formed by singly bonding, ether-bonding or thioether-bonding two or more arylene groups, a divalent group formed by bonding two or more arylene groups by alkylene group having 1 to 20 carbon atoms, alkenylene group having 2 to 20 carbon atoms or amino group, a divalent group formed by singly bonding, ether-bonding or thioether-bonding two or more heteroarylene groups, or a divalent group formed by bonding two or more heteroarylene groups by alkylene group having 1 to 20 carbon atoms, alkenylene group having 2 to 20 carbon atoms or amino group. Examples of the arylene group having 6 to 50 ring carbon atoms are a 1,4-phenylene group, 1,2-phenylene group, 1,3-phenylene group, 1,4-naphthylene group, 2,6-naphthylene group, 1,5-naphthylene group, 9,10-anthranylene group, 9,10-phenanthrenylene group, 3,6-phenanthrenylene group, 1,6-pyrenylene group, 2,7-pyrenylene group, 6,12-chrysenylene group, 4-4'-biphenylene group, 3,3'-biphenylene group, 2,2'-biphenylene group, 2,7-fluorenylene group and the like. Examples of the arylene group having 5 to 50 ring atoms are a 2,5-thiophenylene group, 2,5-silolylene group, 2,5-oxadiazolylene and the like. Among the above, a 1,4-phenylene group, 1,2-phenylene group, 1,3-phenylene group, 1,4-naphthylene group, 9,10-anthranylene group, 6,12-chrysenylene group, 4-4'-biphenylene group, 3,3'-biphenylene group, 2,2'-biphenylene group, and 2,7-fluorenylene group are preferable.

When L represents a link group formed of 2 or more arylene groups or 2 or more heteroarylene groups, adjacent arylene groups or adjacent heteroarylene groups may be bonded together via a divalent group to form a new ring. Examples of the divalent group for forming the ring are a tetramethylene group, a pentamethylene group, a hexamethylene group, a diphenylmethane-2,2'-diyl group, a diphenylethane-3,3'-diyl group, a diphenylpropane-4,4'-diyl group and the like.

Examples of a substituent for each of $Ar^1$ to $Ar^4$ and L are an amino group, a halogen group, a cyano group, a nitro group and a hydroxy group each of which is substituted by a substituted or unsubstituted aryl group having 6 to 50 carbon atoms forming a ring, a substituted or unsubstituted heteroaryl group having 5 to 50 atoms forming a ring, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 carbon atoms forming a ring, a substituted or unsubstituted heteroaryloxy group having 5 to 50 carbon atoms forming a ring, a substituted or unsubstituted arylthio group having 6 to 50 atoms forming a ring, a substituted or unsubstituted heteroarylthio group having 5 to 50 atoms forming a ring, a substituted or unsubstituted alkoxycarbonyl group having 2 to 50 carbon atoms, a substituted or unsubstituted aryl group having 6 to 50 carbon atoms forming a ring, or a substituted or unsubstituted heteroaryl group having 5 to 50 atoms forming a ring.

Examples of the substituted or unsubstituted aryl group having 6 to 50 ring carbon atoms are a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, fluoranthenyl group, fluorenyl group and the like.

Examples of the substituted or unsubstituted heteroaryl group having 5 to 50 ring atoms are a 1-pyroryl group, 2-pyroryl group, 3-pyroryl group, pyrazinyl group, 2-pyridiny group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthrydinyl group, 2-phenanthrydinyl group, 3-phenanthrydinyl group, 4-phenanthrydinyl group, 6-phenanthrydinyl group, 7-phenanthrydinyl group, 8-phenanthrydinyl group, 9-phenanthrydinyl group, 10-phenanthrydinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-3-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group and the like.

Examples of the substituted or unsubstituted alkyl group having 1 to 50 carbon atoms are a methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group and 1,2,3-trinitropropyl group.

Examples of the substituted or unsubstituted cycloalkyl group having 3 to 50 carbon atoms are a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group and the like.

The substituted or unsubstituted alkoxy group having 1 to 50 carbon atoms is a group represented by —OY. Examples of Y are a methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydoroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group and 1,2,3-trinitropropyl group.

Examples of the substituted or unsubstituted aralkyl group having 7 to 50 carbon atoms are a benzyl group, 1-phenylethyl group, 2-phenylethyl group, 1-phenylisopropyl group, 2-phenylisopropyl group, phenyl-t-butyl group, a-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrorylmethyl group, 2-(1-pyroryl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, 1-chloro-2-phenylisopropyl group and the like.

The substituted or unsubstituted aryloxy group having 6 to 50 ring carbon atoms is represented by —OY'. Preferable examples of Y' are a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group) 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group and the like.

The substituted or unsubstituted heteroaryloxy group having 5 to 50 ring atoms is represented by —OZ'. Examples of Z' are a 2-pyroryl group, 3-pyroryl group, pyrazinyl group, 2-pyridiny group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthrydinyl group, 2-phenanthrydinyl group, 3-phenanthrydinyl group, 4-phenanthrydinyl group, 6-phenanthrydinyl group, 7-phenanthrydinyl group, 8-phenanthrydinyl group, 9-phenanthrydinyl group, 10-phenanthrydinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-3-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group and the like.

The substituted or unsubstituted arylthio group having 6 to 50 ring carbon atoms is represented by —SY". Preferable examples of Y" are a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group and the like.

The substituted or unsubstituted heteroarylthio group is represented by —SZ". Examples of Z" are a 2-pyroryl group, 3-pyroryl group, pyrazinyl group, 2-pyridiny group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthrydinyl group, 2-phenanthrydinyl group, 3-phenanthrydinyl group, 4-phenanthrydinyl group, 6-phenanthrydinyl group, 7-phenanthrydinyl group, 8-phenanthrydinyl group, 9-phenanthrydinyl group, 10-phenanthrydinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-3-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group and the like.

The alkoxycarbonyl group having 2 to 50 carbon atoms is a group represented by —COOZ. Examples of Z are a methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydoroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromo ethyl group, 2-bromo ethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group and 1,2,3-trinitropropyl group.

The amino group substituted by the substituted or unsubstituted aryl group having 6 to 50 ring carbon atoms or the substituted or unsubstituted heteroaryl group having 5 to 50 ring atoms is represented by —NPQ. Examples of P and Q are a phenyl group, 1-naphthyl group, 2-naphtyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl) phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, 2-pyroryl group, 3-pyroryl group, pyrazinyl group, 2-pyridiny group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthrydinyl group, 2-phenanthrydinyl group, 3-phenanthrydinyl group, 4-phenanthrydinyl group, 6-phenanthrydinyl group, 7-phenanthrydinyl group, 8-phenanthrydinyl group, 9-phenanthrydinyl group, 10-phenanthrydinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group and the like.

Examples of the compound represented by the general formula (I) are shown below. However, the compound represented by the formula (I) is not limited thereto.

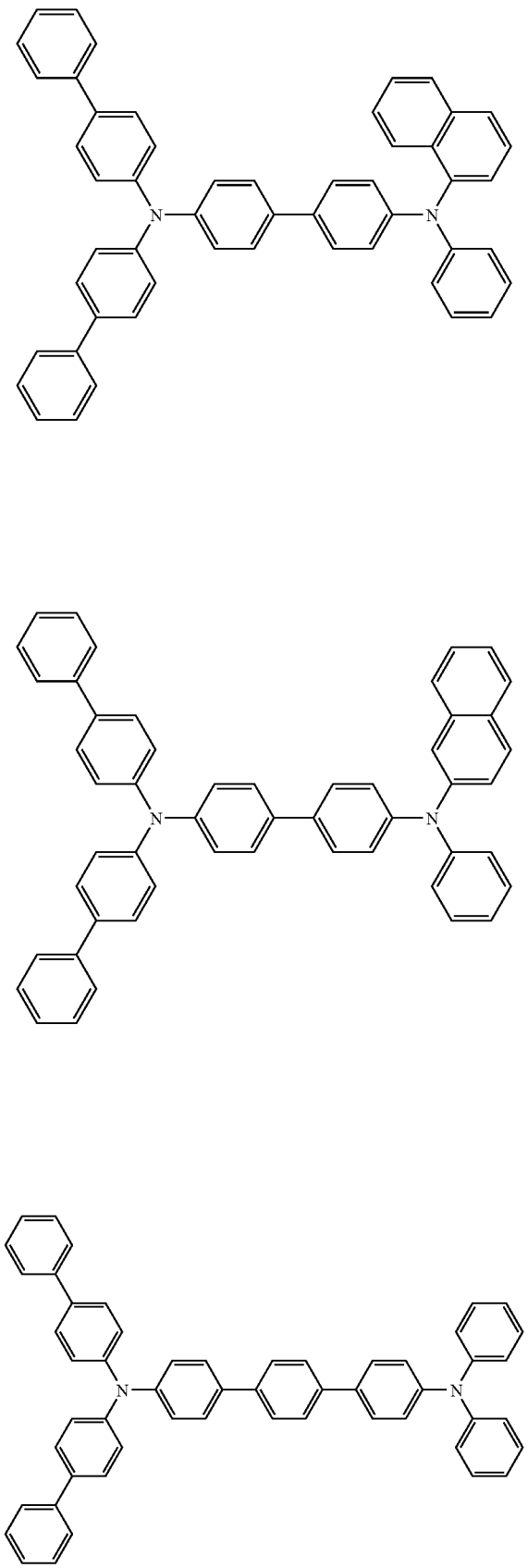

147
-continued
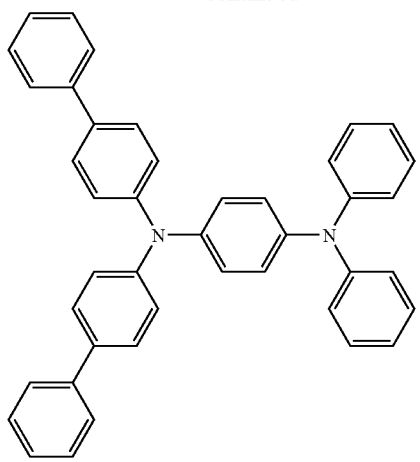
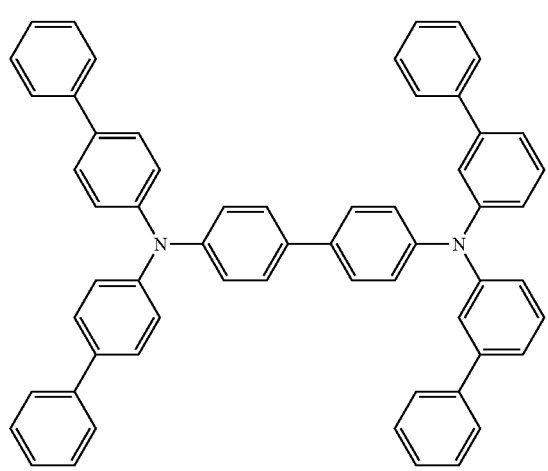
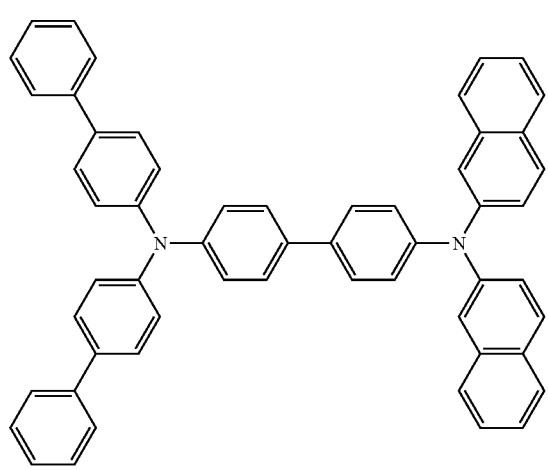
148
-continued
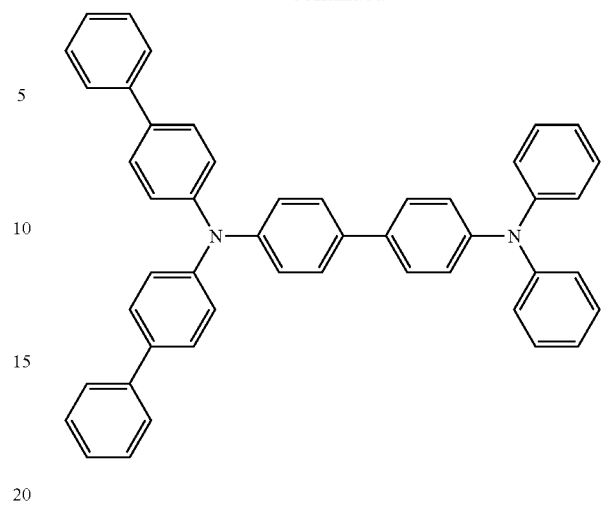
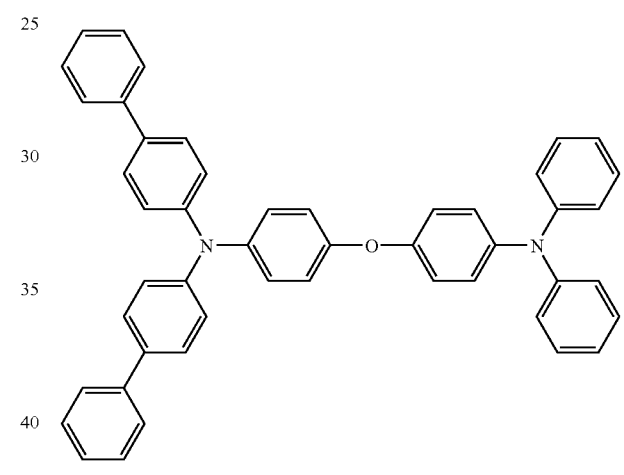
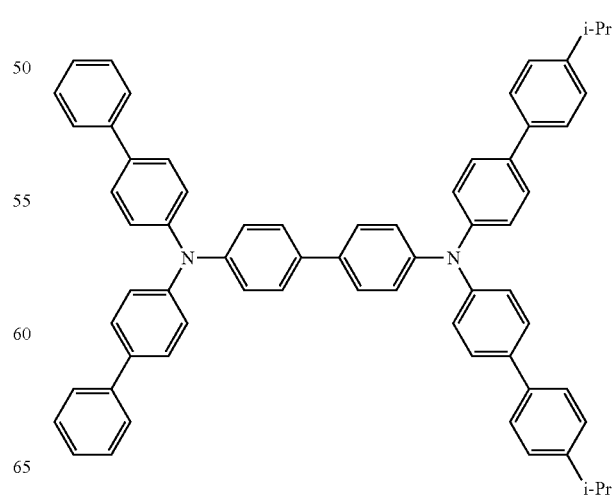

149
-continued
150
-continued
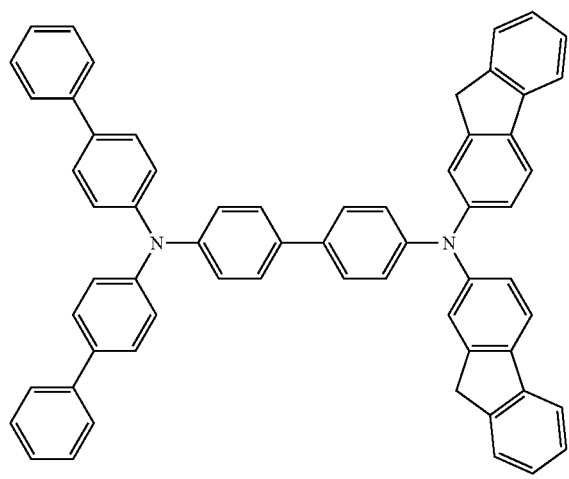
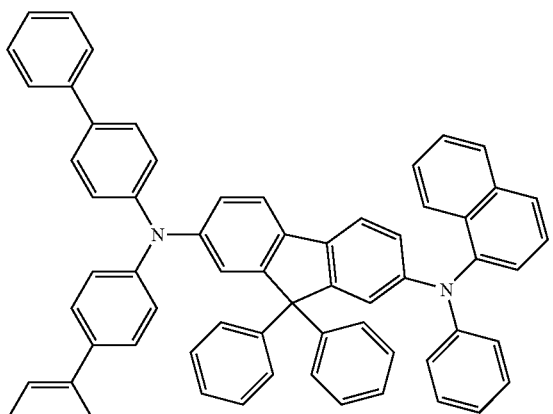
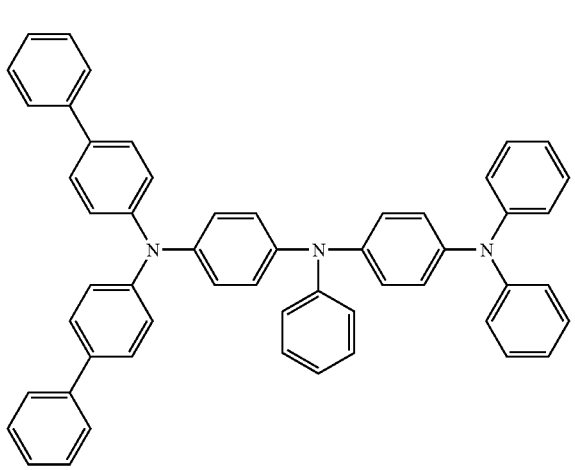
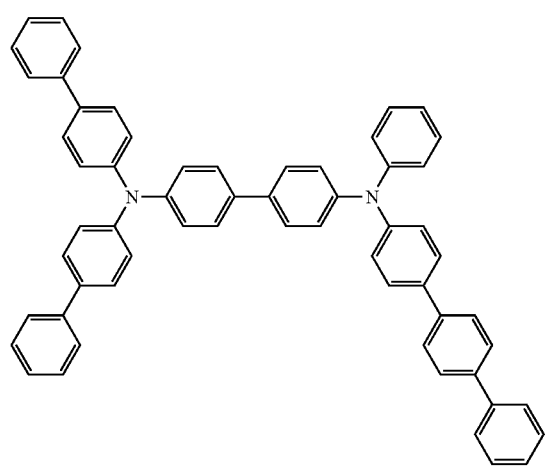
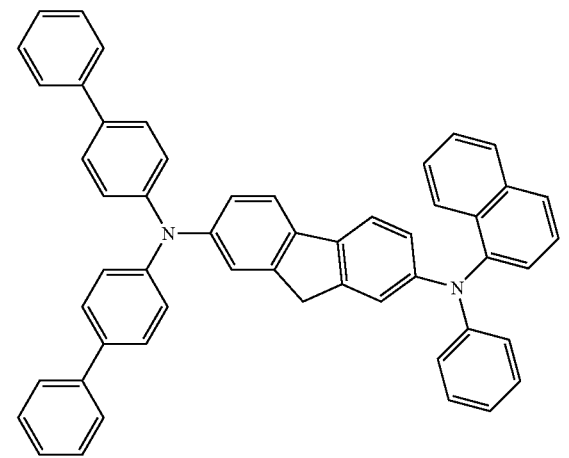
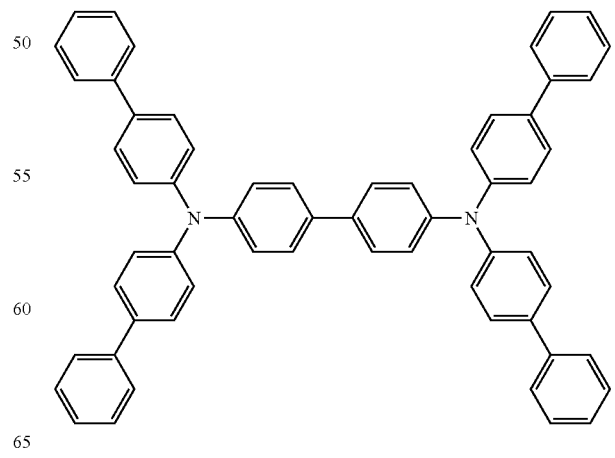

151
-continued
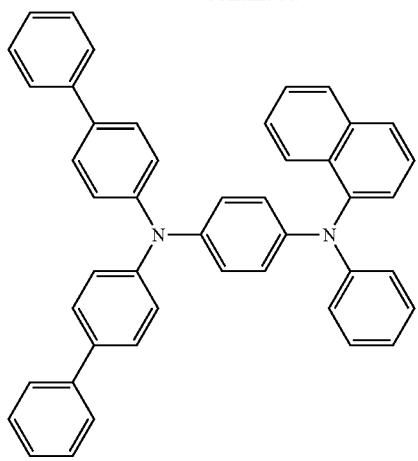
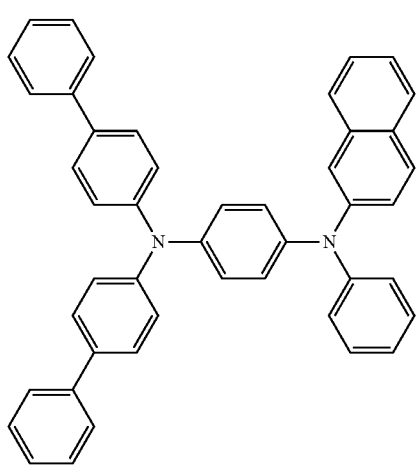
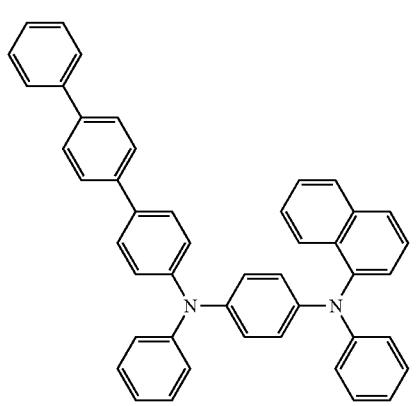
152
-continued
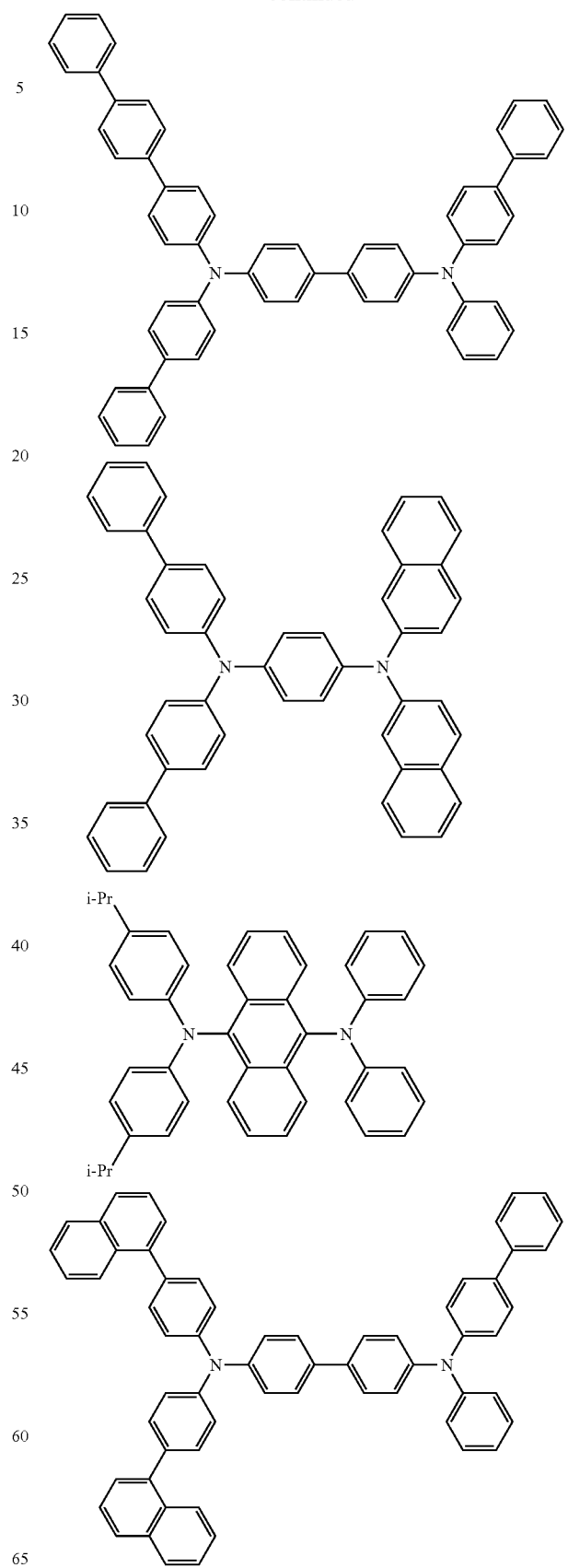

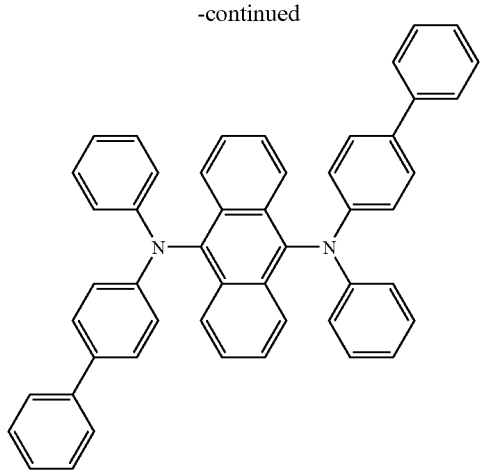
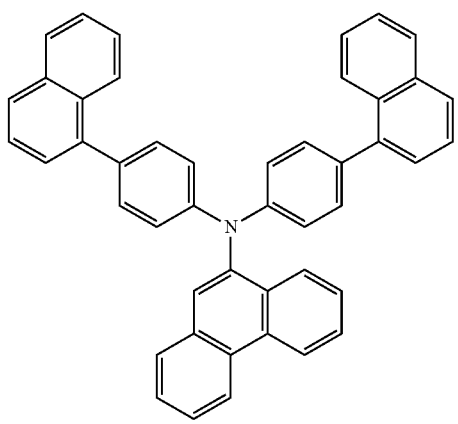

Aromatic amine represented by the following general formula (II) can also be preferably used for forming the hole injecting layer or the hole transporting layer.

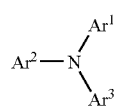
(II)

In the general formula (II), $Ar^1$ to $Ar^3$ each represent the same as those represented by $Ar^1$ to $Ar^4$ of the general formula (I). Examples of the compound represented by the general formula (II) are shown below. However, the compound represented by the formula (II) is not limited thereto.

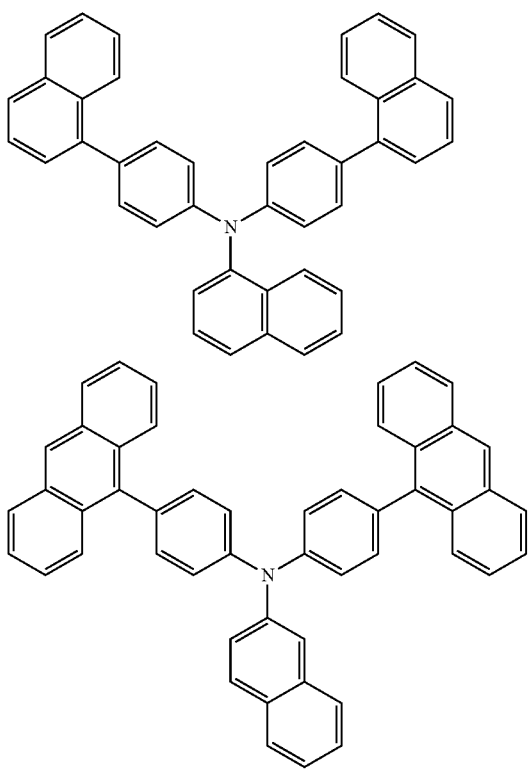
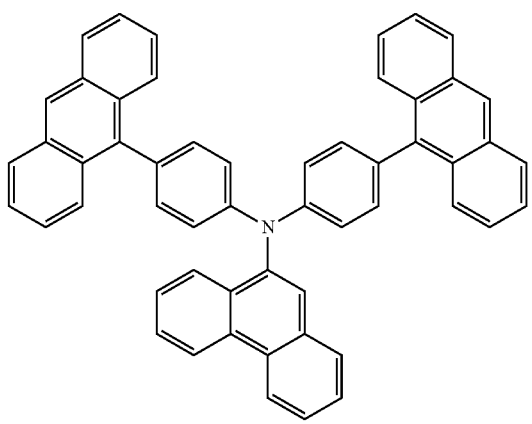
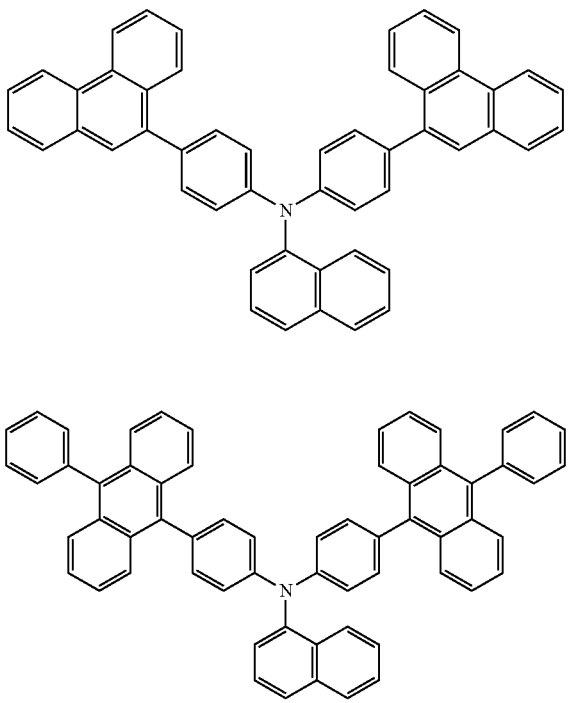

155
-continued
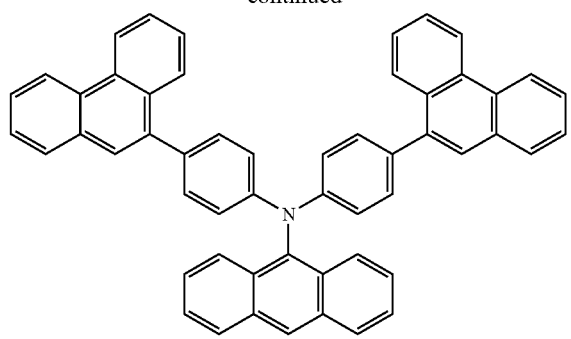
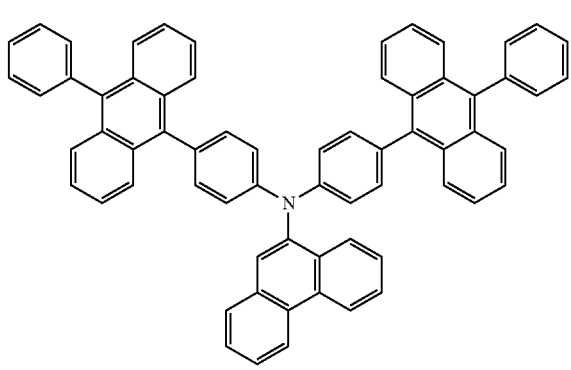
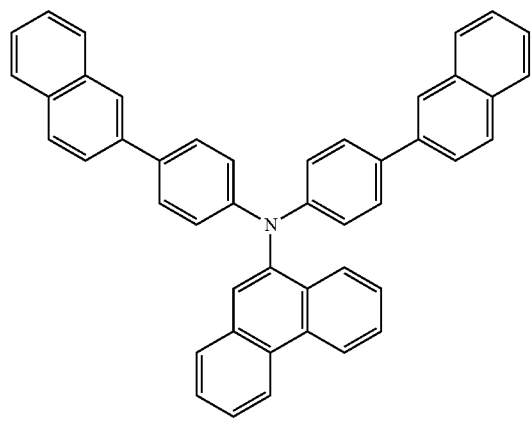
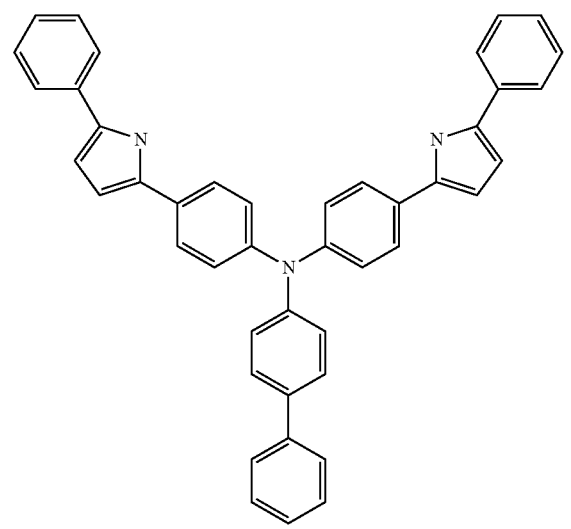
156
-continued
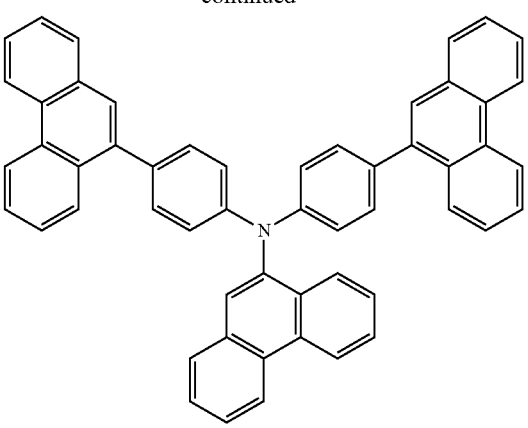
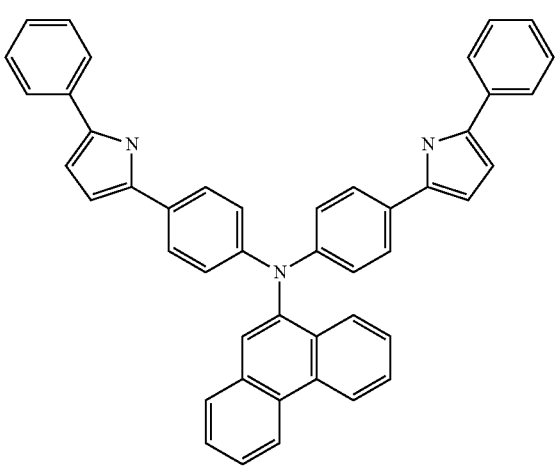
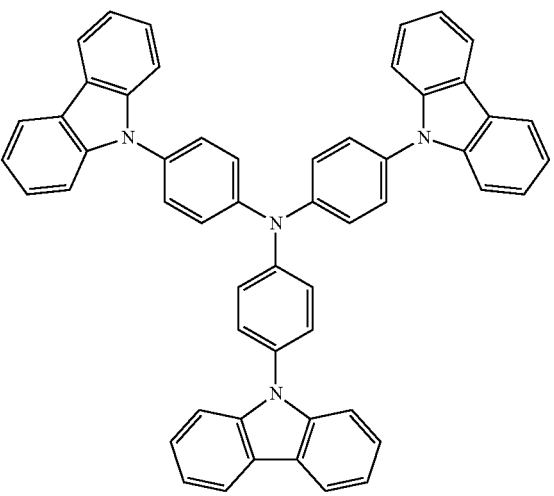

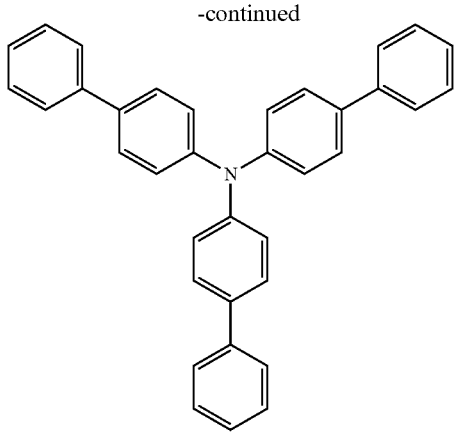

In the present invention, the anode of the organic EL device is used for injecting holes into the hole transporting layer or the emitting layer. It is effective that the anode has a work function of 4.5 eV or more. Exemplary materials for the anode used in the present invention are indium-tin oxide (ITO), tin oxide (NESA), gold, silver, platinum and copper and the like. In order to inject electrons into the electron transporting layer or the emitting layer, materials having a smaller work function is preferable for the cathode. Although a material for the cathode is subject to no specific limitation, examples of the material are indium, aluminum, magnesium, alloy of magnesium and indium, alloy of magnesium and aluminum, alloy of aluminum and lithium, alloy of aluminum, scandium and lithium, alloy of magnesium and silver and the like.

A method of forming each of the layers in the organic EL device according to the present invention are not particularly limited. A conventionally known methods such as vacuum deposition or spin coating may be employed for forming the layers. The organic thin-film layer containing the compound represented by the formula (1), which is used in the organic EL device according to the present invention, may be formed by a conventional coating method such as vacuum deposition, molecular beam epitaxy (MBE method) and coating methods using a solution such as a dipping, spin coating, casting, bar coating, and roll coating.

Although the thickness of each organic layer of the organic EL device is not particularly limited, the thickness is generally preferably in a range of several nanometers to 1 μm because excessively-thinned film likely entails defects such as a pin hole while excessively-thickened film requires high voltage to be applied and deteriorates efficiency.

The organic EL device is formed on a light-transmissive substrate. The light-transmissive plate, which supports the organic EL device, is preferably a smoothly-shaped substrate that transmits 50% or more of light in a visible region of 400 to 700 nm.

The light-transmissive plate is exemplarily a glass plate, a polymer plate or the like.

For the glass plate, such materials as soda-lime glass, barium/strontium-containing glass, lead glass, aluminosilicate glass, borosilicate glass, barium borosilicate glass, quartz and the like can be used.

For the polymer plate, such materials as polycarbonate, acryl, polyethylene terephtalate, polyether sulfide, polysulfone and the like can be used.

Synthesis Example

Next, the present invention will be described in further detail by exemplifying a reference synthesis example and synthesis example(s). However, the present invention is not limited to such synthesis examples.

Reference Synthesis Example

Initially, the reference synthesis example of a compound used for manufacturing a sample of Examples will be described.

(1) Synthesis of Compound 2-1

Synthesis of 2-(3-bromophenyl) naphthalene

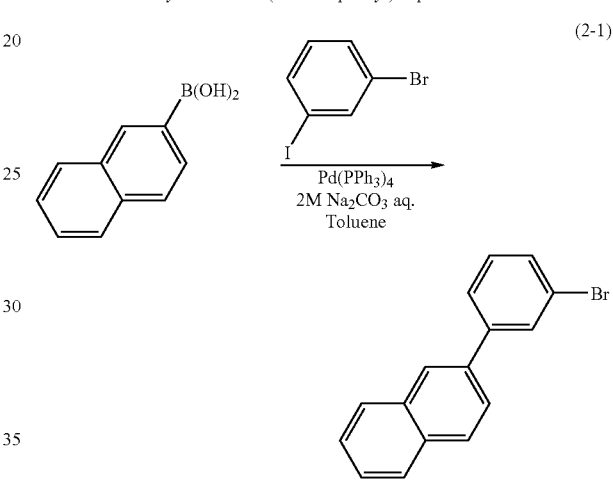

Under an argon gas atmosphere, 243 g (1.41 mol) of 2-naphthalene boronic acid, 400 g (1.41 mol) of 3-bromoiodobenzene, 3.27 g (28.2 mmol) of tetrakis(triphenylphosphine) palladium(0), 6.4 L of toluene and 3.2 L of 2M sodium carbonate solution were mixed together, and stirred for 24 hours while being refluxed. After the reaction in the mixture was over, the mixture experienced filtration, through which aqueous phase thereof was eliminated. After organic phase thereof was cleansed by water and dried with magnesium sulfate, toluene was distilled away under reduced pressure. Residue thereof was refined by silica-gel column chromatography, such that 303 g of 2(3-bromophenyl)naphthalene was obtained with an yield of 76%.

(2) Synthesis of Compound 2-2

Synthesis of 3-(2-naphthyl) phenylboronic acid

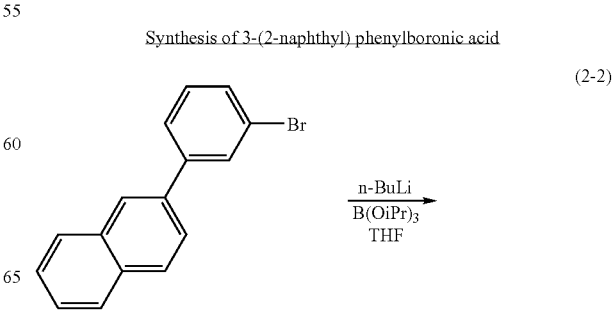

-continued

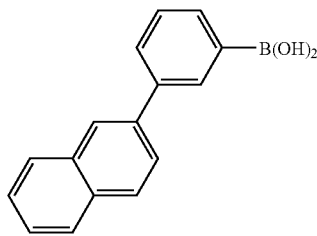

Under an argon gas atmosphere, a mixture of 212 g (748 mmol) of 2(3-bromophenyl) naphthalene and 3 L of dehydrated THF was cooled down to −10 degrees C., and added with 600 ml (948 mmol) of hexane solution of 1.6M n-butyllithium in drops while being stirred. Then, the reaction mixture was stirred for two hours at 0 degree C. The reaction solution was further cooled down to −78 degrees C., and added with 450 g (2.39 mol) of triisopropyl borate in drops. Subsequently, the reaction mixture was stirred for 17 hours at room temperature. The reaction mixture was further added with solution of hydrochloric acid to be stirred for one hour at room temperature. The reaction mixture was further added with 3 L of toluene, so that aqueous phase thereof was eliminated. After organic phase thereof was dried with magnesium sulfate, the solvent was distilled away under reduced pressure. By recrystallizing the obtained solid by toluene, 126 g of 3-(2-naphthyl) phenylboronic acid was obtained at an yield of 67%.

(3) Synthesis of Compound 2-3

Synthesis of 2-(4-bromophenyl) naphthalene

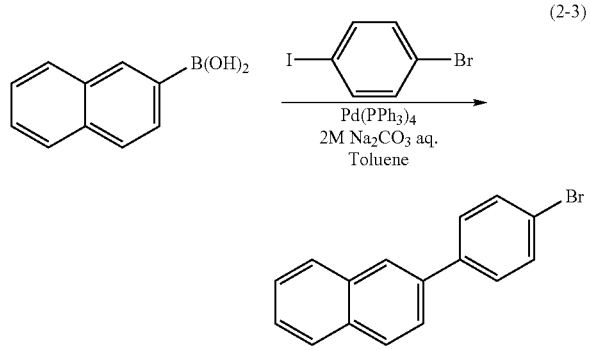

Under an argon gas atmosphere, a mixture of 70.0 g (407 mmol) of 2-naphthalene boronic acid, 115.1 g (407 mmol) of 4-bromoiodobenzene, 9.40 g (8.14 mmol) of tetrakis(triphenylphosphine) palladium(0), 1.2 L of toluene and 600 mL of 2M sodium carbonate solution were mixed, and stirred for 20 hours at 90 degrees C. After the reaction in the mixture was over, toluene was distilled away therefrom, and the mixture was added with methanol, such that precipitated solid was separated by filtration. By recrystallizing the obtained solid by acetic ether and methanol and subsequently drying the solid, 77.2 g of 2-(4-bromophenyl)naphthalene was obtained with an yield of 67%.

(4) Synthesis of Compound 2-4

Synthesis of 4-(2-naphthyl) phenylboronic acid

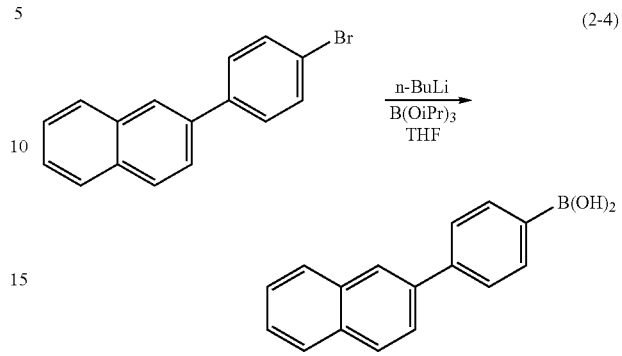

Under an argon gas atmosphere, a mixture of 50.0 g (177 mmol) of 2(4-bromophenyl) naphthalene and 500 mL of dehydrated THF was cooled down to −60 degrees C., and added with 136 mL (212 mmol) of hexane solution of 1.56M n-butyllithium in drops while being stirred. Then, the reaction mixture was stirred for one hour at −60 degrees C. 99.6 g (529 mmol) of triisopropyl borate was dropped into the reaction solution at −60 degrees C. Subsequently, the reaction mixture was warmed up to room temperature, and stirred for 18 hours. The reaction mixture was further added with solution of hydrochloric acid to be stirred for one hour at room temperature. After the reaction, the reaction mixture was further added with toluene, so that aqueous phase thereof was eliminated. After organic phase thereof was dried with magnesium sulfate, the solvent was distilled away under reduced pressure. By crystallizing the obtained solid by toluene, 33.6 g of 4-(2-naphthyl) phenylboronic acid was obtained at an yield of 84%.

(5) Synthesis of Compound 2-5

Synthesis of 1-(3-bromophenyl) naphthalene

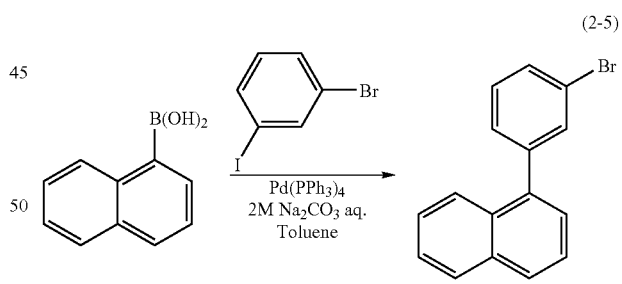

Under an argon gas atmosphere, 200.0 g (1.163 mol) of 1-naphthalene boronic acid, 329.0 g (1.163 mol) of 3-bromoiodobenzene, 26.9 g (23.3 mmol) of tetrakis(triphenylphosphine) palladium(0), 3.7 L of toluene and 1.74 L of 2M sodium carbonate solution were mixed, and stirred for 24 hours while being refluxed. After the reaction in the mixture was over, the mixture experienced filtration, through which aqueous phase thereof was eliminated. After organic phase thereof was cleansed by water and dried with magnesium sulfate, toluene was distilled away under reduced pressure. Residue thereof was refined by silica-gel column chromatography, such that 250 g of 1-(3-bromophenyl)naphthalene was obtained with an yield of 76%.

(6) Synthesis of Compound 2-6

Synthesis of 3-(1-naphthyl) phenylboronic acid (2-6)

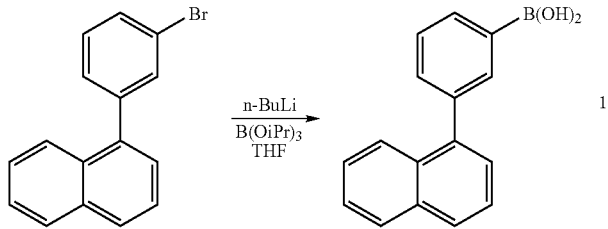

Under an argon gas atmosphere, a mixture of 200.0 g (706.3 mmol) of 1-(3-bromophenyl) naphthalene and 2.1 L of dehydrated THF was cooled down to −60 degrees C., and added with 543 mL (847 mmol) of hexane solution of 1.56M n-butyllithium in drops while being stirred. Then, the reaction mixture was stirred for two hours at −60 degree C. 398.5 g (2.119 mol) of triisopropyl borate was dropped into the reaction solution at −60 degrees C. Subsequently, the reaction mixture was warmed up to room temperature, and stirred for 17 hours. The reaction mixture was further added with solution of hydrochloric acid to be stirred for one hour at room temperature. After the reaction, the reaction mixture was further added with toluene, so that aqueous phase thereof was eliminated. After organic phase thereof was dried with magnesium sulfate, the solvent was distilled away under reduced pressure. By recrystallizing the obtained solid by toluene, 126 g of 3-(1-naphthyl) phenylboronic acid was obtained at an yield of 67%.

(7) Synthesis of Compound 2-7

Synthesis of 1-(4-bromophenyl) naphthalene (2-7)

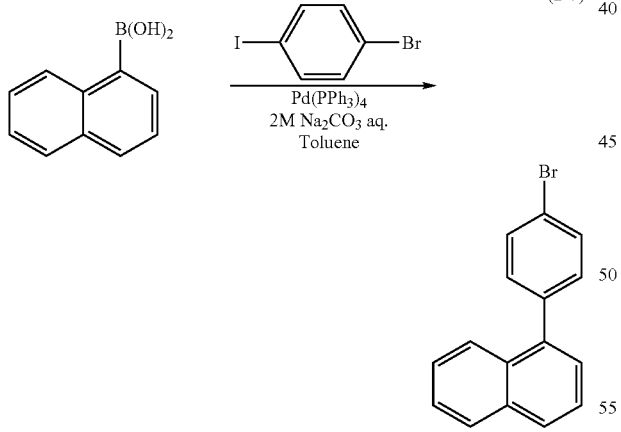

Under an argon gas atmosphere, 200.0 g (1.163 mol) of 1-naphthalene boronic acid, 329.0 g (1.163 mol) of 4-bromoiodobenzene, 26.9 g (23.3 mmol) of tetrakis(triphenylphosphine) palladium(0), 3.7 L of toluene and 1.74 L of 2M sodium carbonate solution were mixed, and stirred for 24 hours at 90 degrees C. After the reaction in the mixture was over, the mixture experienced filtration, through which aqueous phase thereof was eliminated. After organic phase thereof was cleansed by water and dried with magnesium sulfate, toluene was distilled away under reduced pressure. Residue thereof was refined by silica-gel column chromatography, such that 268 g of 1-(4-bromophenyl)naphthalene was obtained with an yield of 81%.

(8) Synthesis of Compound 2-8

Synthesis of 4-(1-naphthyl) phenylboronic acid (2-8)

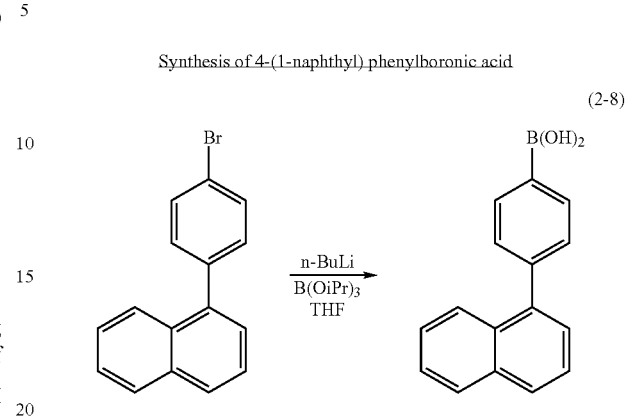

Under an argon gas atmosphere, a mixture of 208.8 g (737.4 mmol) of 1-(4-bromophenyl) naphthalene and 2.1 L of dehydrated THF was cooled down to −60 degrees C., and added with 567 mL (884.9 mmol) of hexane solution of 1.56M n-butyllithium in drops while being stirred. Then, the reaction mixture was stirred for two hours at −60 degree C. 416 g (2.21 mol) of triisopropyl borate was dropped into the reaction solution at −60 degrees C. Subsequently, the reaction mixture was stirred for 17 hours at room temperature. The reaction mixture was further added with solution of hydrochloric acid to be stirred for one hour at room temperature. After the reaction, the reaction mixture was further added with toluene, so that aqueous phase thereof was eliminated. After organic phase thereof was dried with magnesium sulfate, the solvent was distilled away under reduced pressure. By recrystallizing the obtained solid by toluene, 126 g of 4-(1-naphthyl) phenylboronic acid was obtained at an yield of 67%.

(9) Synthesis of Compound 2-9

Synthesis of 1-bromo-4-phenylnaphthalene (2-9)

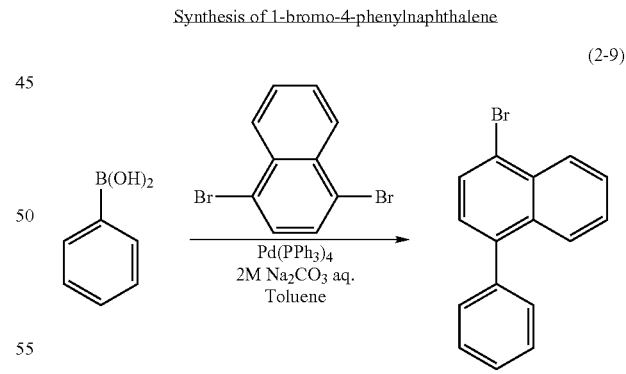

Under an argon gas atmosphere, 128.0 g (1.049 mol) of phenylboronic acid, 300.0 g (1.163 mol) of 1,4-dibromonaphthalene, 24.2 g (21.0 mmol) of tetrakis(triphenylphosphine) palladium(0), 4.3 L of dimethoxyethane and 1.60 L of 2M sodium carbonate solution were mixed, and stirred for 24 hours at 78 degrees C. The reaction mixture was further added with toluene and water, and then aqueous phase thereof was eliminated. After organic phase thereof was cleansed by water and dried with magnesium sulfate, toluene was distilled away under reduced pressure. By refining residue thereof by silica-gel column chromatography and by recrystallizing the residue by hexane, 122 g of 1-bromo-4-phenyl naphthalene was obtained with an yield of 41%.

(10) Synthesis of Compound 2-10

Synthesis of 1-(4-phenylnaphthalene)-boronic acid

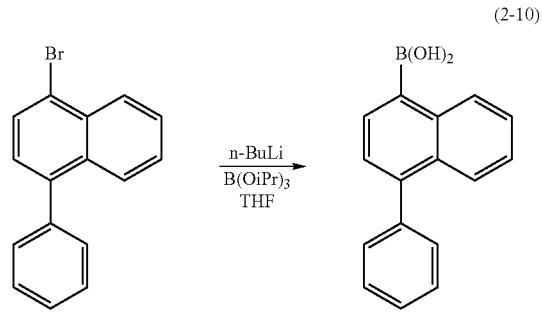

(2-10)

Under an argon gas atmosphere, a mixture of 121.0 g (427.3 mmol) of 1-bromo-4-phenylnaphthalene, 1.2 L of dehydrated THF and 1.2 L of dehydrated diethylether was cooled down to −20 degrees C., and added with 360 mL (562 mmol) of hexane solution of 1.56M n-butyllithium in drops while being stirred. Then, the reaction mixture was stirred for one hour at −20 degree C. The reaction mixture was further cooled down to −60 degrees C., and added with 241.1 g (1.28 mol) of triisopropyl borate in drops. The reaction mixture was subsequently warmed up to room temperature, and stirred for 16 hours at room temperature. The reaction mixture was further added with solution of hydrochloric acid to be stirred for one hour at room temperature. After the reaction, the reaction mixture was further added with toluene, so that aqueous phase thereof was eliminated. After organic phase thereof was cleansed with water and dried with magnesium sulfate, the solvent was distilled away under reduced pressure. By recrystallizing the obtained solid by hexane, 61.0 g of 1-(4-phenylnaphthalene)-boronic acid was obtained at an yield of 58%.

(11) Synthesis of Compound 2-11

Synthesis of 2-bromo-6-phenylnaphthalene

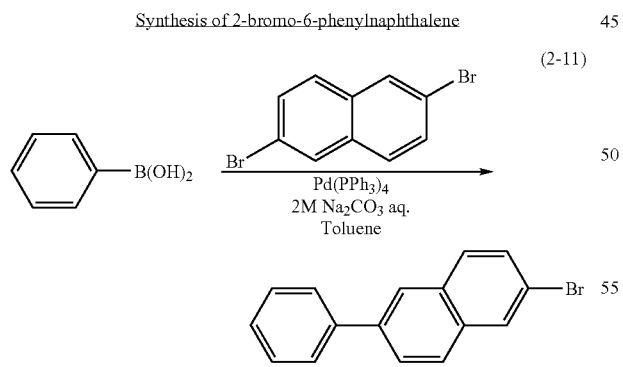

(2-11)

Under an argon gas atmosphere, 128.0 g (1.049 mol) of phenylboronic acid, 300.0 g (1.163 mol) of 2,6-dibromonaphthalene, 24.2 g (21.0 mmol) of tetrakis(triphenylphosphine) palladium(0), 4.3 L of dimethoxyethane and 1.60 L of 2M sodium carbonate solution were mixed, and stirred for 24 hours at 78 degrees C. The reaction mixture was further added with toluene and water, and then aqueous phase thereof was eliminated. After organic phase thereof was cleansed by water and dried with magnesium sulfate, toluene was distilled away under reduced pressure. By refining residue thereof by silica-gel column chromatography and by recrystallizing the residue by hexane, 108 g of 2-bromo-6-phenyl naphthalene was obtained with an yield of 36%.

(12) Synthesis of Compound 2-12

Synthesis of 2-(6-phenynaphthalene)-boronic acid

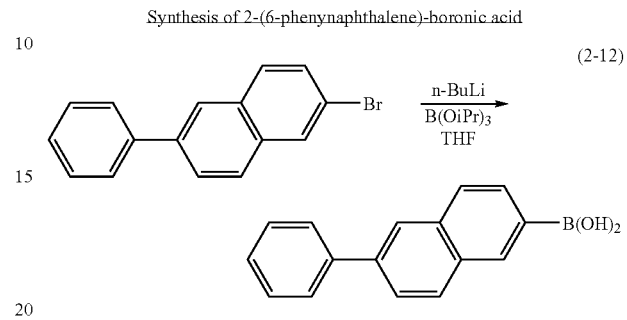

(2-12)

Under an argon gas atmosphere, a mixture of 100.0 g (353.1 mmol) of 2-bromo-6-phenylnaphthalene, 1.2 L of dehydrated THF and 1.2 L of dehydrated diethylether was cooled down to −20 degrees C., and added with 280 mL (437 mmol) of hexane solution of 1.56M n-butyllithium in drops while being stirred. Then, the reaction mixture was stirred for one hour at −20 degree C. The reaction mixture was further cooled down to −60 degrees C., and added with 199.3 g (1.06 mol) of triisopropyl borate in drops. The reaction mixture was subsequently warmed up to room temperature, and stirred for 16 hours at room temperature. The reaction mixture was further added with solution of hydrochloric acid to be stirred for one hour at room temperature. After the reaction, the reaction mixture was further added with toluene, so that aqueous phase thereof was eliminated. After organic phase thereof was cleansed with water and dried with magnesium sulfate, the solvent was distilled away under reduced pressure. By recrystallizing the obtained solid by hexane, 58.0 g of 2-(6-phenylnaphthalene)-boronic acid was obtained at an yield of 55%.

(13) Synthesis of Compound 2-13

Synthesis of 2,6-dibromo-1,5-bis(trifluoromethylsulfonyloxy)-naphthalene

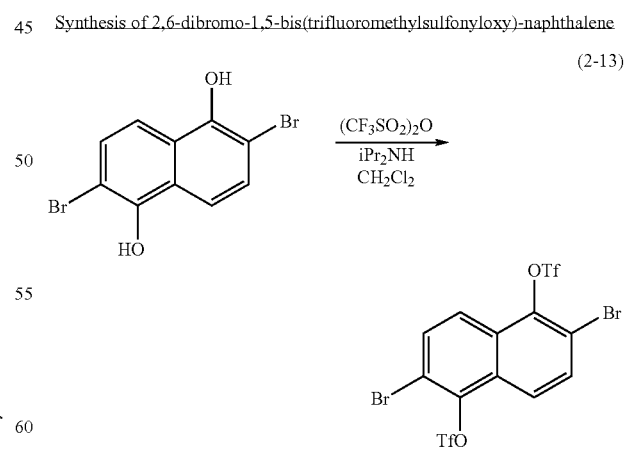

(2-13)

Under an argon gas atmosphere, a mixture of 25.00 g (78.6 mmol) of 2,6-dibromo-1,5-naphthalenediol, 30.48 g (235.9 mmol) of diisopropylamine and 250 mL of dehydrated dichloromethane was cooled down to 0 degree C., and 65.55 g (235.9 mmol) of trifluoromethanesulfonic anhydride was dropped into the mixture while the mixture was stirred. The mixture was warmed up to room temperature, and stirred for 18 hours. The reaction mixture was further added with water, and organic phase thereof was cleansed with water and dried with magnesium sulfate. After the solvent was distilled away, residue was refined by column chromatography, so that 36.0 g of 2,6-dibromo-1,5-bis(trifluoromethylsulfonyloxy)-naphthalene was obtained at an yield of 79%.

(14) Synthesis of Compound 2-14

Synthesis of 2,6-bromo-1,5-diphenylnapthalene

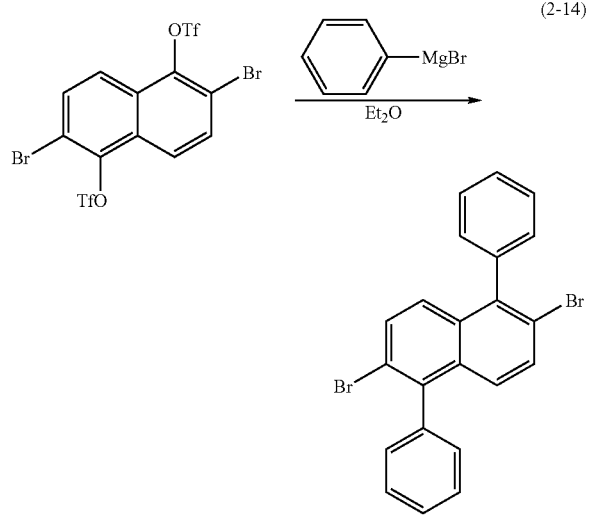

(2-14)

Under an argon gas atmosphere, a mixture of 36.0 g (61.8 mmol) of 5-{[(trifluoromethyl) sulfonyl]oxy}naphthyl trifluoromethanesulfonate, 3.60 g (6.18 mmol) of $PdCl_2(dppp)$, 10.8 g (123.7 mmol) of lithium bromide and 300 mL of diethylether was cooled down to 0 degree C. Then, the mixture was added with 68.0mL (136.0 mmol) of THF solution of 2.0M-phenylmagnesium bromide in drops and stirred for 18 hours at room temperature. The reaction mixture was further added with solution of 2M-hydrochloric acid to be extracted by toluene. After organic phase thereof was cleansed by water and dried with magnesium sulfate, the solvent was distilled away under reduced pressure. Residue thereof was refined by silica-gel column chromatography, such that 18.0 g of 2,6-dibromo-1,5-diphenylnaphthalene was obtained with an yield of 66%.

Synthesis Example

Next, the synthesis examples of compounds used in Examples, each of which is synthesized using the bromo compound and the boronic acid compound obtained according to the reference synthesis example(s), will be described.

(17) Synthesis of Compound 1-1

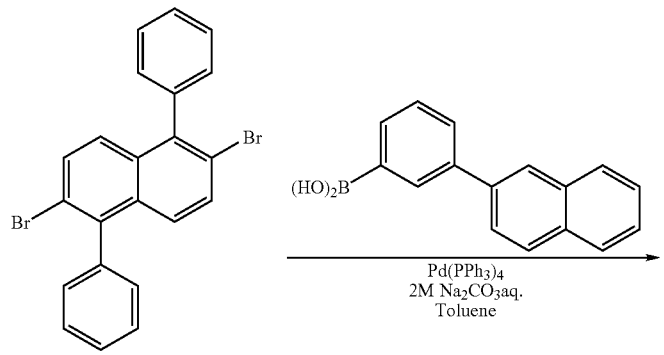

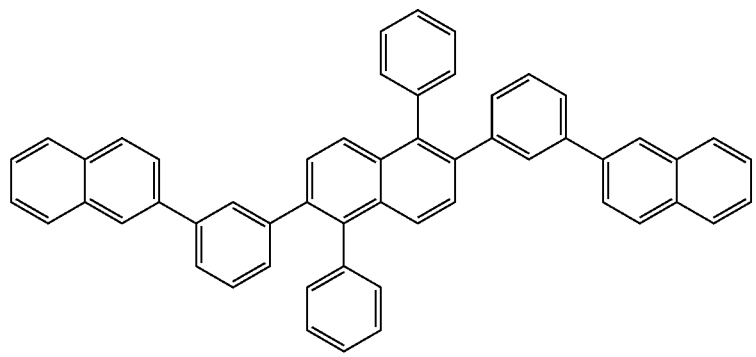

1-1

Under an argon gas atmosphere, 7.00 g (16.0 mmol) of 2,6-dibromo-1,5-diphenylnaphthalene, 8.32 g (33.6 mmol) of 3-(2-naphthyl) phenylboronic acid, 0.74 g (0.64 mmol) of tetrakis(triphenylphosphine) palladium(0), 200 mL of toluene, 50 mL of dimethoxyethane and 48 mL of 2M sodium carbonate solution were mixed, and stirred for 10 hours at 90 degrees C. Subsequently, the reaction mixture was cooled down to room temperature, added with water and stirred for one hour. After the solid precipitated during the reaction was separated by filtration, the obtained solid was cleansed with water, methanol, dimethoxyethane and toluene in this order. By dissolving the obtained solid in toluene and refining the solution by silica-gel column chromatography, 2.20 g of the compound 1-1 was obtained at an yield of 49%.

Mass-spectrum analysis consequently showed that m/e was equal to 684 while a calculated molecular weight was 684.28.

(18) Synthesis of Compound 1-2

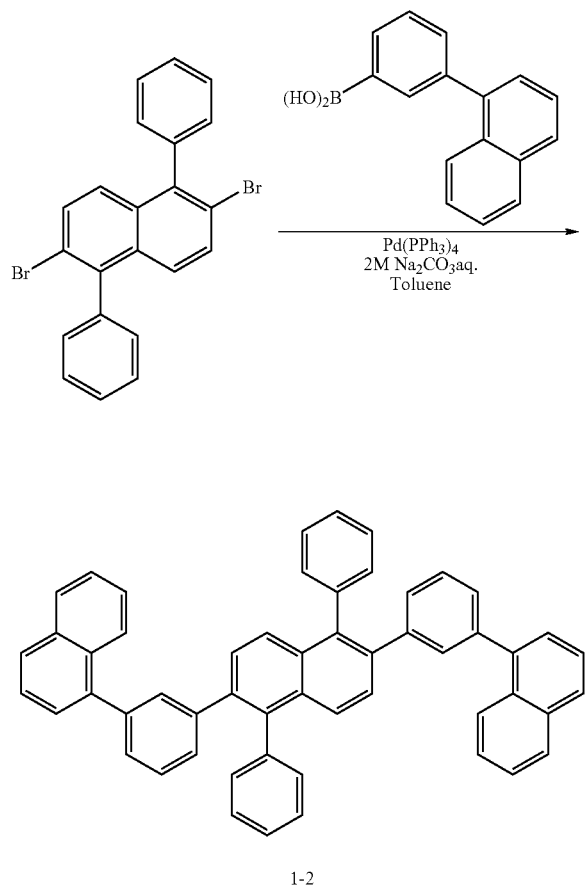

1-2

The compound 1-2 was synthesized by the same method as the compound 1-1 except that 3-(1-naphthyl) phenylboronic acid was used in place of 3-(2-naphthyl) phenylboronic acid.

Mass-spectrum analysis consequently showed that m/e was equal to 684 while a calculated molecular weight was 684.28.

(19) Synthesis of Compound 1-3

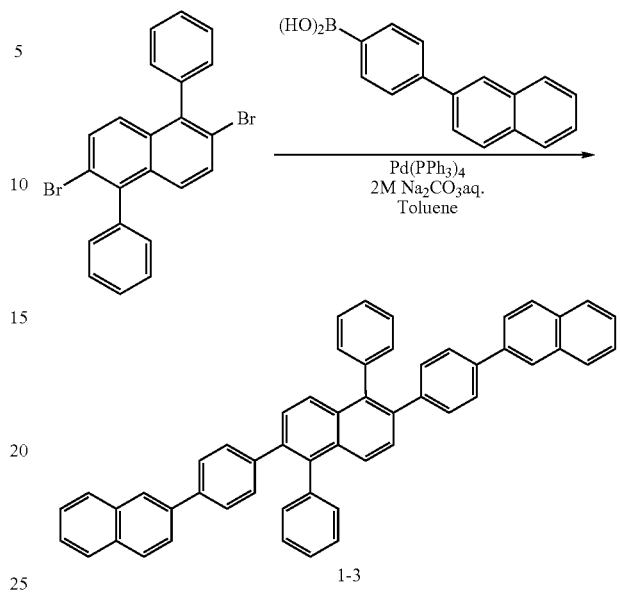

1-3

The compound 1-3 was synthesized by the same method as the compound 1-1 except that 4-(2-naphthyl) phenylboronic acid was used in place of 3-(2-naphthyl) phenylboronic acid.

Mass-spectrum analysis consequently showed that m/e was equal to 684 while a calculated molecular weight was 684.28.

(20) Synthesis of Compound 1-4

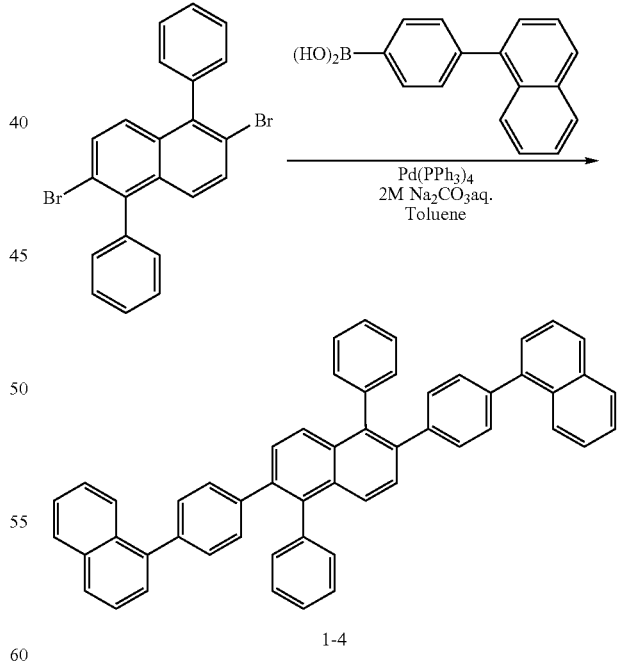

1-4

The compound 1-4 was synthesized by the same method as the compound 1-1 except that 4-(1-naphthyl) phenylboronic acid was used in place of 3-(2-naphthyl) phenylboronic acid.

Mass-spectrum analysis consequently showed that m/e was equal to 684 while a calculated molecular weight was 684.28.

(21) Synthesis of Compound 1-6
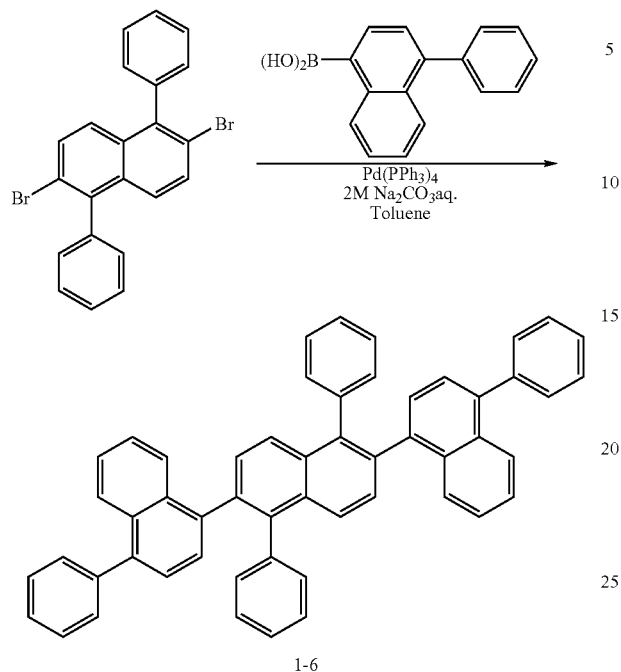
The compound 1-6 was synthesized by the same method as the compound 1-1 except that 1-(4-phenyl)-naphthaleneboronic acid was used in place of 3-(2-naphthyl)phenylboronic acid.
Mass-spectrum analysis consequently showed that m/e was equal to 684 while a calculated molecular weight was 684.28.
(22) Synthesis of Compound 1-8
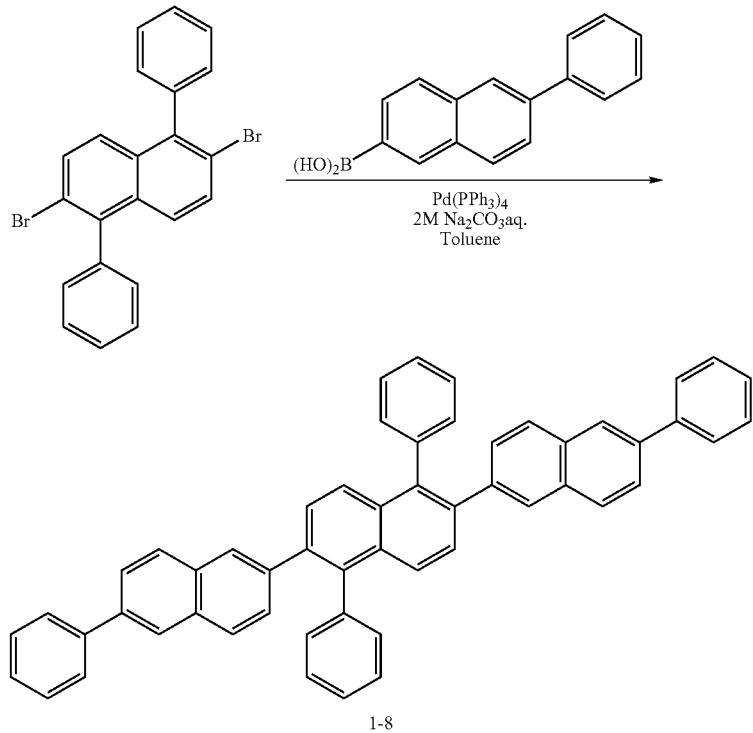

The compound 1-8 was synthesized by the same method as the compound 1-1 except that 2-(6-phenyl)-naphthalene-boronic acid was used in place of 3-(2-naphthyl) phenylboronic acid.

Mass-spectrum analysis consequently showed that m/e was equal to 684 while a calculated molecular weight was 684.28.

(22) Synthesis of Compound 1-26

2-bromo-7-(3-naphthalene-2-yl)phenyl)-1,5-diphenylnaphthalene was obtained at an yield of 34%.

Subsequently, under an argon gas atmosphere, 4.30 g (76.6 mmol) of 2-bromo-7-(3-naphthalene-2-yl)phenyl)-1,5-diphenylnaphthalene, 1.38 g (8.04 mmol) of 2-naphthaleneboronic acid, 0.18 g (0.15 mmol) of tetrakis(triphenylphosphine) palladium(0), 100 mL of toluene, 20 mL of

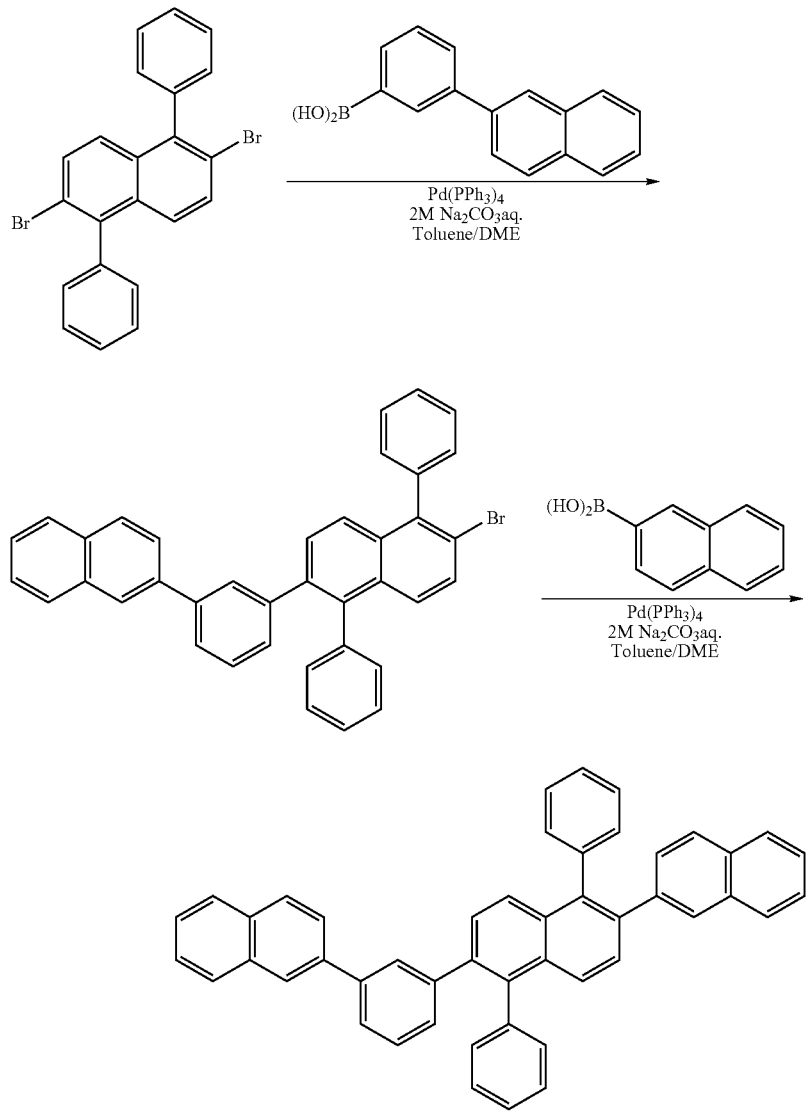

1-26

Under an argon gas atmosphere, 10.00 g (22.8 mmol) of 2,6-dibromo-1,5-diphenylnaphthalene, 5.66 g (22.8 mmol) of 3-(2-naphthyl) phenylboronic acid, 0.53 g (0.46 mmol) of tetrakis(triphenylphosphine) palladium(0), 200 mL of toluene, 50 mL of dimethoxyethane and 34 mL of 2M sodium carbonate solution were mixed, and stirred for 10 hours at 90 degrees C. Subsequently, the reaction mixture was cooled down to room temperature, added with water and stirred for one hour. After the solid precipitated during the reaction was separated by filtration, the obtained solid was cleansed with water, methanol, dimethoxyethane and toluene in this order. By dissolving the obtained solid in toluene and refining the solution by silica-gel column chromatography, 4.30 g of dimethoxyethane and 12 mL of 2M sodium carbonate solution were mixed, and stirred for 10 hours at 90 degrees C. Subsequently, the reaction mixture was cooled down to room temperature, added with water and stirred for one hour. After the solid precipitated during the reaction was separated by filtration, the obtained solid was cleansed with water, methanol, dimethoxyethane and toluene in this order. By dissolving the obtained solid in toluene and refining the solution by silica-gel column chromatography, 1.20 g of the compound 1-26 was obtained at an yield of 55%.

Mass-spectrum analysis consequently showed that m/e was equal to 608 while a calculated molecular weight was 608.25.

(23) Synthesis of Compound 1-27
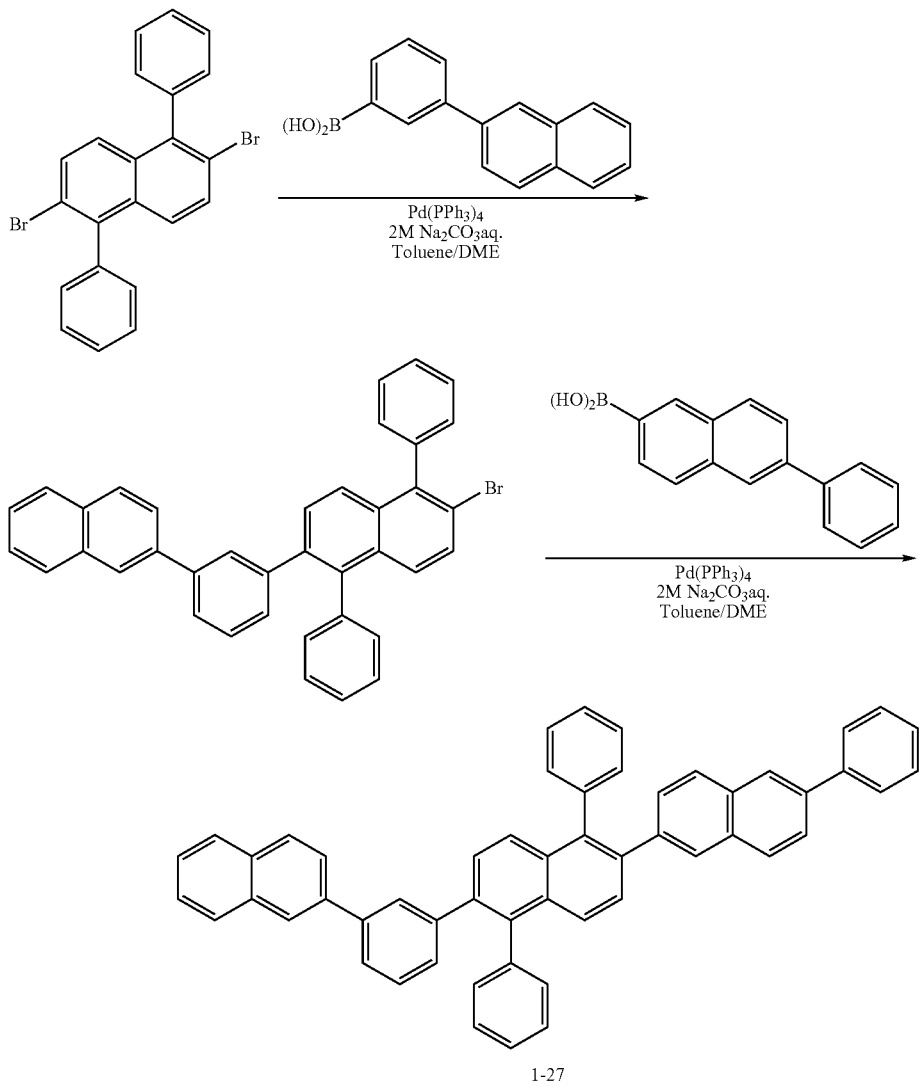
The compound 1-27 was synthesized by the same method as the compound 1-26 except that 6-phenyl-2 naphthaleneboronic acid was used in place of 2-naphthaleneboronic acid. Mass-spectrum analysis consequently showed that m/e was equal to 684 while a calculated molecular weight was 684.285.
(24) Synthesis of Compound 1-29
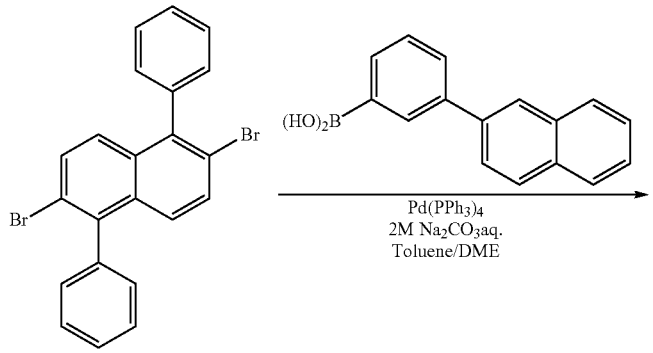

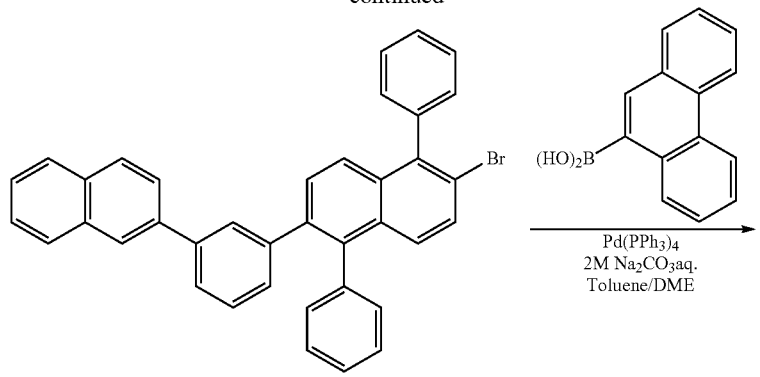
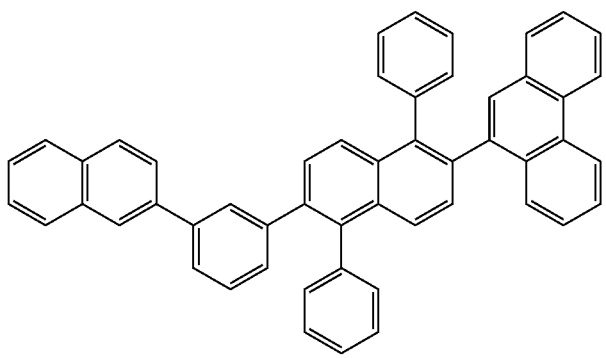
1-29
The compound 1-29 was synthesized by the same method as the compound 1-26 except that 9-phenanthreneboronic acid was used in place of 2-naphthaleneboronic acid.
Mass-spectrum analysis consequently showed that m/e was equal to 658 while a calculated molecular weight was 658.27.
(25) Synthesis of Compound 1-31
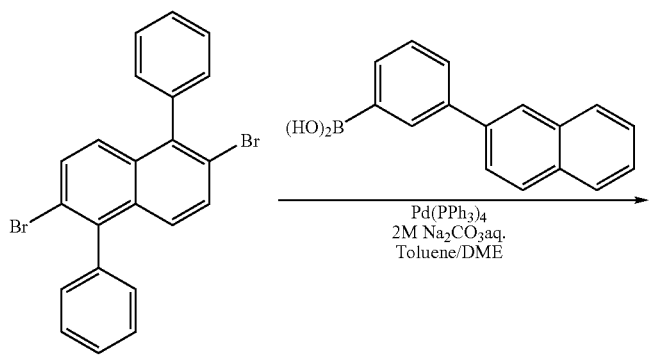

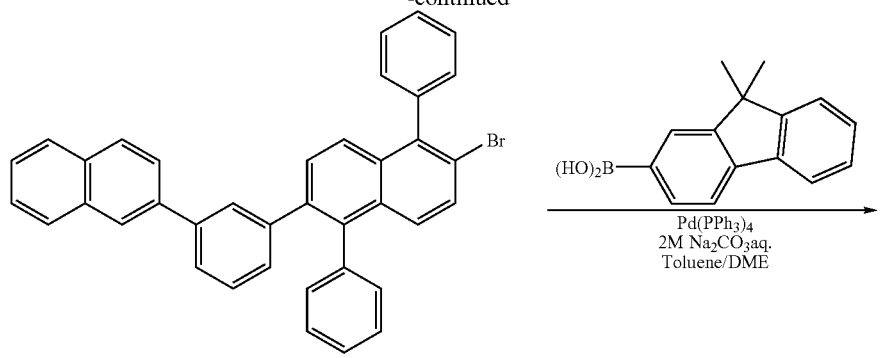

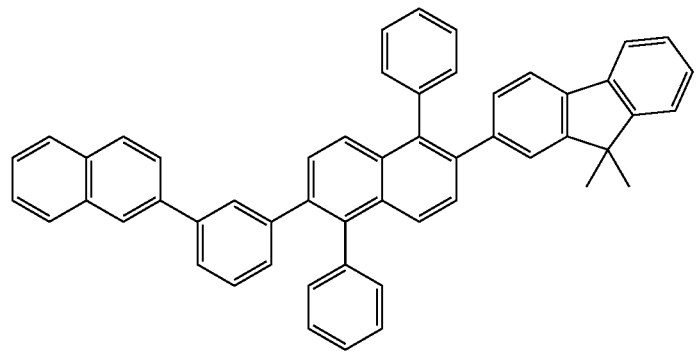

1-31

The compound 1-31 was synthesized by the same method as the compound 1-26 except that 4-(2-naphthyl) phenylboronic acid was used in place of 3-(2-naphthyl) phenylboronic acid and that 9,9-dimethyl-9H-florene-2-yl-boronic acid was used in place of 2-naphthaleneboronic acid.

Mass-spectrum analysis consequently showed that m/e was equal to 674 while a calculated molecular weight was 674.30.

(26) Synthesis of Compound 1-51

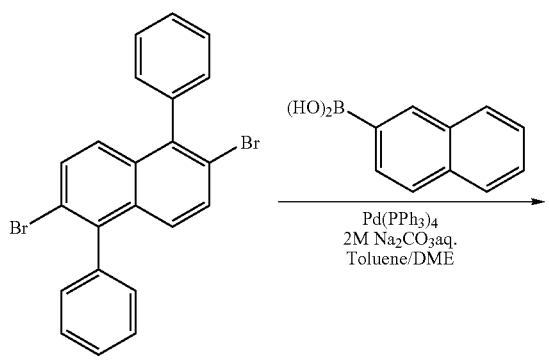

-continued

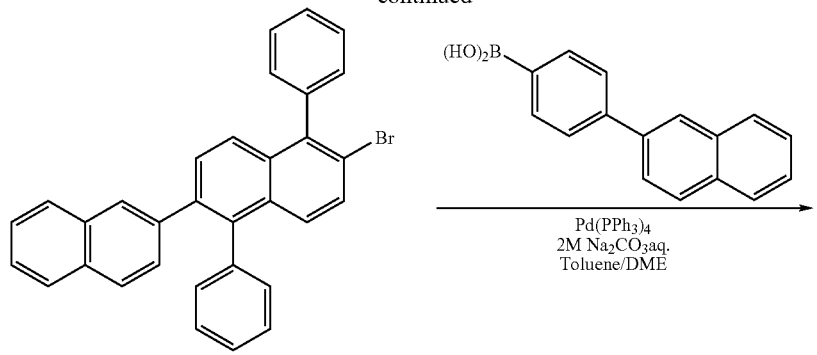

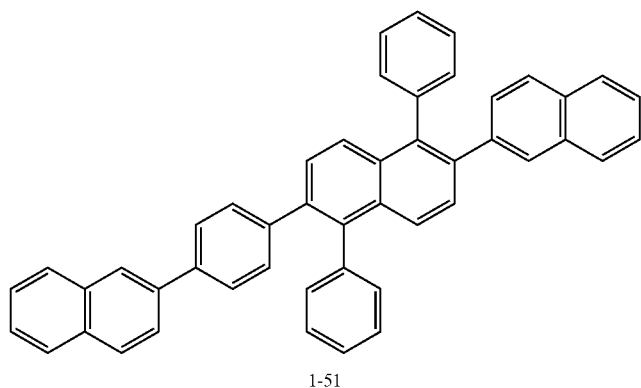

1-51

The compound 1-51 was synthesized by the same method as the compound 1-26 except that 2-naphthaleneboronic acid was used in place of 3-(2-naphthyl) phenylboronic acid and that 4-(2-naphthyl)phenylboronic acid was used in place of 2-naphthaleneboronic acid.

Mass-spectrum analysis consequently showed that m/e was equal to 608 while a calculated molecular weight was 608.25.

(27) Synthesis of Compound 1-52

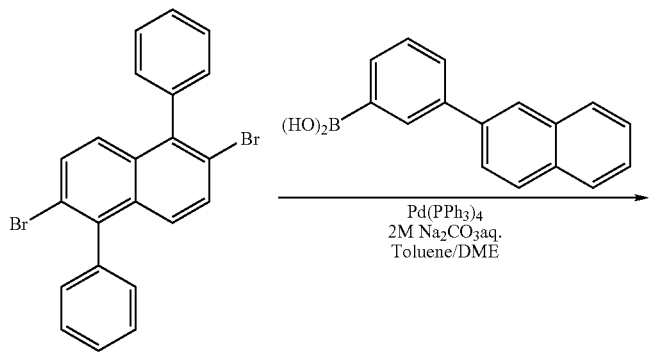

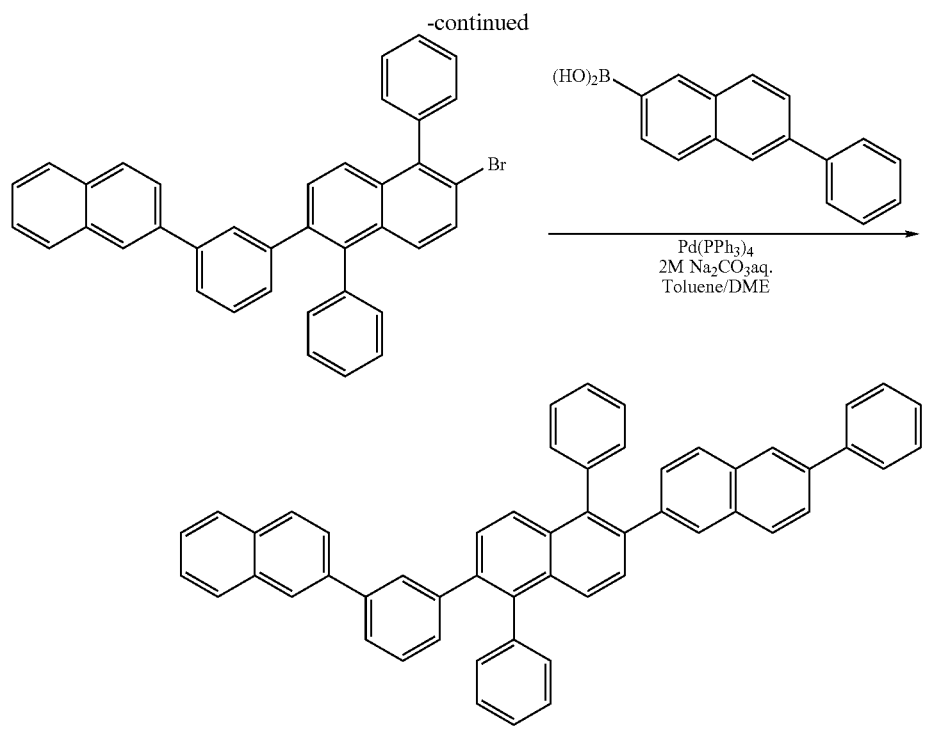
The compound 1-52 was synthesized by the same method as the compound 1-26 except that 6-phenyl-2 naphthaleneboronic acid was used in place of 2-naphthaleneboronic acid. Mass-spectrum analysis consequently showed that m/e was equal to 684 while a calculated molecular weight was 684.28.
(28) Synthesis of Compound 1-53
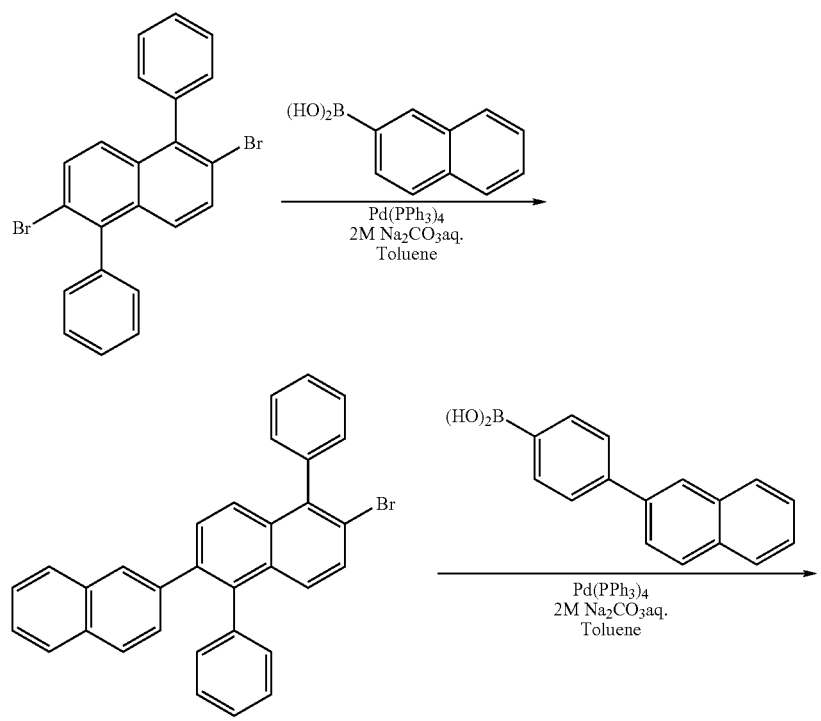

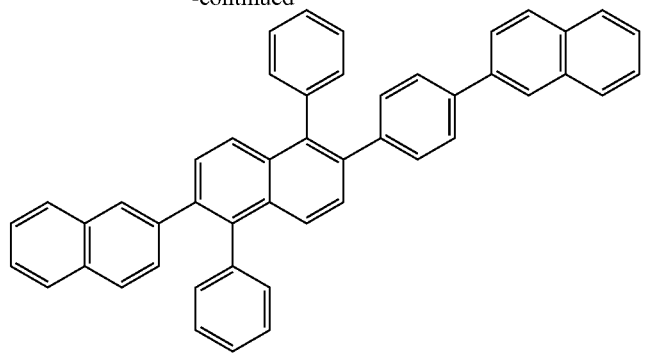

1-53

The compound 1-53 was synthesized by the same method as the compound 1-26 except that 2-naphthaleneboronic acid was used in place of 3-(2-naphthyl) phenylboronic acid and that 6-phenyl-2-naphthaleneboronic acid was used in place of 2-naphthaleneboronic acid.
Mass-spectrum analysis consequently showed that m/e was equal to 608 while a calculated molecular weight was 608.25.

In the above synthesis examples, the mass-spectrum analysis was conducted by FD-MS (field desorption mass spectrometry). A machine used in the measurement of FD-MS (field desorption mass spectrometry) and measurement conditions thereof will be described below.

Machine: JSM-700 (manufactured by Japan Electron Optics Laboratories Ltd.)
Conditions: accelerating voltage of 8 kV
Scan range m/z of 50 to 3000
Emitter type: carbon
emitter current: 0 mA→2 mA/minute→40 mA (maintained for 10 minutes)

EXAMPLES

Next, the present invention will be described in further detail by exemplifying Example(s). However, the present invention is not limited to Example(s).

In addition to the compounds obtained by the above synthesis examples, structures of compounds used in Examples and Comparatives will be shown below.

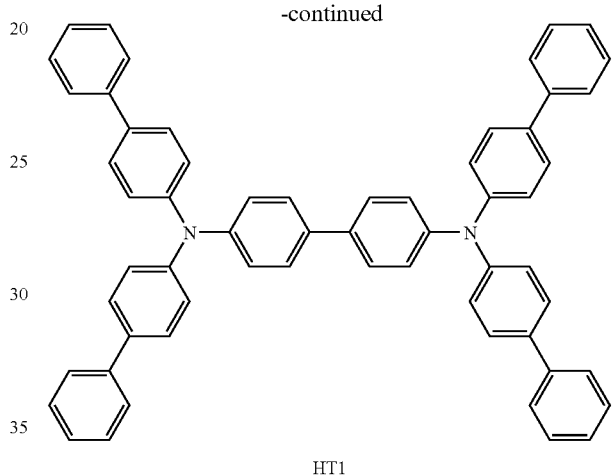

HT1

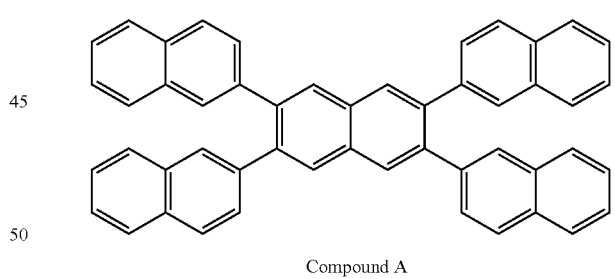

Compound A

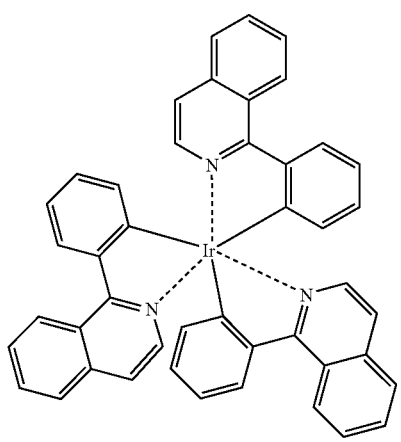

Ir(piq)₃

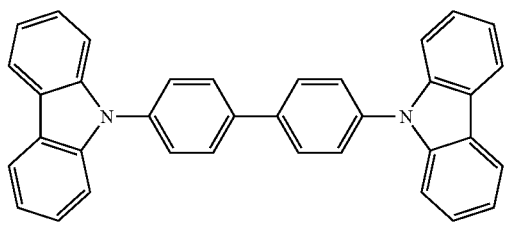

CBP

-continued

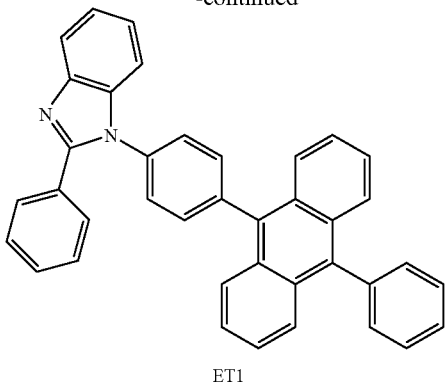

ET1

Example 1

Manufacturing of Organic EL Device

A glass substrate (size: 25 mm×75 mm×0.7 mm thick) having an ITO transparent electrode (manufactured by Asahi Glass Co., Ltd) was ultrasonic-cleaned in isopropyl alcohol for five minutes, and then UV/ozone-cleaned for 30 minutes. After the glass substrate having the transparent electrode line was cleaned, the glass substrate was mounted on a vacuum deposition apparatus, so that 50-nm thick film of HT1 was initially formed to cover a surface of the glass substrate where the transparent electrode line was provided. The HT1 film serves as a hole injecting/transporting layer. Subsequently to the formation of the hole injecting/transporting layer, 40-nm thick film of a new host compound 1-1 and a film of Ir(piq)$_3$ as a phosphorescent dopant were co-evaporated by resistance heating so that Ir(piq)$_3$ was contained therein with a content of 10 mass %. The co-deposited film serves as an emitting layer (phosphorescent emitting layer). After the film of the emitting layer was formed, 40-nm thick film of ET1 was formed. The film of ET1 serves as an electron transporting layer. Then, 0.5-nm thick film of LiF was formed as an electron-injecting electrode (cathode) at a film-forming speed of 1 Å/min. Metal (Al) was vapor-deposited on the LiF film to form a 150-nm thick metal cathode, thereby providing the organic EL device.

Examples 2 to 13 and Comparatives 1 and 2

The organic EL devices according respectively to Examples 2 to 13 and Comparatives 1 and 2 are formed by the same method as Example 1 except that host compounds shown in Table 1 were respectively used in place of the new host compound 1-1.

[Evaluation on Emitting Performance of Organic EL Device]

The organic EL devices according to Examples 1 to 13 and Comparatives 1 and 2 each were driven by direct-current electricity to emit light, so that voltage at a current density of 10 mA/cm$^2$, luminous efficiency and time elapsed until the initial luminance intensity of 5000 cd/m$^2$ was reduced to the half (i.e., time until half-life) were measured for each organic EL device. Then, pixel uniformity when each organic EL device was driven at 70 degrees C. was visually checked, among which devices having uniform pixels are rated as A while devices having ununiform pixels are rated as B. The results of the evaluation are shown in Table 1.

TABLE 1

| Examples | Host Compound | Voltage (V) | Luminous Efficiency (cd/A) | Time until Half-Life (hours) | Pixel Uniformity When Driven at 70° C. |
|---|---|---|---|---|---|
| Example 1 | 1-1 | 4.2 | 9.3 | 5200 | A |
| Example 2 | 1-2 | 4.3 | 8.7 | 4800 | A |
| Example 3 | 1-3 | 4.1 | 8.9 | 5500 | A |
| Example 4 | 1-4 | 4.4 | 8.6 | 4500 | A |
| Example 5 | 1-6 | 4.2 | 8.3 | 4500 | A |
| Example 6 | 1-8 | 4.2 | 8.4 | 5400 | A |
| Example 7 | 1-26 | 4.5 | 9.2 | 4800 | A |
| Example 8 | 1-27 | 4.1 | 9.1 | 4600 | A |
| Example 9 | 1-29 | 4.1 | 8.6 | 5000 | A |
| Example 10 | 1-31 | 4.3 | 9.2 | 5200 | A |
| Example 11 | 1-51 | 4.5 | 8.3 | 5500 | A |
| Example 12 | 1-52 | 4.4 | 9.4 | 5200 | A |
| Example 13 | 1-53 | 4.1 | 9.2 | 5300 | A |
| Comparative 1 | CBP | 5.4 | 6.3 | 500 | B |
| Comparative 2 | Compound A | 5.0 | 8.9 | 4000 | B |

As is understood from the above, the organic EL device according to each of Examples 1 to 13, in which the naphthalene derivative according to the present invention was used as the host of the phosphorescent emitting layer, is excellent in time until half-life, pixel uniformity when driven at a high temperature of 70 degrees C. and luminous efficiency, and requires less drive voltage, as compared with the organic EL device according to each of Comparatives 1 and 2.

Accordingly, the organic EL device according to the present invention is free from pixel defects and excellent in luminous efficiency, heat resistance and lifetime.

The priority application Numbers JP2007-179120 and JP2007-179121 upon which this patent application is based are hereby incorporated by reference.

What is claimed is:

1. A naphthalene derivative represented by the following formula (1),

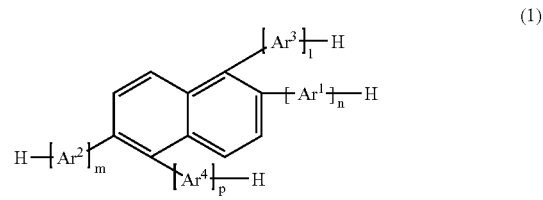

(1)

where: Ar$^1$ to Ar$^4$ each represent an aromatic hydrocarbon cyclic group having 6 to 18 carbon atoms forming a ring, the aromatic hydrocarbon cyclic group having none of anthracene skeleton, pyrene skeleton, aceanthrylene skeleton and naphthacene skeleton;

n, m and l each represent an integer in a range of 1 to 5; p represents an integer in a range of 0 to 5;

when the naphthalene derivative has a structure in which two naphthalene skeletons are consecutively bonded together, the structure of the naphthalene derivative is represented by any one of formulae (1-A), (1-B), (1-C) and (1-D) as follows;

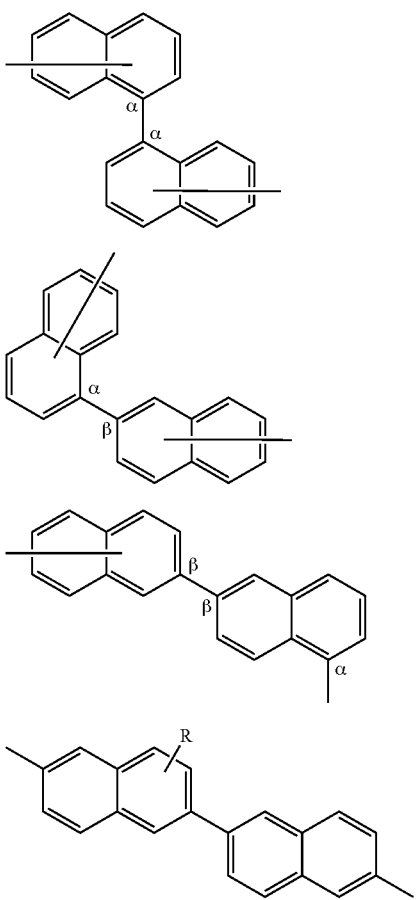

the naphthalene skeletons represented by the formulae (1-A), (1-B) and (1-C) each are allowed to have a substituent(s) at any position(s) or allowed to be unsubstituted;

R in the formula (1-D) represents a substituent, R being allowed to represent a single substituent or plural substituents, the single or plural substituent(s) being allowed to be in any position(s) of the two naphthalene skeletons; when R represents plural substituents, the plural substituents are allowed to be mutually the same or different;

when the naphthalene derivative has a structure in which three naphthalene skeletons are consecutively bonded together, a naphthalene skeleton of the three naphthalene skeletons that is positioned at the center of the structure is tetravalent or more while at least either one of the other naphthalene skeletons of the three naphthalene skeletons that are positioned at ends of the structure is trivalent or more;

when the naphthalene derivative has a structure in which four naphthalene skeletons are consecutively bonded together, at least one of the naphthalene skeletons is tetravalent or more;

when the naphthalene derivative contains a plurality of unsubstituted 9-phenanthrenes, the number of the unsubstituted 9-phenanthrenes is 3 or more; and when $Ar^1$ to $Ar^4$ each represent a phenanthrene skeleton in the naphthalene derivative, the phenanthrene skeleton is monovalent.

2. The naphthalene derivative according to claim 1, wherein $Ar^1$ to $Ar^4$ in the formula (1) each represent a benzene skeleton, a naphthalene skeleton, a fluorene skeleton, a phenanthrene skeleton, a fluoranthene skeleton, a triphenylene skeleton or a chrysene skeleton.

3. The naphthalene derivative according to claim 2, wherein, when $Ar^1$ to $Ar^4$ in the formula (1) each has a substituent, the substituent is selected from the group consisting of an aryl group having 6 to 30 carbon atoms, an alkyl group having 1 to 30 carbon atoms, a cycloalkyl group having 1 to 30 carbon atoms, an alkoxy group having 1 to 20 carbon atoms, a cyano group, a silyl group having 3 to 30 carbon atoms and a halogen atom.

4. The naphthalene derivative according to claim 1, wherein n, m and l in the formula (1) each represent an integer in a range of 1 to 3 while p represents an integer in a range of 0 to 3.

5. An organic electroluminescence device comprising the naphthalene derivative according to claim 1.

6. The organic electroluminescence device according to claim 5, further comprising a phosphorescent material.

7. The organic electroluminescence device according to claim 5, the naphthalene derivative being present in an emitting layer.

8. The naphthalene derivative according to claim 1, wherein the structure of the naphthalene derivative is represented by formula (1-A).

9. The naphthalene derivative according to claim 1, wherein the structure of the naphthalene derivative is represented by formula (1-B).

10. The naphthalene derivative according to claim 1, wherein the structure of the naphthalene derivative is represented by formula (1-C).

11. The naphthalene derivative according to claim 1, wherein the structure of the naphthalene derivative is represented by formula (1-D).

12. The naphthalene derivative according to claim 1, wherein the naphthalene derivative has a structure in which three naphthalene skeletons are consecutively bonded together.

13. The naphthalene derivative according to claim 1, wherein the naphthalene derivative has a structure in which four naphthalene skeletons are consecutively bonded together.

14. The naphthalene derivative according to claim 1, wherein the naphthalene derivative contains a plurality of unsubstituted 9-phenanthrenes.

15. The naphthalene derivative according to claim 1, wherein $Ar^1$ to $Ar^4$ each represent a phenanthrene skeleton in the naphthalene derivative.

* * * * *